US012751938B2

United States Patent

(12) United States Patent
Xu et al.

(10) Patent No.: US 12,751,938 B2
(45) Date of Patent: *Oct. 6, 2026

(54) THERAPEUTIC USES OF INHIBITORS OF THE RNA-BINDING PROTEIN HuR

(71) Applicant: University of Kansas, Lawrence, KS (US)

(72) Inventors: Liang Xu, Lawrence, KS (US); Xiaoqing Wu, Lawrence, KS (US); Lan Lan, Lawrence, KS (US); Jeff Aube, Chapel Hill, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 911 days.

This patent is subject to a terminal disclaimer.

(21) Appl. No.: 17/914,287

(22) PCT Filed: Mar. 22, 2021

(86) PCT No.: PCT/US2021/023410

§ 371 (c)(1),
(2) Date: Sep. 23, 2022

(87) PCT Pub. No.: WO2021/202137

PCT Pub. Date: Oct. 7, 2021

(65) Prior Publication Data

US 2023/0131501 A1 Apr. 27, 2023

Related U.S. Application Data

(60) Provisional application No. 63/001,631, filed on Mar. 30, 2020.

(51) Int. Cl.

*A61K 31/381* (2006.01)
*A61K 31/337* (2006.01)

(Continued)

(52) U.S. Cl.

CPC .......... *A61K 31/381* (2013.01); *A61K 31/337* (2013.01); *A61K 31/704* (2013.01); *A61P 1/18* (2018.01); *A61P 35/00* (2018.01)

(58) Field of Classification Search

None

See application file for complete search history.

(56) References Cited

U.S. PATENT DOCUMENTS

| | | | |
|---|---|---|---|
| 5,843,937 | A | 12/1998 | Wang et al. |
| 6,153,642 | A | 11/2000 | Cozzi et al. |

(Continued)

FOREIGN PATENT DOCUMENTS

| | | | |
|---|---|---|---|
| CN | 101648940 A * | 2/2010 | |
| WO | WO-2010/062171 A2 | 6/2010 | |
| WO | WO-2020/242719 A2 | 12/2020 | |

OTHER PUBLICATIONS

Wang et al., Cytoplasmic HuR expression correlates with angiogenesis, lymphangiogenesis, and poor outcome in lung cancer. Med Oncol 28 (Suppl 1), 577-585 (2011) (Year: 2011).*

(Continued)

*Primary Examiner* — Jeffrey S Lundgren
*Assistant Examiner* — Anthony Joseph Seitz
(74) *Attorney, Agent, or Firm* — Foley & Lardner LLP

(57) ABSTRACT

The present technology is directed to methods of treatment utilizing inhibitors of HuR interaction with RNA, where the inhibitors are of Formula I where $R^1$ is; and $X^1$ is OH, NH—OH, or 0-($C_1$-$C_8$ unsubstituted alkyl).

(I)

(Continued)

-continued (II)

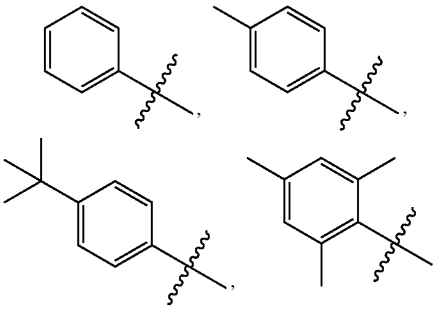

14 Claims, 61 Drawing Sheets

(51) Int. Cl.

| | |
|---|---|
| ***A61K 31/704*** | (2006.01) |
| ***A61P 1/18*** | (2006.01) |
| ***A61P 35/00*** | (2006.01) |

(56) References Cited

U.S. PATENT DOCUMENTS

| | | | | |
|---|---|---|---|---|
| 7,432,304 | B2 | 10/2008 | Wang et al. | |
| 2004/0204339 | A1* | 10/2004 | DiMartino ............. | A61K 38/12 514/183 |
| 2005/0137234 | A1 | 6/2005 | Bressi et al. | |
| 2006/0084647 | A1 | 4/2006 | Wang et al. | |
| 2010/0145036 | A1 | 6/2010 | Sufi et al. | |
| 2011/0028507 | A1 | 2/2011 | Kim et al. | |
| 2011/0207767 | A1 | 8/2011 | Beusker et al. | |
| 2015/0231142 | A1 | 8/2015 | Van Goor et al. | |
| 2016/0271105 | A1 | 9/2016 | Hadida-Ruah et al. | |
| 2018/0117166 | A1 | 5/2018 | Getts et al. | |
| 2022/0213052 | A1* | 7/2022 | Aube ................... | C07D 409/12 |

OTHER PUBLICATIONS

Brown, Bioisosteres in Medicinal Chemistry, 2012 (Year: 2012).*

Allegri et al., (2018). Effects of HuR downregulation on anaplastic thyroid cancer cells. Oncology Letters, 15, 575-579 (Year: 2018).*

Allan et al., "N-Benzyl-1-heteroaryl-3-(trifluoromethyl)-1H-pyrazole-5-carboxamides as inhibitors of co-activator associated arginine methyltransferase 1 (CARM1)", Bioorganic and Medicinal Chemistry Letters, 2009, vol. 19, pp. 1218-1223.

Baraldi et al., "Benzoyl and Cinnamoyl Nitrogen Mustard Derivatives of Benzoheterocyclic Analogues of the Tallimustine: Synthesis and Antitumour Activity", Bioorganic & Medicinal Chemistry , vol. 10, No. 5, 2002, pp. 1611-1618.

Extended European Search Report issued for EP Appl. Ser. No. 20813936.0 dated Aug. 18, 2022 (12 pages).

Extended European Search Report issued for EP Appl. Ser. No. 20813936.0 dtd May 19, 2022 (11 pages).

Hu et al., "Synthesis, structure-activity relationship studies and biological evaluation of novel 2,5-disubstituted indole derivatives as anticancer agents", Chemical Biology & Drug Design, vol. 88, No. 5, 2016, pp. 766-778.

International Search Report and Written Opinion for PCT Appl. Ser. No. PCT/US2020/031058 dated Jan. 14, 2021 (17 pages).

Invitation to Pay Additional Fees and, Where Applicable, Protest Fee mailed in Appl. Ser. No. PCT/US2020/031058 on Nov. 3, 2020 (2 pages).

Manzoni et al., "Interfering with HuR-RNA Interaction : Design, Synthesis and Biological Characterization of Tanshinone Mimics as Novel, Effective HuR Inhibitors", Journal of Medicinal Chemistry, vol. 61, No. 4, 2018 (16 pages).

PubChem—CID—137990205, Create Date: Apr. 26, 2019 (Apr. 26, 2019), 8 pages.

PubChem—CID—46424910, Create Date: Jul. 23, 2010 (Jul. 23, 2010), 7 pages.

Wu et al., "The RNA Binding Protein HuR: A Promising Drug Target for Anticancer Therapy", Current Cancer Drug Treatments, 2019, vol. 19, No. 5, p. 382-399.

Wu et al., "Identification and Validation of Novel Small Molecule Disruptors of HuR-mRNA Interaction", ACS Chemical Biology, vol. 10, No. 6, 2015, pp. 1476-1484.

Registry (STN) (online), Jun. 17, 2010 (Date of Search Jan. 27, 2025), CAS Registry Nos. 1227962-52-8 and 1227962-53-9, (Year; 2010).

Non-Final Office Action issued in U.S. Appl. No. 17/607,003 mailed Feb. 5, 2025.

International Search Report and Written Opinion issued for Appl. Ser. No. PCT/US2021/023410 dated Jun. 8, 2021 (6 pages).

Pubmed Compound Record for CID 45138015, 'Ethyl (E)-3-[5-((4-methylphenyl)sulfonylamino]-1-benzothiophen-2-yl]prop-2-enoate', U.S. National Library of Medicine, Apr. 26, 2010, pp. 1-6 (https://pubchem.ncbi.nlm.nih.gov/compound/45138015); p. 2.

Pubmed Compound Record for CID 45138018, '(e)-3-(5-((4-(t-Butyl)phenyl) sulfonamido) benzo[b]thiophen-2-yl)-N-hydroxyacrylamide', U.S. National Library of Medicine, Apr. 26, 2010, pp. 1-9 (https://pubchem.ncbi.nlm.nih.gov/compound/45138018); p. 2.

National Center for Biotechnology Information. "PubChem Compound Summary for CID 46424910, Ethyl 5-(pyridine-2-carbonylamino)-1-benzothiophene-2-carboxylate" PubChem, https://pubchem.ncbi.nlm. nih.gov/compound/46424910. Accessed Oct. 7, 2024. (Year: 2024).

Restriction Requirement issued in U.S. Appl. No. 17/607,003 mailed Oct. 18, 2024.

Final Office Action issued in U.S. Appl. No. 17/607,003 mailed May 12, 2025.

* cited by examiner

1: cell lysate (input, 1/30); 2: Random-Bi; 3: Msi1-Bi;
4: Msi1-Bi + unlabeled Msi1; 5: Msi1-Bi + KH-3

THERAPEUTIC USES OF INHIBITORS OF THE RNA-BINDING PROTEIN HuR

CROSS-REFERENCE TO RELATED APPLICATIONS

This application is a U.S. National Phase Application under 35 U.S.C. 371 of International Application No. PCT/US2021/023410, filed on Mar. 22, 2021, which claims the benefit of and priority to U.S. Provisional Appl. No. 63/001,631, filed Mar. 30, 2020, each of which is incorporated herein by reference in its entirety.

U.S. GOVERNMENT RIGHTS

This invention was made with government support CA178831, CA191785, and CA243445 awarded by National Institutes of Health, and under W81XWH-16-1-0729 awarded by the Department of Defense. The government has certain rights in the invention.

FIELD

The present technology is directed to methods of inhibiting of the interaction between RNA-binding protein Hu antigen R (HuR) and its cellular targets. The technology is suited to treat varying types of cancer.

SUMMARY

In an aspect, a method is provided the includes administering a compound of Formula I or a pharmaceutically acceptable salt thereof to a subject suffering from a hyperproliferative disease with HuR overexpression (I)

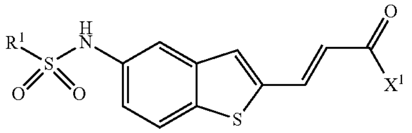

wherein $R^1$ is

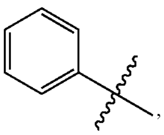
,
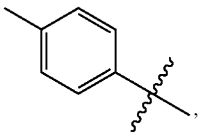
,
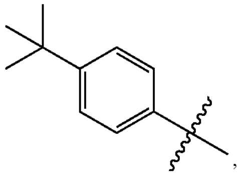
, or
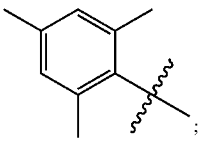
;

and $X^1$ is OH, NH—OH, or O—($C_1$-$C_8$ unsubstituted alkyl).

A pharmaceutical composition for use in treating a hyperproliferative disease with HuR overexpression, the composition comprising an effective amount of a compound of Formula I or a pharmaceutically acceptable salt thereof.

DESCRIPTION OF THE DRAWINGS

FIG. 6A illustrates that KH-3 (a compound of the present technology described herein) partially disrupts endogenous HuR binding with Msi1 RNA oligo in an RNA-TP assay. KH-3 is also shown to partially block endogenous HuR interaction with target mRNAs in RNP-TP assay in HCT-116 β/w cells (FIG. 6B) and MDA-MB-231 cells (FIG. 6C).

FIG. 10A illustrates the results of cytotoxicity assays utilizing docetaxel against MDA-MB-231 cells as compared to a docetaxel-resistant MDA-MB-231 cell line ("231-TR"), where FIG. 10C provides a Western blot analysis illustrating that 231-TR cells have increased cytoplasmic HuR as well as HuR target encoding proteins compared to MDA-MB-231 cells. FIG. 10B illustrates the results of cytotoxicity assays utilizing doxorubicin ("DXR") against MDA-MB-231 cells as compared to a doxorubicin-resistant MDA-MB-231 cell line ("231-DR"), where FIG. 10D provides a Western blot analysis illustrating that 231-DR cells have increased cytoplasmic HuR as well as HuR target encoding proteins compared to MDA-MB-231 cells. FIG. 10E illustrates the results of cytotoxicity assays utilizing a compound of the present technology (KH-3) against MDA-MB-231 cells, 231-TR cells, and 231-DR cells.

DETAILED DESCRIPTION

Figure 1A:
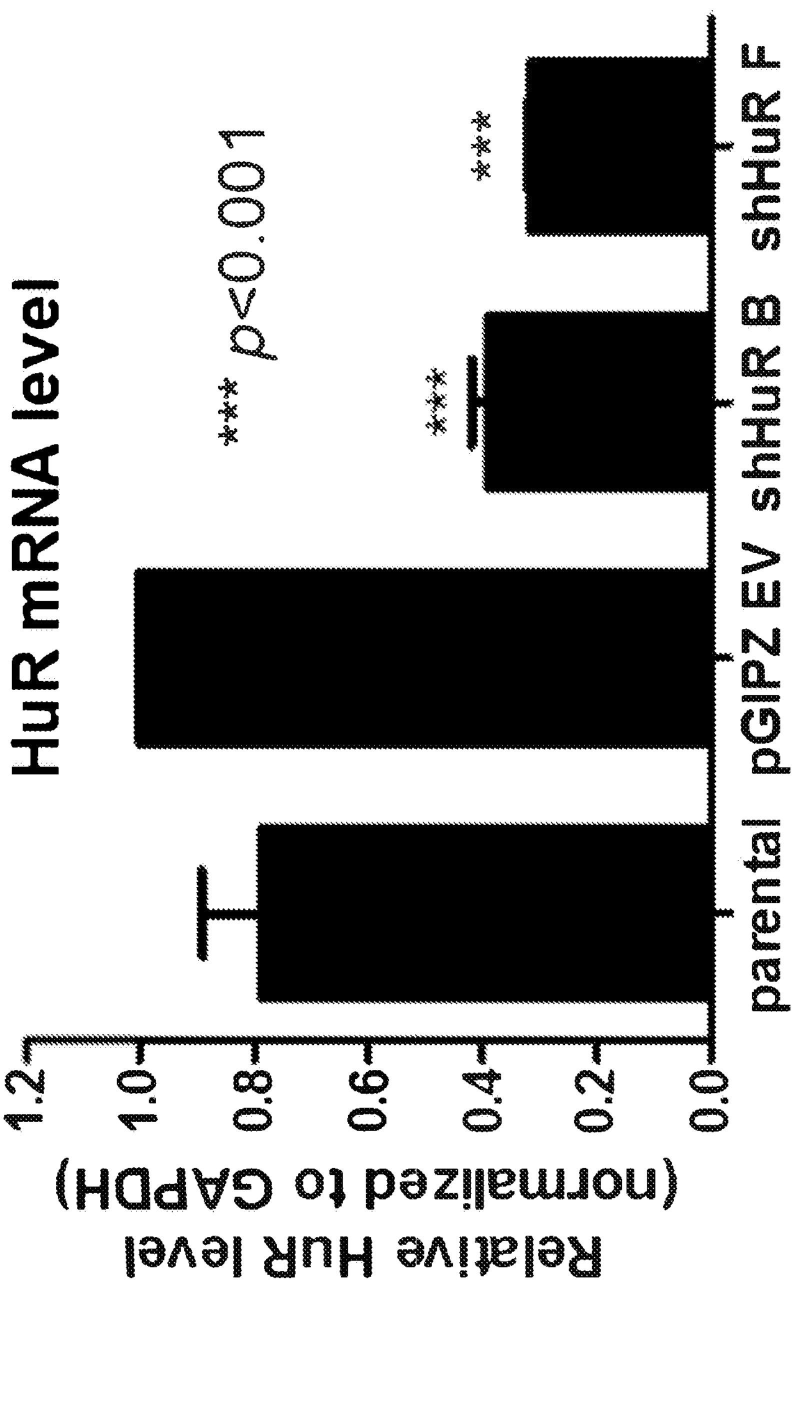
FIGS. 1A-1F provide the results of studies illustrating RNA-binding protein Hu antigen R (HuR) is involved in chemo/radiation-induced tumor response, according to the working examples. HuR knock-down by shRNAs in PC3 cells (FIG. 1A) resulted in reduced cell growth and colony formation (FIG. 1). Docetaxel (TXT) treatment increased the mRNA levels of HuR target Musashi 2 (Msi2) in PC3 cells (FIG. 1C), but not in PC3 with HuR knock-down (FIG. 1D), indicating that HuR is required for chemo-induced response. X-ray radiation also increased the mRNA level of HuR target Msi2 (FIG. 1E). HuR knock-down by siRNA sensitized cancer cells to X-ray radiation, with an enhancement ratio (ER) of 1.5 versus the negative control (NC) siRNA (FIG. 1F).
Figure 1B:
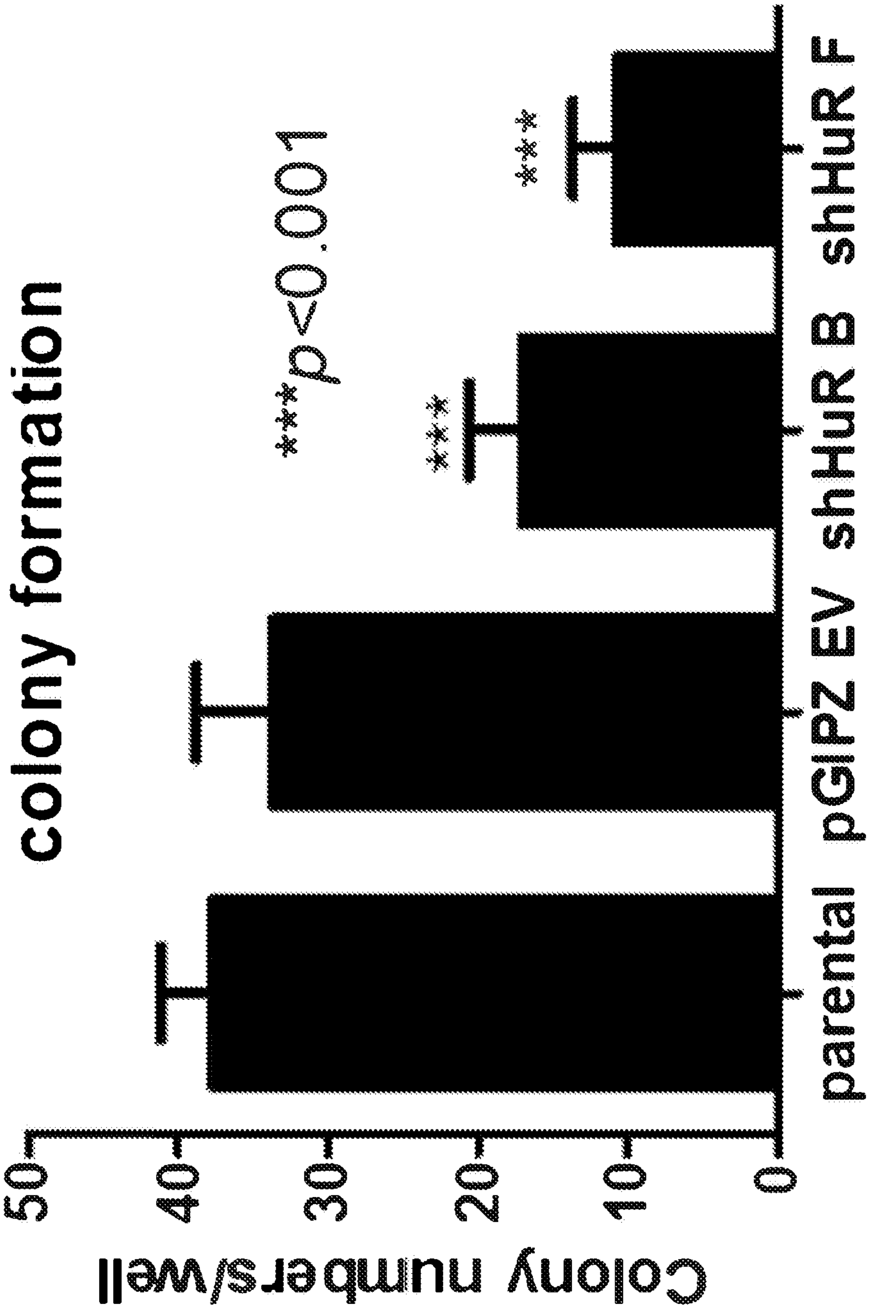
Figure 1C:
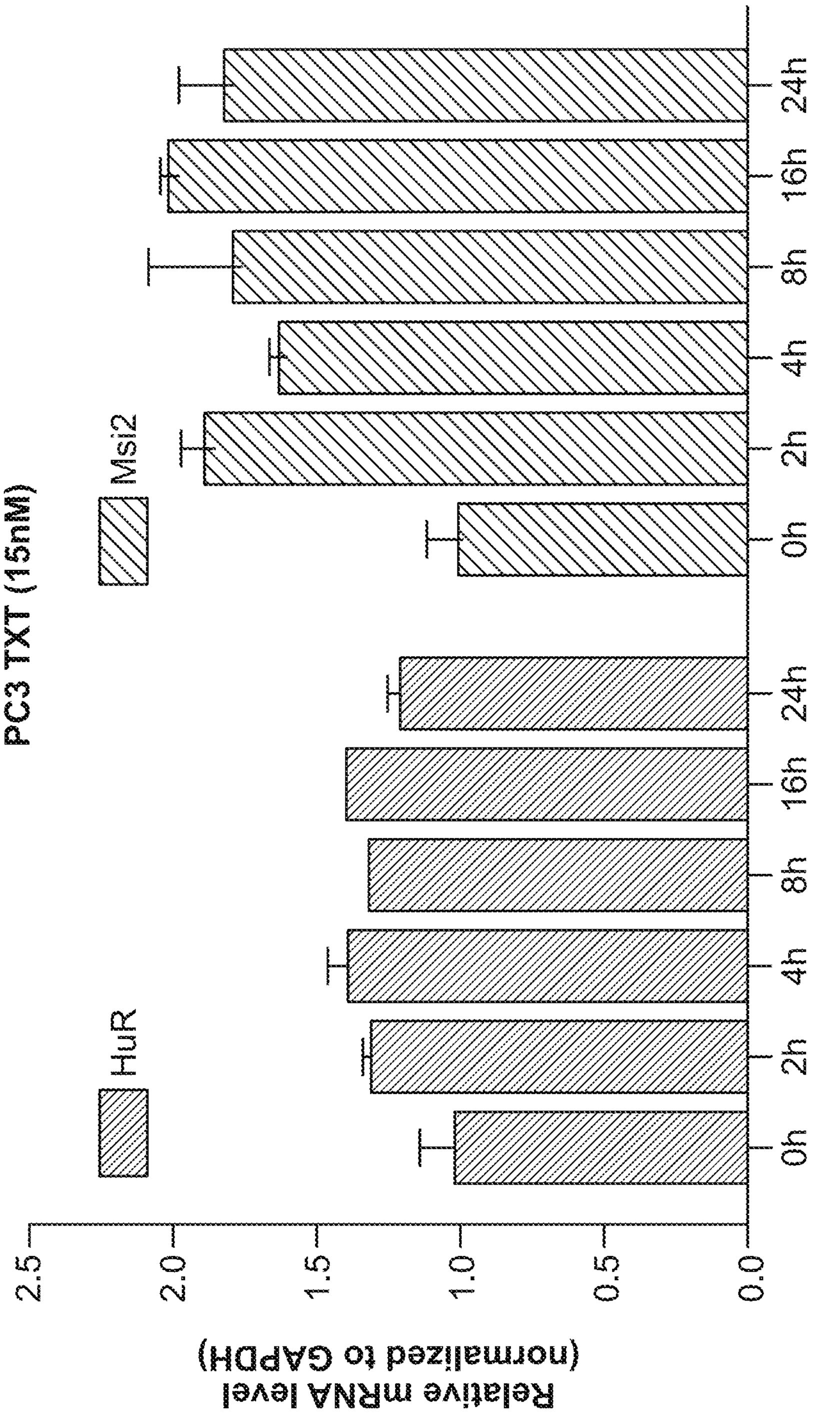
Figure 1D:
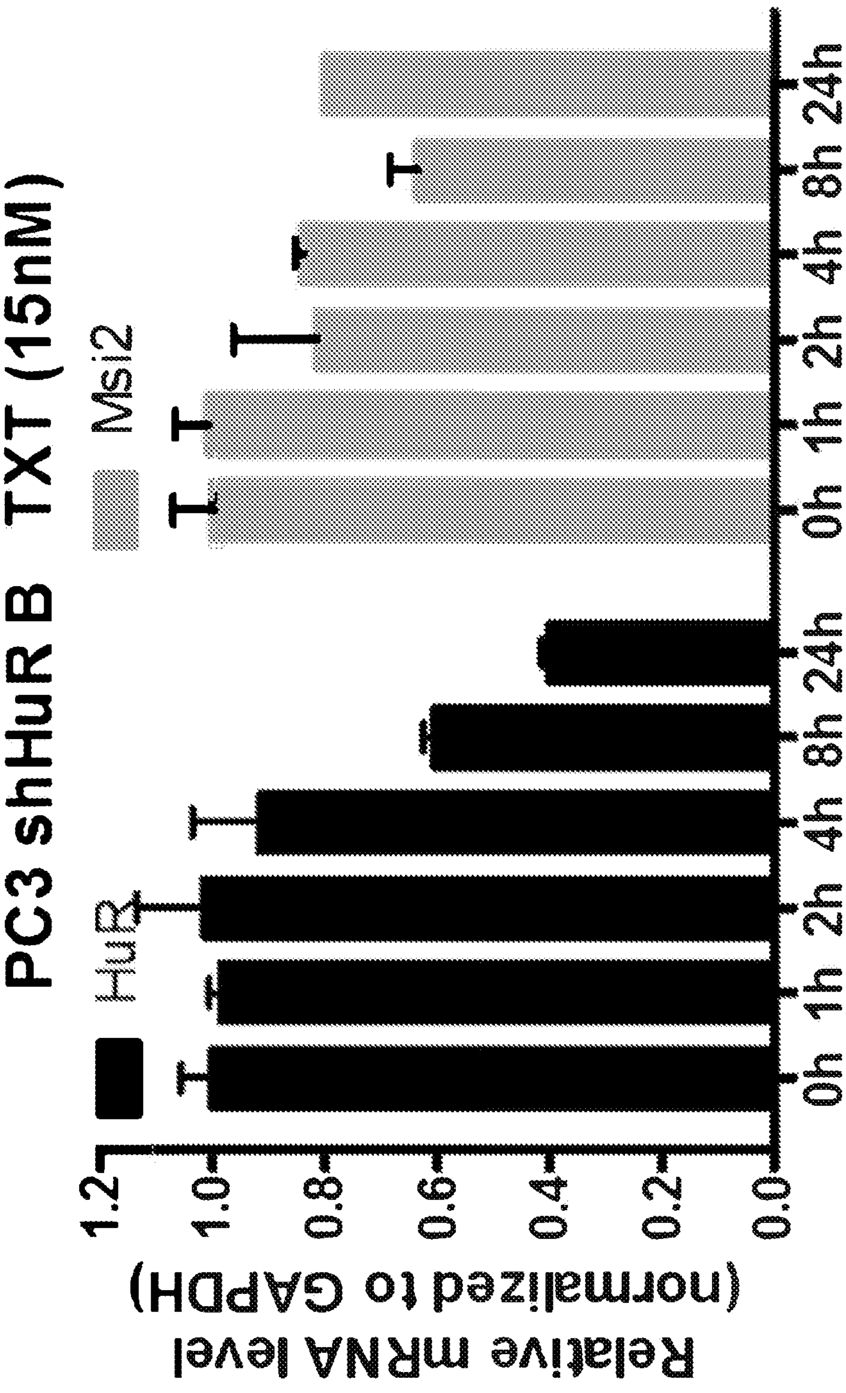
Figure 1E:
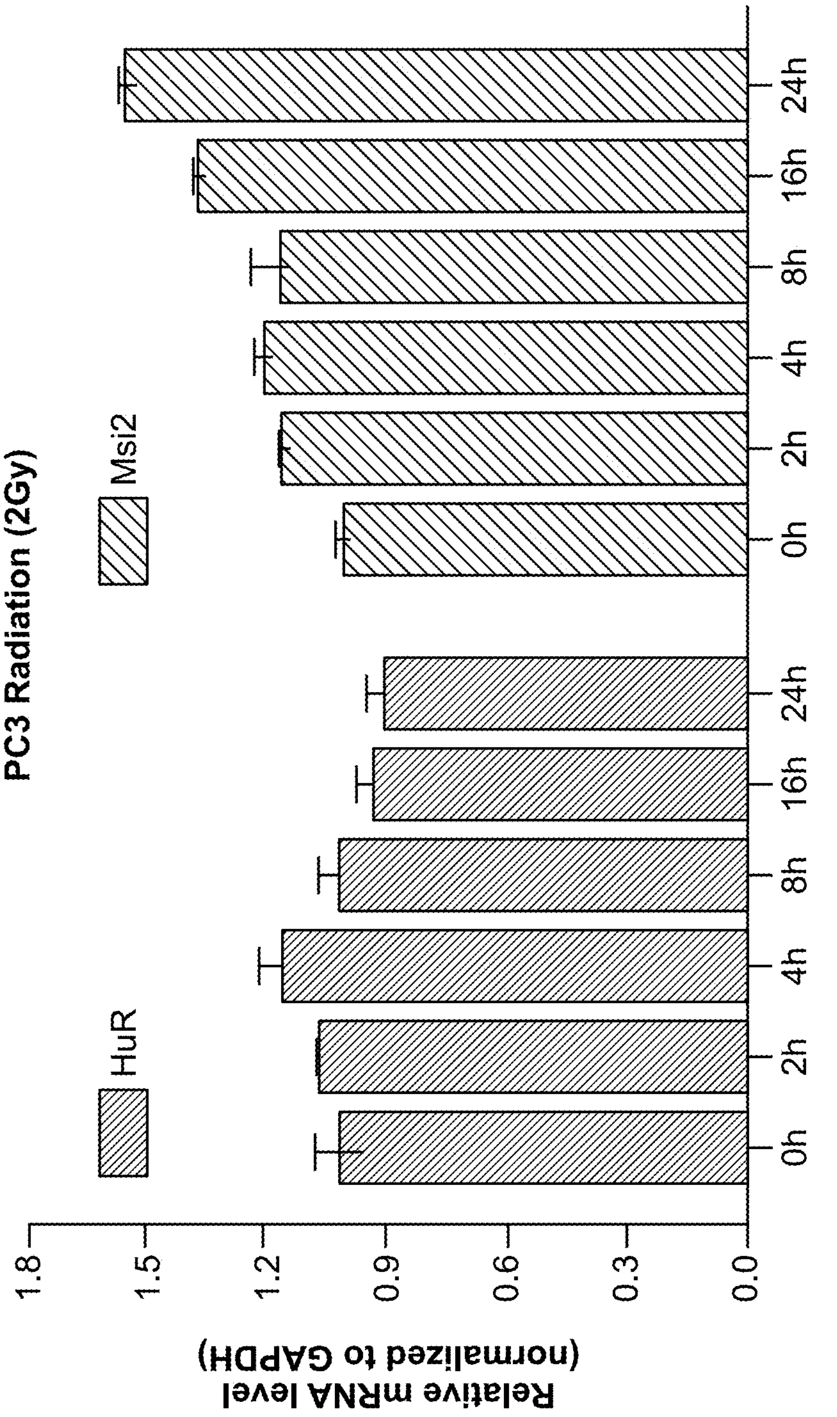
Figure 1F:
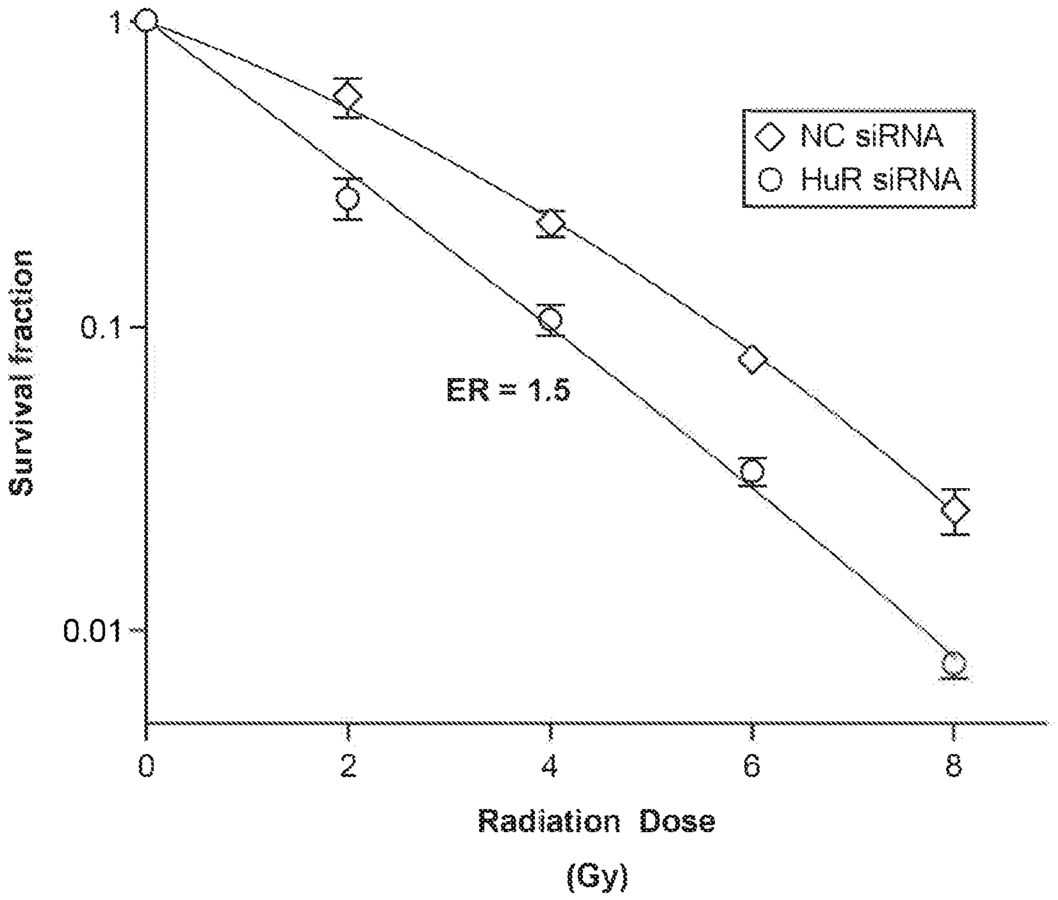

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 weight %" would be understood to mean "9 weight % to 11 weight %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

The phrase "and/or" as used in the present disclosure will be understood to mean any one of the recited members individually or a combination of any two or more thereof—for example, "A, B, and/or C" would mean "A, B, C, A and B, A and C, or B and C."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; and nitriles (i.e., CN).

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical, or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

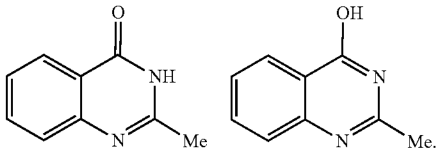

As another example, guanidines may exhibit the following isomeric forms in protic organic solution, also referred to as tautomers of each other:

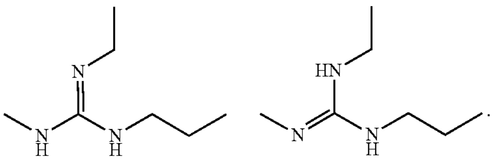

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Throughout this disclosure, various publications, patents and published patent specifications are referenced by an identifying citation. Also within this disclosure are Arabic numerals referring to referenced citations, the full bibliographic details of which are provided preceding the claims.

The disclosures of these publications, patents and published patent specifications are hereby incorporated by reference into the present disclosure.

The Present Technology

Post-transcriptional gene regulation occurs at the levels of pre-mRNA splicing and maturation, as well as mRNA transport, editing, storage, stability, and translation. This level of gene regulation is essential for normal development, but when dysregulated, has many implications in disease conditions, including cancer. These functions are mediated by RNA-binding proteins (RBPs), which thus present targets for cancer therapy.

The RBP Hu antigen R ("HuR") is a member of the embryonic lethal abnormal vision ("ELAV") family that binds to adenine- and uridine-rich elements (collectively, "ARE") located in the 3'- or 5'-untranslated region ("UTR") of target mRNAs.[1] HuR is elevated in a broad range of cancer tissues compared with the corresponding normal tissues[2]. In early reports, upregulated HuR in brain and colon cancers was linked to the enhanced expression of COX-2, VEGF, TGF-β, IL-8, and other cancer-associated proteins 3,4 Subsequent studies revealed that HuR was broadly overexpressed in virtually all malignancies tested, including cancers of the colon[2,5,6] prostate[7,8], breast[9], brain[3], ovaries[10], pancreas[11], and lung[12]. Elevated cytoplasmic accumulation of HuR correlates with high-grade malignancy and serves as a prognostic factor of poor clinical outcome in those cancers[13-15].

Moreover, HuR is proposed to play a causal role in tumor development/progression. Cancer cells with elevated HuR produced significantly larger tumors than those arising from control populations in a mouse xenograft model[2], while reduced HuR level led to decreased tumor size[16].

HuR contains three RNA recognition motifs ("RRM"), of which RRM1 and RRM2 are involved in RNA binding, whereas RRM3 does not contribute to RNA binding but is needed for cooperative assembly of HuR oligomers on RNA.[17] Recently the crystal structure of two N-terminal RRM domains (namely, RRM1 and RRM2) of HuR complexed with RNA was reported.[18] HuR target mRNAs bear AREs in their 3'- or 5'-UTRs. Many cytokine and proto-oncogene mRNAs have been identified as containing AREs within their 3'-UTRs, which confer a short mRNA half-life.[19] Cytoplasmic binding of HuR to these ARE-containing mRNAs is generally accepted to lead to mRNA stabilization and increased translation[20,21]. HuR promotes tumorigenesis by interacting with a subset of mRNAs which encode proteins implement in different tumor processes including cell proliferation, cell survival, angiogenesis, invasion, and metastasis[13-15]. HuR also promotes the translation of several target mRNAs encoding proteins that are involved in cancer treatment resistance[15,22,23]. HuR up-regulates the oncogenic Musashi1 (Msi1)[24], Musashi2 (Msi2)[25,26] and anti-apoptotic proteins, Bcl-2[22] and XIAP[23], via binding AREs and promoting mRNA stability and translation, thus leading to activation of Wnt/Notch signaling pathways and inhibition of apoptosis. Wnt/Notch pathways are involved in cancer stem cells (CSCs)[27-30].

Figure 2:
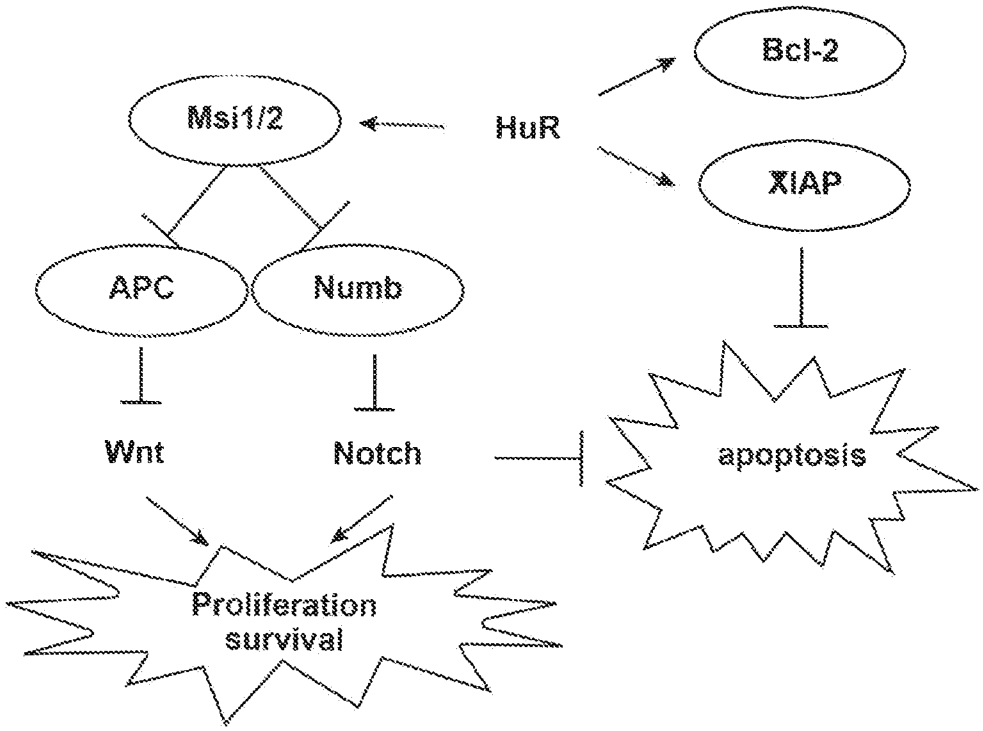
FIG. 2 provides a schematic of the proposed influence of HuR on apoptosis and Notch/Wnt signaling pathways, according to the working examples. Musashi 1 and Musashi 2 (Msi1/2) act through Notch and Wnt signaling to stimulate cell proliferation and survival and inhibit apoptosis. HuR is implicated in both pathways via increasing stability and translation of Msi1/2 mRNA. HuR also inhibits apoptosis by up-regulating anti-apoptotic genes Bcl-2 and XIAP.

Consistent with the literature, our preliminary studies presently disclosed here (FIG. 1) also show that HuR knock-down resulted in inhibition of tumor cell growth/colony formation and sensitization to chemo/radiation, and chemo/radiation led to the HuR-mediated upregulation of Msi1/2, followed with Wnt/Notch activation. Without being bound by theory, it appears cancer cells use HuR, a master switch of multiple oncogenic mRNAs, as a response to counter chemo/radiation and to promote survival, thus rendering the cancer cells with HuR overexpression resistant to chemo/radiotherapy (See FIG. 2). Furthermore, among the HuR downstream signaling pathways, HuR-Bcl-2/XIAP and HuR-Msi1/2 pathways appear to be involved in the HuR-mediated chemo/radioresistance. Taken together, the published studies and our work indicate that HuR is a cancer therapy target.

Although there are many examples of compounds which specifically interfere with protein-protein interactions, there is limited success of drug discovery for protein-RNA interactions, especially for HuR.

The present technology is directed to methods of using compounds that inhibit the binding of RNA and HuR for inducing preferential inhibition and death of the cells with HuR overexpression and/or downstream signaling dysregulation, and for sensitizing such cells to the induction of cell death and/or growth inhibition by the conventional therapies.

In an aspect, the present technology provides a method that includes administering a compound of Formula I or a pharmaceutically acceptable salt thereof to a subject (I)

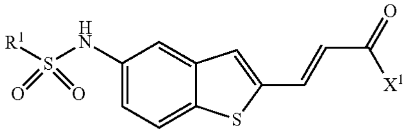

wherein $R^1$ is

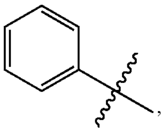,
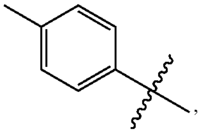,
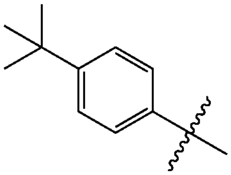, or
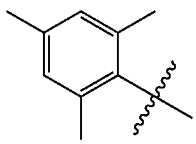;

and $X^1$ is OH, NH—OH, or O—($C_1$-$C_8$ unsubstituted alkyl). It may be the subject is suffering from a condition, where the condition is a hyperproliferative disease with HuR overexpression. The hyperproliferative disease with HuR overexpression may include one or more of a colon cancer, a prostate cancer, a breast cancer (e.g., triple negative breast cancer), a brain cancer, an ovarian cancer, a pancreatic cancer, or a lung cancer. It may be the method includes administering an effective amount of a compound of Formula I (or a pharmaceutically acceptable salt thereof). Administration of a compound of Formula I (or a pharmaceutically acceptable salt thereof) may be via administration a pharmaceutical composition (as described herein) that includes a compound of Formula I or a pharmaceutically acceptable salt thereof.

In any embodiment herein, it may be that $X^1$ is OH, NH—OH, or O—($C_1$-$C_6$ unsubstituted alkyl). It should be noted that compounds where $X^1$ is O—($C_1$-$C_8$ unsubstituted alkyl) or O—($C_1$-$C_6$ unsubstituted alkyl) are especially suited as intermediates in the synthesis of active compounds where $X^1$ is OH or NH—OH, as illustrated in the working examples. However, compounds where $X^1$ is O—($C_1$-$C_8$ unsubstituted alkyl) or O—($C_1$-$C_6$ unsubstituted alkyl) may themselves be used as pro-drug compounds (for example, where esterases in a subject will convert $X^1$ in vivo into OH). In any embodiment herein, it may be that $X^1$ is OH or NH—OH. In any embodiment herein, it may be that $X^1$ is NH—OH.

In a related aspect, a pharmaceutical composition is provided, the pharmaceutical composition including an effective amount of the compound of any embodiments of compounds of Formula I (or pharmaceutically acceptable salt thereof) for treating a condition; and where the condition is a hyperproliferative disease with HuR overexpression. The hyperproliferative disease with HuR overexpression may include one or more of a colon cancer, a prostate cancer, a breast cancer (e.g., triple negative breast cancer), a brain cancer, an ovarian cancer, a pancreatic cancer, or a lung cancer.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of a hyperproliferative disease with HuR overexpression. Another example of an effective amount includes amounts or dosages that reduce the size of tumors associated with one or more of a colon cancer, a prostate cancer, a breast cancer (e.g., triple negative breast cancer), a brain cancer, an ovarian cancer, a pancreatic cancer, or a lung cancer that exhibit HuR overexpression. As used herein, a "subject" or "patient" is a mammal, such as a cat, dog, rodent or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising any of the compounds of Formula I disclosed herein and optionally a pharmaceutically acceptable carrier or one or more excipients or fillers. The compositions may be used in the methods and treatments described herein. Such compositions and medicaments include a therapeutically effective amount of any compound as described herein. The pharmaceutical composition may be packaged in unit dosage form. The unit dosage form is effective in treating a hyperproliferative disease with HuR overexpression when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat a hyperproliferative disease with HuR overexpression. The compounds and compositions described herein may be used to prepare formulations and medicaments that prevent or treat a variety of disorders associated with a hyperproliferative disease with HuR overexpression. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts until the progression of the condition/disease state is decreased or stopped. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

The compounds of the present technology can also be administered to a patient along with other conventional therapeutic agents that may be useful in the treatment a hyperproliferative disease with HuR overexpression. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of a hyperproliferative disease with HuR overexpression.

In an aspect, a compound of the present technology may be administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects, or embodiments of the present technology.

EXAMPLES

All solvents and reagents were used as received from commercial suppliers, unless noted otherwise. $^{1}H$ and $^{13}C$ NMR spectra were recorded on a Bruker AM or Varian 400 spectrometer (operating at 400 and 101 MHz respectively) or a Bruker AVIII spectrometer (operating at 500 and 126 MHz respectively) in $CDCl_3$ with 0.03% TMS as an internal standard. The chemical shifts (6) reported are given in parts per million (ppm) and the coupling constants (J) are in Hertz (Hz). The spin multiplicities are reported as s=singlet, d=doublet, t=triplet, q=quartet, dd=doublet of doublet, ddd=doublet of doublet of doublet, dt=doublet of triplet, td=triplet of doublet, and m=multiplet. Microwave reactions were carried out using a Biotage Initiator Classic. Column chromatography separations were performed using the Teledyne Isco CombiFlash Rf using RediSep Rf silica gel columns. The analytical RPLC method used an Agilent 1200 RRLC system with UV detection (Agilent 1200 DAD SL) and mass detection (Agilent 6224 TOF). The analytical method conditions included a Waters Aquity BEH C18 column (2.1×50 mm, 1.7 μm) and elution with a linear gradient of 5% acetonitrile in pH 9.8 buffered aqueous ammonium formate to 100% acetonitrile at 0.4 mL/min flow rate. Automated preparative RP HPLC purification was performed using an Agilent 1200 Mass-Directed Fractionation system (Prep Pump G1361 with gradient extension, make-up pump G1311A, pH modification pump G1311A, HTS PAL autosampler, UV-DAD detection G1315D, fraction collector G1364B, and Agilent 6120 quadrapole spectrometer G6120A). The preparative chromatography conditions included a Waters X-Bridge C18 column (19×150 mm, 5 um, with 19×10-mm guard column), elution with a water and acetonitrile gradient, which increases 20% in acetonitrile content over 4 min at a flow rate of 20 mL/min (modified to pH 9.8 through addition of NH4OH by auxiliary pump), and sample dilution in DMSO. The preparative gradient, triggering thresholds, and UV wavelength were selected according to the analytical RP HPLC analysis of each crude sample. Compound purity was measured on the basis of peak integration (area under the curve) from UV-Vis absorbance at 214 nm, and compound identity was determined on the basis of mass spectral and NMR analyses.

An exemplary synthetic protocol for benzothiophene-containing esters, carboxylic acids, and hydroxamic acids is illustrated in Scheme 1.

Scheme 1.

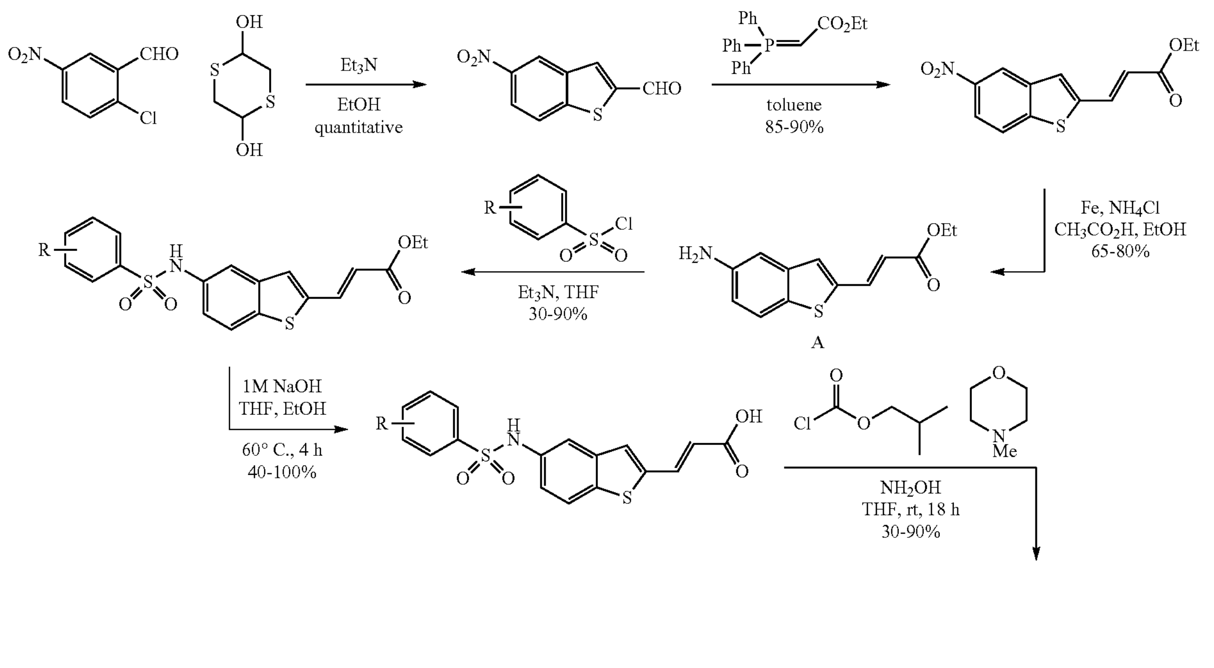

-continued

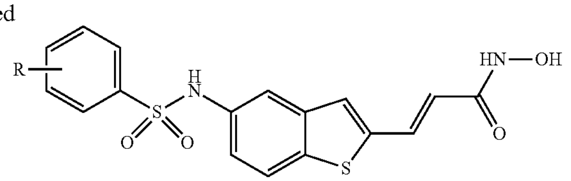

Representative Procedure for Synthesis of Esters of the Present Technology: To a solution of the aniline A (0.802 mmol, 1 eq.) in THF (4.27 mL) was add the corresponding sulfonyl chloride (1.203 mmol, 1.5 eq.) followed by triethylamine (2.005 mmol, 3 eq.). The reaction mixture was stirred at rt for 16 h. Upon completion the reaction mixture was quenched with 1 N HCl and extracted with EtOAc (×3) and dried over anhydrous $Na_2SO_4$. The evaporated residue was purified via silica gel chromatography (normal phase combiflash using hexanes and ethyl acetate). Isolated material was typically provided as an off-white solid.

(E)-ethyl 3-(5-(phenylsulfonamido)benzo[b]thiophen-2-yl)acrylate (KH-1B)

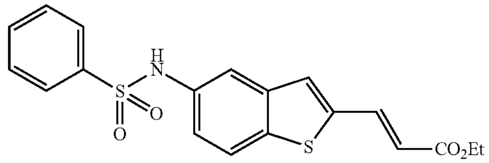 [SMILES: CCOC(=O)/C=C/c1cc2cc(NS(=O)(=O)c3ccccc3)ccc2s1]

Pale-yellow solid (226.1 mg, 0.584 mmol, 72% yield). $^1$H NMR (400 MHz, $CDCl_3$) δ 7.86-7.74 (m, 3H), 7.62 (dt, J=8.7, 0.7 Hz, 1H), 7.57-7.48 (m, 2H), 7.47-7.37 (m, 2H), 7.33 (s, 1H), 7.11 (s, 1H), 7.08 (dd, J=8.6, 2.2 Hz, 1H), 6.32-6.23 (m, 1H), 4.27 (q, J=7.1 Hz, 2H), 1.34 (t, J=7.1 Hz, 3H). $^{13}$C NMR (101 MHz, $CDCl_3$) δ 166.4, 141.2, 140.2, 138.9, 137.4, 137.2, 133.7, 133.1, 129.1, 128.0, 127.2, 123.2, 121.4, 120.1, 117.6, 60.8, 14.3. HRMS (m/z): calcd for $C_{19}H_{18}NO_4S_2$ ([M]$^+$+H) 388.0672; found 388.0683.

(E)-ethyl 3-(5-(4-methylphenylsulfonamido)benzo[b]thiophen-2-yl)acrylate (KH-2B)

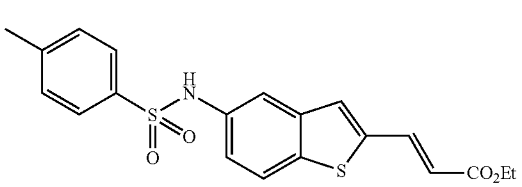 [SMILES: CCOC(=O)/C=C/c1cc2cc(NS(=O)(=O)c3ccc(C)cc3)ccc2s1]

Yellow solid (133.8 mg, 0.333 mmol, 82%). $^1$H NMR (400 MHz, $CDCl_3$) δ 7.80 (d, J=15.6 Hz, 1H), 7.69-7.64 (m, 2H), 7.61 (d, J=8.6 Hz, 1H), 7.52 (d, J=2.1 Hz, 1H), 7.32 (s, 1H), 7.24-7.18 (m, 2H), 7.16 (s, 1H), 7.09 (dd, J=8.6, 2.1 Hz, 1H), 6.27 (d, J=15.6 Hz, 1H), 4.27 (q, J=7.1 Hz, 2H), 2.35 (s, 3H), 1.34 (t, J=7.1 Hz, 3H). $^{13}$C NMR (101 MHz, $CDCl_3$) δ 166.4, 144.0, 141.1, 140.2, 137.2, 135.9, 133.9, 129.7, 128.0, 127.3, 123.1, 121.2, 120.1, 117.3, 60.8, 21.5, 14.3. HRMS (m/z): calcd for $C_{20}H_{20}NO_4S_2$ ([M]$^+$+H) 402.0828; found 402.0812.

(E)-ethyl 3-(5-(4-(tert-butyl)phenylsulfonamido)benzo[b]thiophen-2-yl)acrylate (KH-3B)

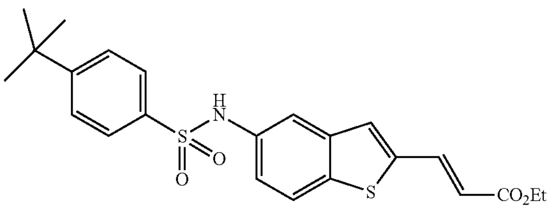 [SMILES: CCOC(=O)/C=C/c1cc2cc(NS(=O)(=O)c3ccc(C(C)(C)C)cc3)ccc2s1]

Light-yellow solid (308.4 mg, 0.695 mmol, 86% yield). $^1$H NMR (400 MHz, $CDCl_3$) δ 7.81 (d, J=15.6 Hz, 1H), 7.76-7.68 (m, 2H), 7.62 (d, J=8.6 Hz, 1H), 7.55 (d, J=2.1 Hz, 1H), 7.47-7.38 (m, 2H), 7.33 (s, 1H), 7.24 (s, 1H), 7.11 (dd, J=8.7, 2.1 Hz, 1H), 6.32-6.23 (m, 1H), 4.27 (q, J=7.1 Hz, 2H), 1.34 (t, J=7.1 Hz, 3H), 1.28 (s, 9H). $^{13}$C NMR (101 MHz, $CDCl_3$) δ 166.4, 156.9, 141.1, 140.2, 137.2, 137.1, 136.0, 134.0, 128.0, 127.1, 126.1, 123.1, 121.1, 120.0, 117.0, 60.8, 35.1, 31.0, 14.3. HRMS (m/z): calcd for $C_{23}H_{26}NO_4S_2$ ([M]$^+$+H) 444.1298; found 444.1316.

(E)-ethyl 3-(5-(2,4,6-trimethylphenylsulfonamido)benzo[b]thiophen-2-yl)acrylate (KH-4B)

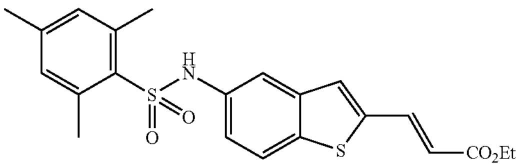 [SMILES: CCOC(=O)/C=C/c1cc2cc(NS(=O)(=O)c3c(C)cc(C)cc3C)ccc2s1]

Yellow solid (159.6 mg, 0.372 mmol, 46% yield). $^1$H NMR (400 MHz, DMSO-$d_6$) δ 10.33 (s, 1H), 7.89-7.74 (m, 3H), 7.44 (d, J=2.1 Hz, 1H), 7.11 (dd, J=8.7, 2.1 Hz, 1H), 6.97 (s, 2H), 6.28 (d, J=15.7 Hz, 1H), 4.18 (q, J=7.1 Hz, 2H), 2.55 (s, 6H), 2.19 (s, 3H), 1.25 (t, J=7.1 Hz, 3H). $^{13}$C NMR (101 MHz, DMSO) δ 165.5, 142.0, 140.0, 139.7, 138.6, 137.4, 135.1, 135.0, 133.6, 131.7, 129.2, 123.3, 119.7, 119.2, 114.5, 60.2, 22.4, 20.3, 14.1. HRMS (m/z): calcd for $C_{22}H_{24}NO_4S_2$ ([M]$^+$+H) 430.1141; found 430.1133.

Representative Procedure for Synthesis of Carboxylic Acids of the Present Technology:

To a solution of ester (0.127 mmol, 1 eq.) in a mixture of EtOH (0.740 mL) and THF (0.740 mL) (ratio volume, 1:1) was added 1M sodium hydroxide (0.254 mmol, 0.254 mL, 2 eq.) and the reaction was refluxed (65° C.) for 4 h. Upon completion, the reaction mixture was concentrated and diluted with 1N HCl. The aqueous layer was extracted with EtOAc (×3). The combined layer was washed with brine, dried over anhydrous $Na_2SO_4$, and concentrated in vacuo to provide corresponding carboxylic acids as off-white solid.

As additional step of reverse phase chromatography (using water and acetonitrile, 0 to 100% gradient) could be employed should it prove necessary for further purification.

Representative Procedure for Synthesis of Hydroxamic Acids of the Present Technology:

To the appropriate carboxylic acids, e.g., provided above, (0.047 mmol) in THE (0.5 mL) was added isobutyl chloroformate (0.094 mmol, 0.012 mL, 2 eq.) and N-methylmorpholine (0.094 mmol, 0.0103 mL, 2 eq.) at room temperature and the reaction was run for 1 h. Upon the formation of the activated anhydride, the reaction mixture was filtered first through a fritted filter followed by a syringe filter. Note, for small scale reactions (less than 0.1 mmol), filtration through syringe filter would suffice. 2×1 mL of THF was used for rinsing purpose. In a separate 2-dram vial containing a solution of hydroxylamine (50% in water, 0.469 mmol, 0.029 mL, 10 eq.) in THE (0.1 mL) was added the filtrate at room temperature and stirred for 18 h. Upon completion, solvents were removed in vacuo and the residue was dissolved in EtOAc (2 mL) and washed with saturated solution of NH4Cl or 1 N HCl. The aqueous layer was extracted with EtOAc (2 mL×3). The combined layer was washed with brine, dried over anhydrous $Na_2SO_4$, and concentrated in vacuo. The residue was purified via reverse phase chromatography (using water and acetonitrile, 0 to 100% gradient) to isolate the corresponding hydroxamic acids. Further guidance regarding synthesis of hydroxamic acids of the present technology may be found in Chinese Patent Publication No. 101648940A, published Feb. 17, 2010.

(E)-3-(5-(phenylsulfonamido)benzo[b]thiophen-2-yl) acrylic acid (KH-1A)

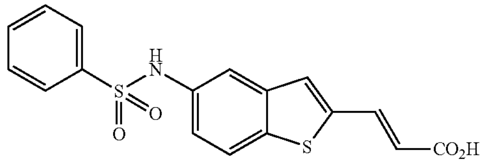 [SMILES: O=C(O)/C=C/c1cc2cc(NS(=O)(=O)c3ccccc3)ccc2s1]

Pale-yellow solid (187.3 mg, 0.521 mmol, 96% yield). H NMR (400 MHz, DMSO-$d_6$) δ 10.41 (s, 1H), 7.90-7.70 (m, 5H), 7.66-7.47 (m, 4H), 7.16 (dd, J=8.7, 2.1 Hz, 1H), 6.20 (d, J=15.7 Hz, 1H). $^{13}$C NMR (101 MHz, DMSO) δ 166.9, 140.4, 139.9, 139.3, 137.1, 135.4, 135.2, 133.0, 129.3, 128.9, 126.7, 123.4, 120.5, 120.3, 115.5. HRMS (m/z): calcd for $C_{17}H_{14}NO_4S_2$ ([M]$^+$+H) 360.0359; found 360.0357.

(E)-3-(5-(4-methylphenylsulfonamido)benzo[b]thiophen-2-yl)acrylic acid (KH-2A)

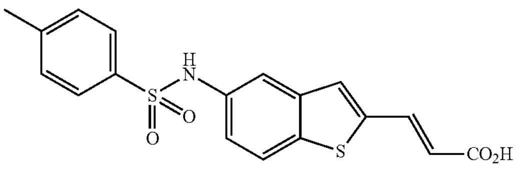 [SMILES: Cc1ccc(S(=O)(=O)Nc2ccc3sc(/C=C/C(=O)O)cc3c2)cc1]

Pale-yellow solid (106 mg, 0.284 mmol, 100% yield). $^1$H NMR (400 MHz, DMSO-$d_6$) δ 10.34 (s, br. 1H), 7.84-7.75 (m, 2H), 7.72 (s, 1H), 7.68-7.59 (m, 2H), 7.55 (d, J=2.2 Hz, 1H), 7.37-7.27 (m, 2H), 7.15 (dd, J=8.7, 2.2 Hz, 1H), 6.24-6.15 (m, 1H), 2.29 (s, 3H). $^{13}$C NMR (101 MHz, DMSO) δ 166.9, 143.3, 140.3, 139.9, 137.0, 136.5, 135.4, 135.2, 129.7, 128.9, 126.7, 123.4, 120.5, 120.1, 115.2, 21.0. HRMS (m/z): calcd for $C_{18}H_{16}NO_4S_2$ ([M]$^+$+H) 374.0515; found 374.0528.

(E)-3-(5-(4-(tert-butyl)phenylsulfonamido)benzo[b]thiophen-2-yl)acrylic acid (KH-3A)

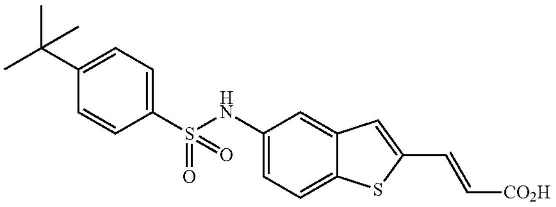 [SMILES: CC(C)(C)c1ccc(S(=O)(=O)Nc2ccc3sc(/C=C/C(=O)O)cc3c2)cc1]

Light-yellow solid (243 mg, 0.585 mmol, 91% yield). $^1$H NMR (400 MHz, DMSO-$d_6$) δ 10.42 (s, 1H), 7.84-7.73 (m, 2H), 7.73-7.66 (m, 3H), 7.59 (d, J=2.2 Hz, 1H), 7.56-7.50 (m, 2H), 7.19 (dd, J=8.7, 2.2 Hz, 1H), 6.20 (d, J=15.7 Hz, 1H), 1.21 (s, 9H). $^{13}$C NMR (101 MHz, DMSO) δ 166.9, 156.0, 140.3, 139.9, 137.1, 136.7, 135.4, 135.1, 128.9, 126.6, 126.2, 123.4, 120.5, 119.8, 114.8, 34.9, 30.7. HRMS (m/z): calcd for $C_{21}H_{22}NO_4S_2$ ([M]$^+$+H) 416.0985; found 416.1036.

(E)-3-(5-(2,4,6-trimethylphenylsulfonamido)benzo[b]thiophen-2-yl)acrylic acid (KH-4A)

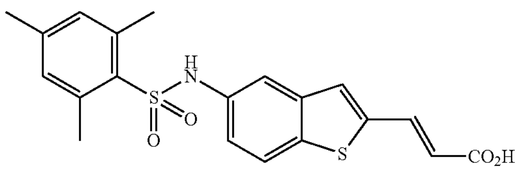 [SMILES: Cc1cc(C)c(S(=O)(=O)Nc2ccc3sc(/C=C/C(=O)O)cc3c2)c(C)c1]

Yellow solid (45.2 mg, 0.113 mmol, 36% yield). $^1$H NMR (400 MHz, DMSO-$d_6$) δ 12.44 (s, 1H), 10.27 (s, 1H), 7.84-7.73 (m, 2H), 7.71 (s, 1H), 7.44 (d, J=2.1 Hz, 1H), 7.09 (dd, J=8.7, 2.1 Hz, 1H), 6.96 (s, 2H), 6.20 (d, J=15.7 Hz, 1H), 2.56 (s, 6H), 2.17 (s, 3H). $^{13}$C NMR (101 MHz, DMSO) δ 166.8, 142.0, 140.3, 139.8, 138.7, 136.9, 135.1, 134.9, 133.6, 131.7, 128.8, 123.3, 120.4, 119.6, 114.5, 22.5, 20.3. HRMS (m/z): calcd for $C_{20}H_{20}NO_4S_2$ ([M]$^+$+H) 402.0828; found 402.0874.

HuR Inhibitory Activity Via a Fluorescence Polarization (FP) Assay

Figure 3:
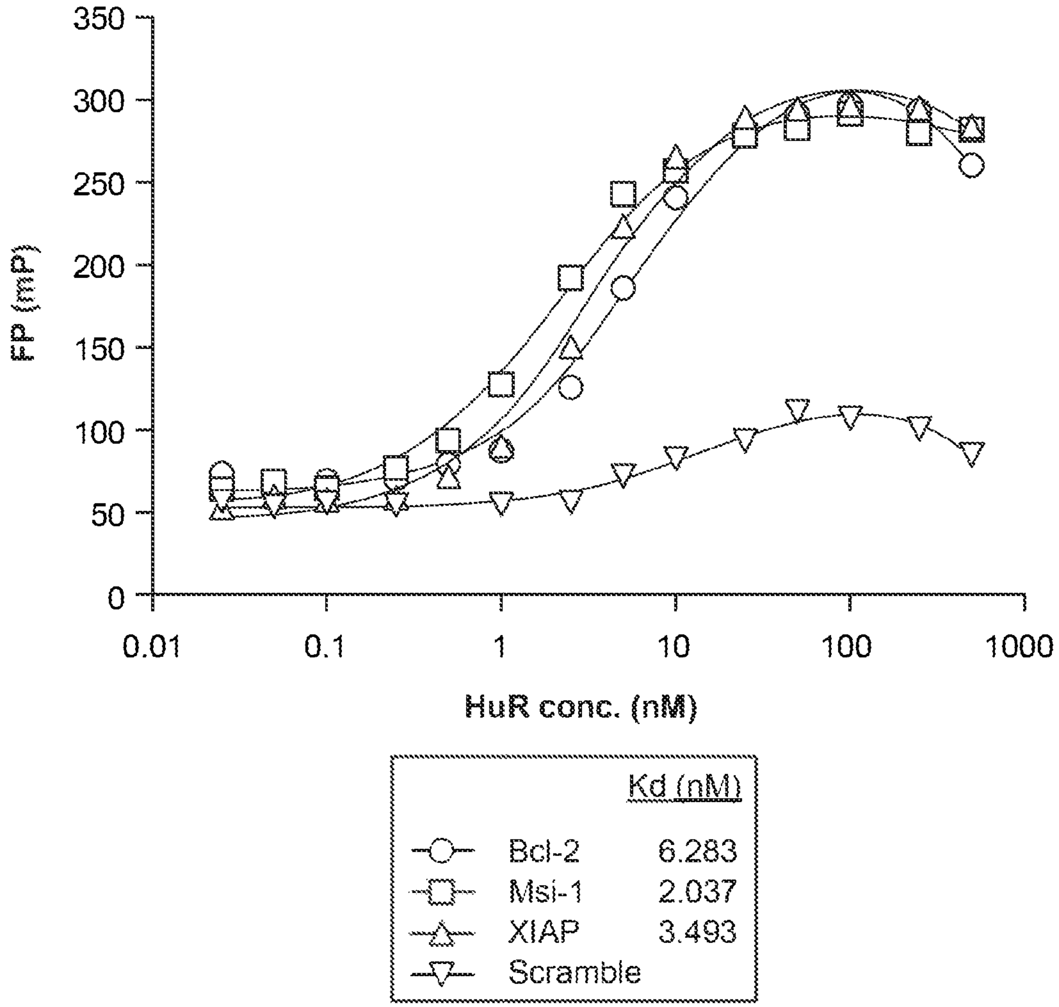
FIG. 3 provides the results of a fluorescence polarization (FP)-based binding assay, illustrating that full length HuR binds to FITC-Bcl-2, Msi1, and XIAP RNA but not to scrambled oligo-FITC, according to the working examples. The concentration of FITC-RNA used in the assay is 2 nM.

A fluorescence polarization (FP)-based binding assay was utilized to assess the inhibition of HuR protein interaction with the ARE site of Msi1 mRNA ("HuR-Msi1$^{ARE}$") by compounds of interest. Briefly, full-length human HuR protein was produced by the KU COBRE-PSF Protein Purification Group and Bcl2, Msi1 and XIAP mRNA sequences (16 nt) were designed based on literature precedent[23,24,31,32]. Fluorescein labeled RNAs were purchased from Dharmacon with the following sequences: Msi1 RNA: 5'-GCUUUUAUUUAUUUUG-3'-fluorescein; Bcl-2 RNA: 5'-AAAAGAUUUAUUUAUU-3'-fluorescein; XIAP RNA: 5'-UAGUUAUUUUUA UGUC-3'-fluorescein, and a 16-nt degenerative RNA with 3'-fluorescein label was used as a negative control. FIG. 3 provides the results of these experiments, illustrating HuR binding with the above fluorescein-labeled target RNAs, with a Kd of 6.3, 2.0 and 3.5 nM for Bcl2, Msi1 and XIAP RNA oligos, respectively.

The cytotoxicity of the tested compounds in several cancer cell lines (HCT116 β/w, MIAPaCa-2, and MDA-MB-231) was determined by a cytotoxicity assay, where the results are provided in Table 1. Cells were seeded in 96-well culture plates (5,000 cells/well) and treated with titrated compounds in triplicate. After 96 h incubation, cell growth medium was removed and proliferation reagent WST-8 (Sigma) was added to each well and incubated at 37° C. for 1-3 h. Absorbance was then measured with a plate reader at 450 nm with correction at 650 nm. The results were expressed as the percentage of absorbance of treated wells versus that of vehicle control. $IC_{50}$, the drug concentration causing 50% growth inhibition, was calculated via sigmoid curve fitting using GraphPad Prism 5.0.

TABLE 1

Chemical structure, HuR inhibitory activity in FP assay, and cytotoxicity assays

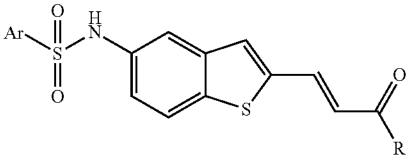

| ID | Ar | R | Ki via FP assay (μM) | Cytotoxicity ($IC_{50}$, μM) HCT116 β/w | MIAPaCa-2 | MDA-MB-231 |
|---|---|---|---|---|---|---|
| KH-1 | 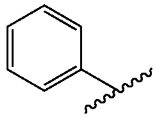 [SMILES: *c1ccccc1] | 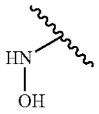 | 9.20 | 0.86 | 1.21 | 0.98 |
| KH-2 | 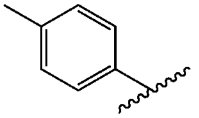 [SMILES: *c1ccc(C)cc1] | 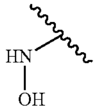 | 5.55 | 1.42 | 2.33 | 1.46 |
| KH-3 | 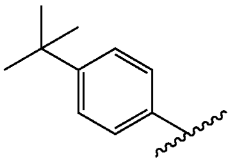 [SMILES: *c1ccc(C(C)(C)C)cc1] | 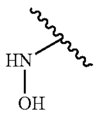 | 0.81 | 3.60 | 4.50 | 4.15 |
| KH-4 | 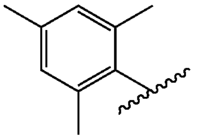 | 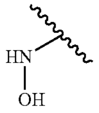 | 1.41 | 1.20 | 2.34 | 1.04 |
| KH-1A | 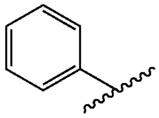 [SMILES: *c1ccccc1] | 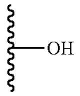 [SMILES: *O] | 5.82 | >100 | >100 | >100 |
| KH-2A | 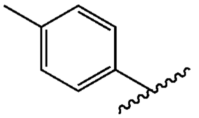 [SMILES: *c1ccc(C)cc1] | 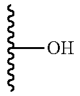 | 2.92 | >100 | >100 | >100 |
| KH-3A | 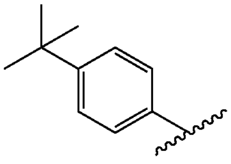 [SMILES: *c1ccc(C(C)(C)C)cc1] | 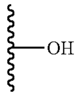 | 1.38 | >100 | >100 | >100 |

TABLE 1-continued

Chemical structure, HuR inhibitory activity in FP assay, and cytotoxicity assays

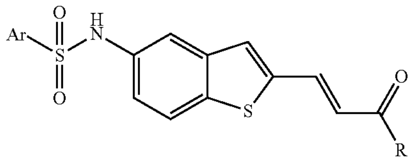

| ID | Ar | R | Ki via FP assay (μM) | Cytotoxicity ($IC_{50}$, μM) HCT116 β/w | MIAPaCa-2 | MDA-MB-231 |
|---|---|---|---|---|---|---|
| KH-4A | 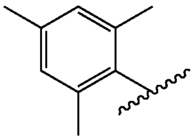 | 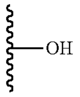 | 2.92 | >100 | >100 | >100 |
| KH-1B | 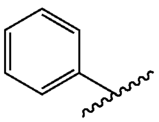 [SMILES: *c1ccccc1] | 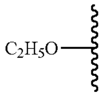 | >20 | 35.55 | 37.62 | 41.77 |
| KH-2B | 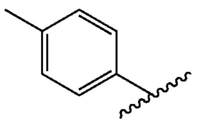 | 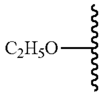 | >20 | 40.12 | 39.52 | 43.00 |
| KH-3B | 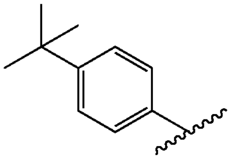 [SMILES: *c1ccc(C(C)(C)C)cc1] | 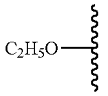 | >20 | 68.18 | 45.45 | 45.58 |
| KH-4B | 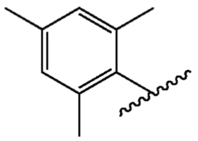 | 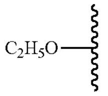 | >20 | 91.43 | 30.44 | >100 |

Figure 4A:
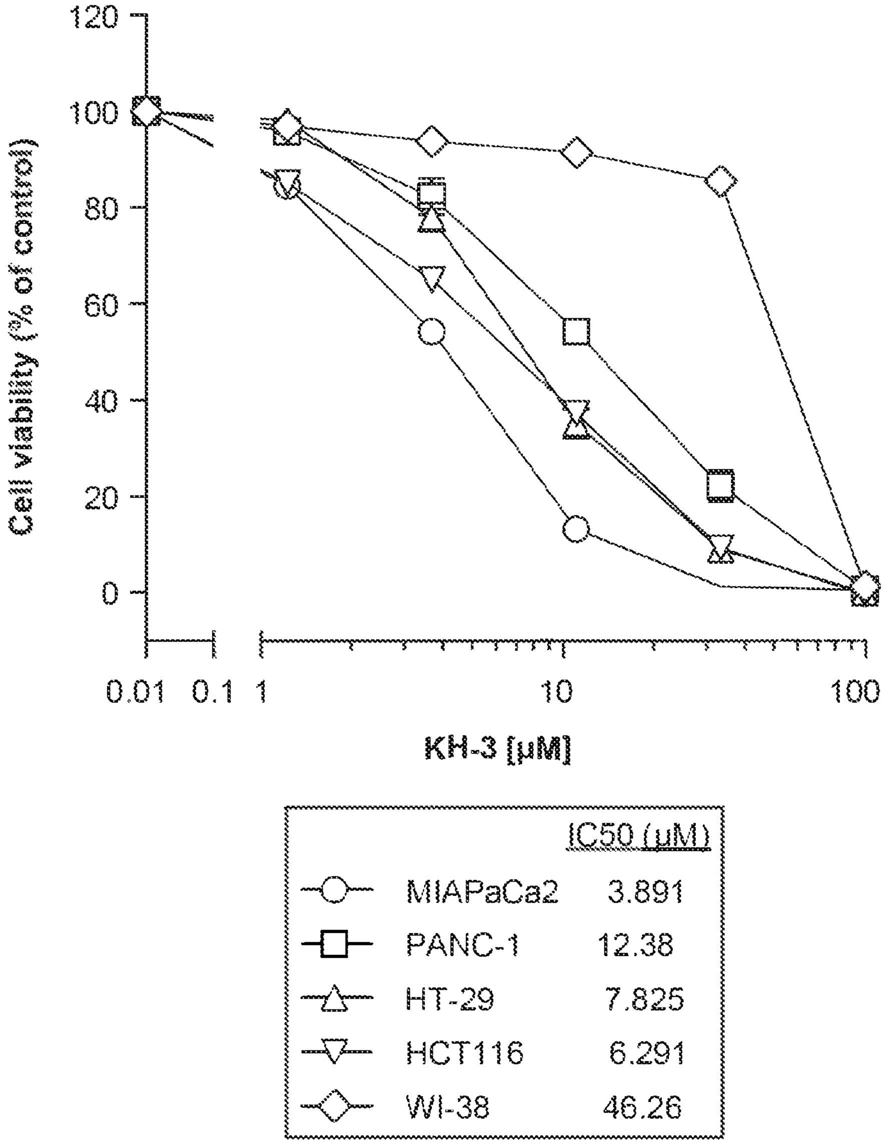
FIGS. 4A-4C illustrate the results of cytotoxicity assays performed using KH-3 against a panel of cell lines (including normal cell line WI-38), showing KH-3 exhibits potent cytotoxicity across the panel of cancer cell lines but is not cytotoxic against normal cell line WI-38 until about 100 μM, according to the working examples.
Figure 4B:
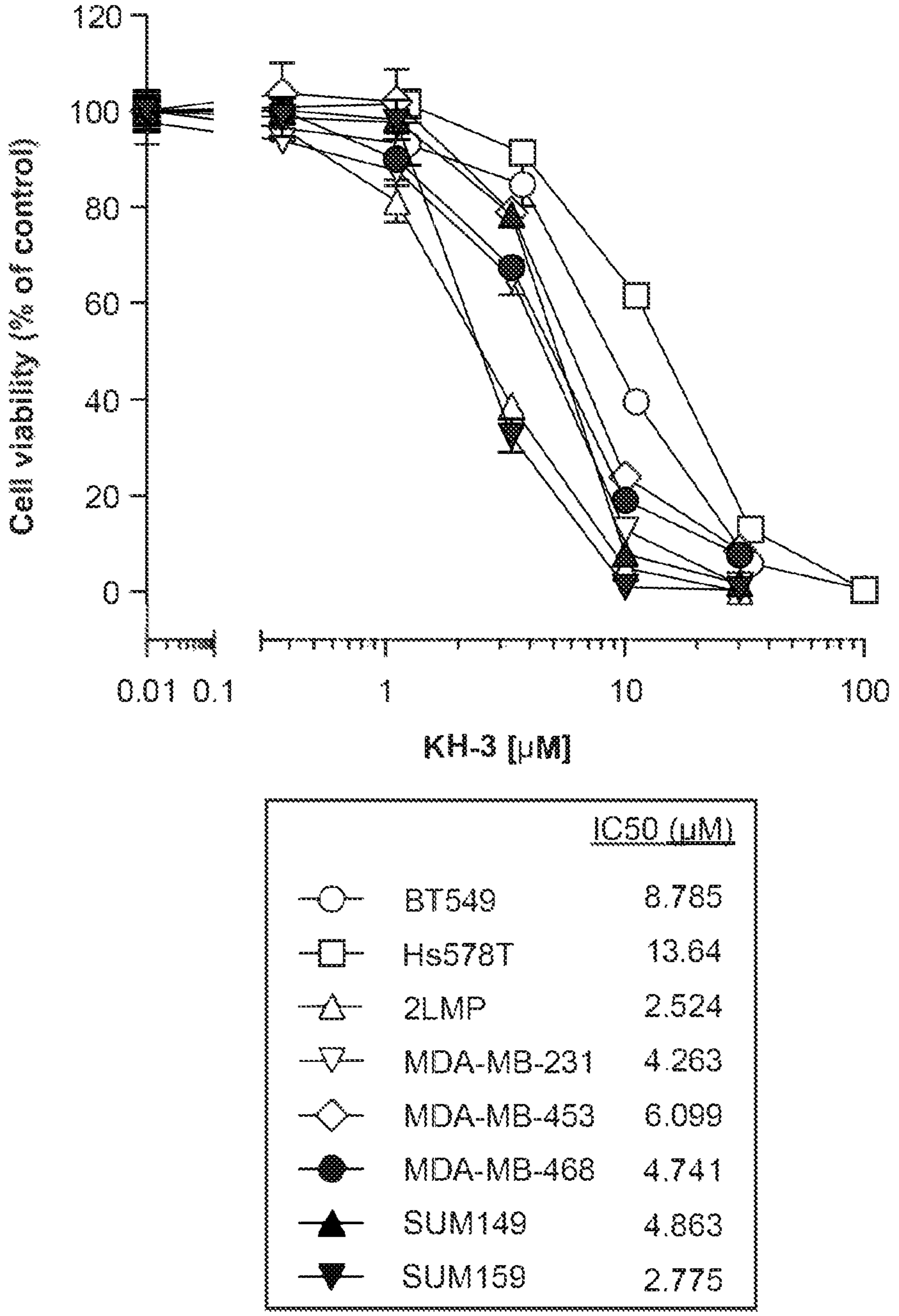
Figure 4C:
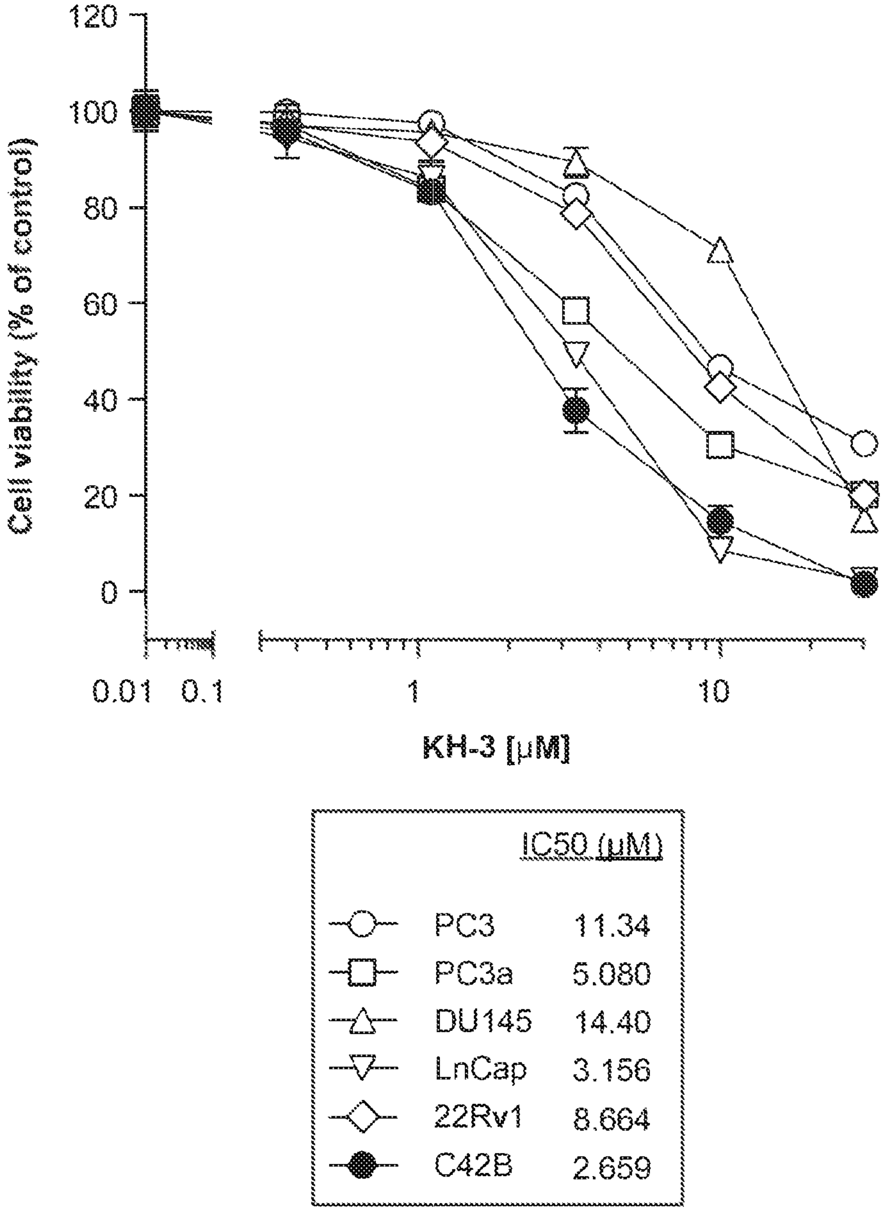

The assay was then utilized to assess cytotoxicity of KH-3 against an expanded panel of cell lines (including normal cell line WI-38), where FIGS. 4A-4C provide the results. As illustrated by FIGS. 4A-4C, KH-3 exhibits potent cytotoxicity across a panel of cancer cell lines but is not cytotoxic against normal cell line WI-38 until about 100 μM.

Surface Plasmon Resonance ("SPR") Validation

Figure 5:
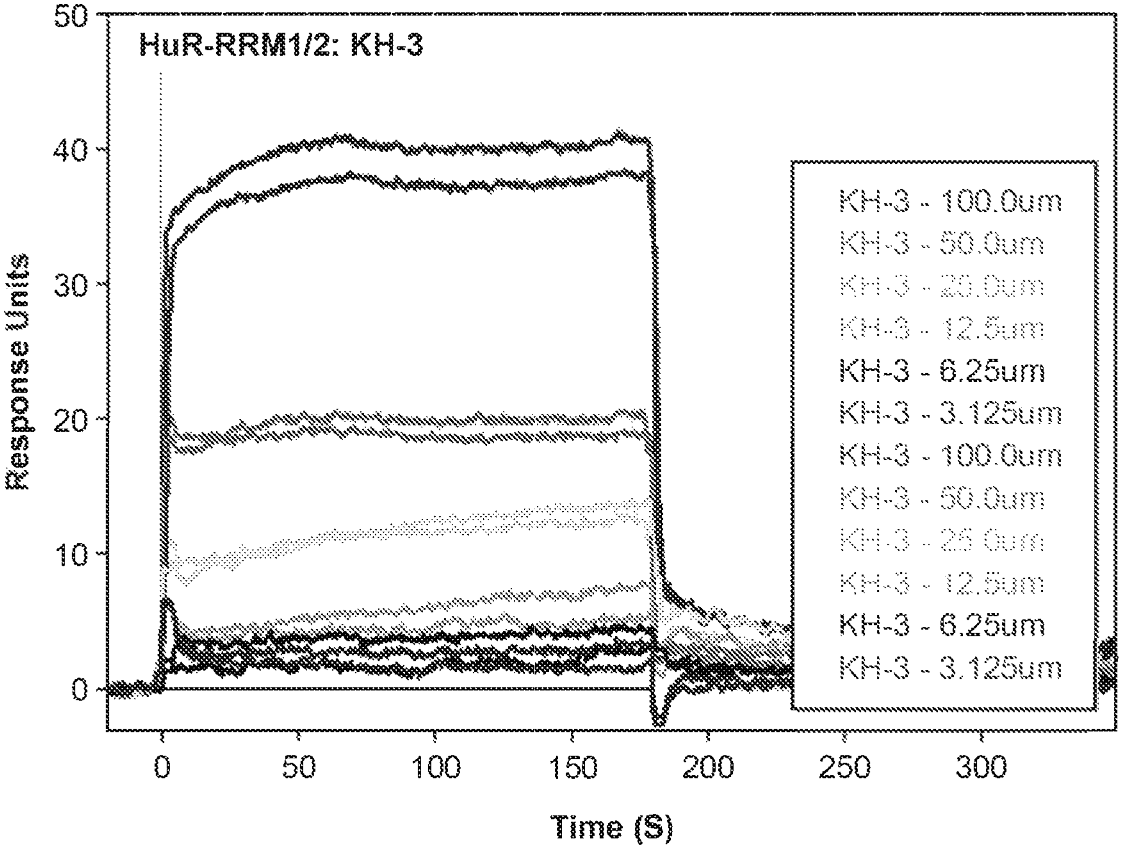
FIG. 5 provides the results of surface plasmon resonance analyses of the binding of KH-3 to immobilized HuR RRM1/2, according to the working examples.

A BiaCore 3000 instrument was used to further validate certain findings from the FP assay and will be used on other compounds of the present technology. BiaCore 3000 is a SPR)-based, high performance research system available for label free studies of biomolecule interactions in real time. Thus, such studies provide both equilibrium data and kinetic parameters of queried interactions. Both the full length HuR protein as well as its fragments RRM1 and RRM1/2 were immobilized in separate chambers on a Biacore sensor chip CM5, and then compounds of interest (such as compounds of the present technology) are injected at a series of concentrations as soluble analytes. Curves are determined from the experimentally observed curves by successive subtractions of signals obtained for the reference surface and signals for the running buffer injected under the same conditions as the compounds of interest. FIG. 5 provides the curves for the indicated concentrations of KH-3 to HuR RRM1/2. The data provides the association/dissociation characteristics of specific interactions of compounds of interest with HuR and its fragments.

Inhibition of Endogenous HuR-mRNA Interaction of HuR-Inhibitors

Two pull-down assays were further used to illustrate the inhibition of the HuR-mRNA interaction by compounds of the present technology.

Figure 6A:
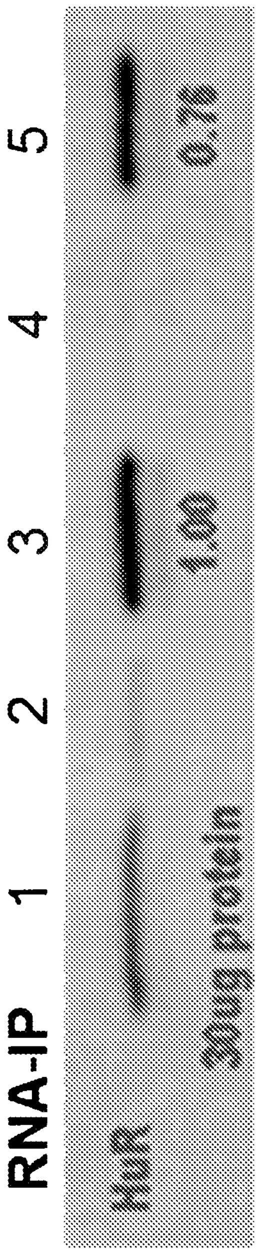
FIGS. 6A-6C provides the results of pull-down assays with certain compounds of the present technology evidencing partial blocking of endogenous HuR-mRNA interaction, according to the working examples.

Pull-Down Assay #1—RNA Immunoprecipitation: Cells with HuR overexpression were treated with compounds, then the cell cytoplasmic lysates were collected using NE-PER Nuclear and Cytoplasmic Extraction Kit (Thermo Scientific), and subsequently to the cell cytoplasmic lysates were added the biotinylated target ARE oligo from Msi1 mRNA (Msi1-Bi). Following this, streptavidin beads were added to pull down HuR protein bound to Msi1-Bi. Compounds of the present technology blocked the HuR pull-down by the biotinylated ARE oligo, illustrating inhibition of the Hur-mRNA interaction. Unlabeled target AREs were used as positive control. FIG. 6A provides results with KH-3, illustrating KH-3 blocked Msi1-Bi RNA mediated pull-down of HuR protein up to 24%.

Figure 6B:
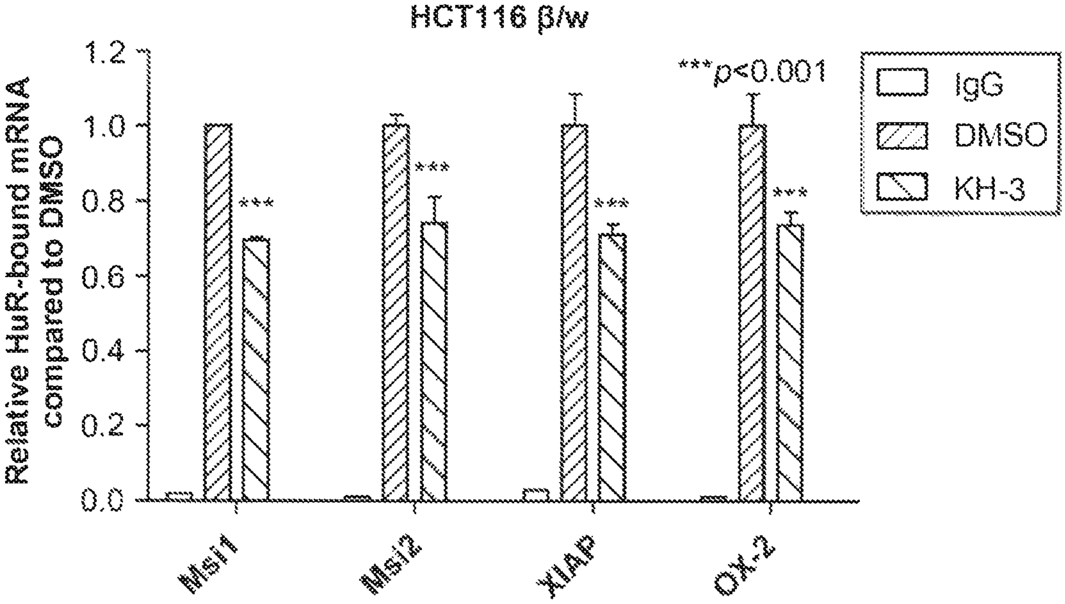
Figure 6C:
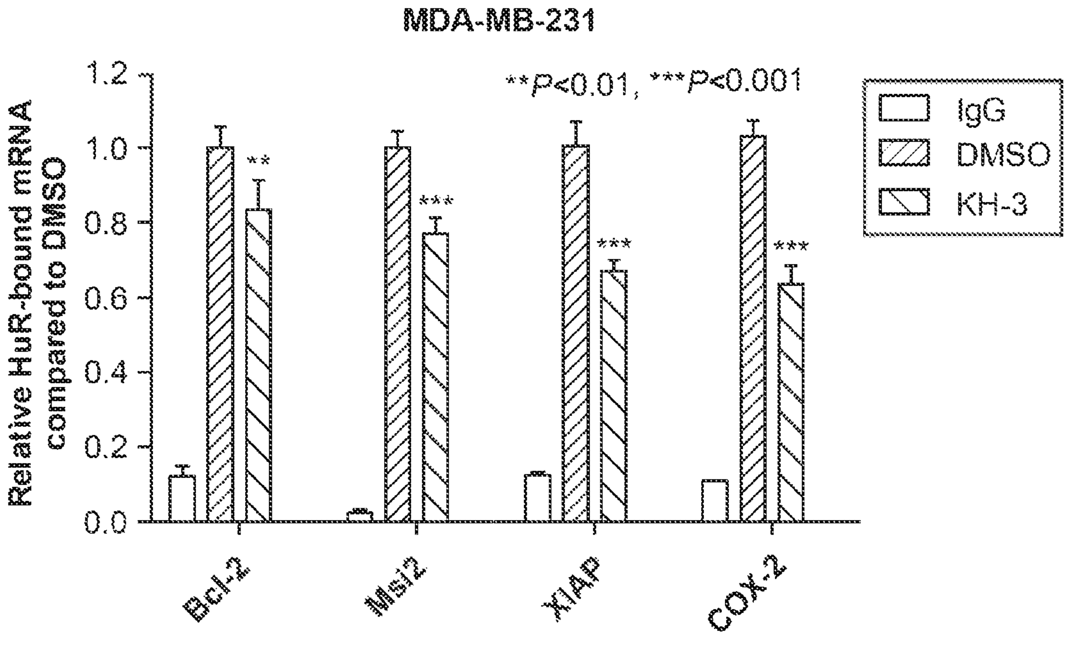

Pull-Down Assay #2—Ribonucleoprotein Immunoprecipitation: Cells with HuR overexpression were treated with compounds, then the cell cytoplasmic lysates were collected using NE-PER Nuclear and Cytoplasmic Extraction Kit (Thermo Scientific), and subsequently then the cell cytoplasmic lysates were incubated with anti-HuR antibody, and then Protein G agarose beads (from Roche) were added to pull down HuR protein. The HuR-bound target mRNAs pulled down were measured by qRT-PCR using a reported method (Ji, Q., et al., *MicroRNA miR-*34 *inhibits human pancreatic cancer tumor-initiating cells*. PLoS One, 2009. 4(8): p. e6816, incorporated herein by reference). Compounds of the present technology blocked the target mRNAs pulled down by HuR antibody. Mouse IgG was used as negative control. Utilizing KH-3 in this assay, it was shown that KH-3 partially blocks HuR pull-down of target mRNAs in HCT-116 β/w cells (FIG. 6B) and MDA-MB-231 cells (FIG. 6C).

Inhibition of HuR Target mRNA Stability and Protein Levels of HuR-Inhibitors

Figure 7A:
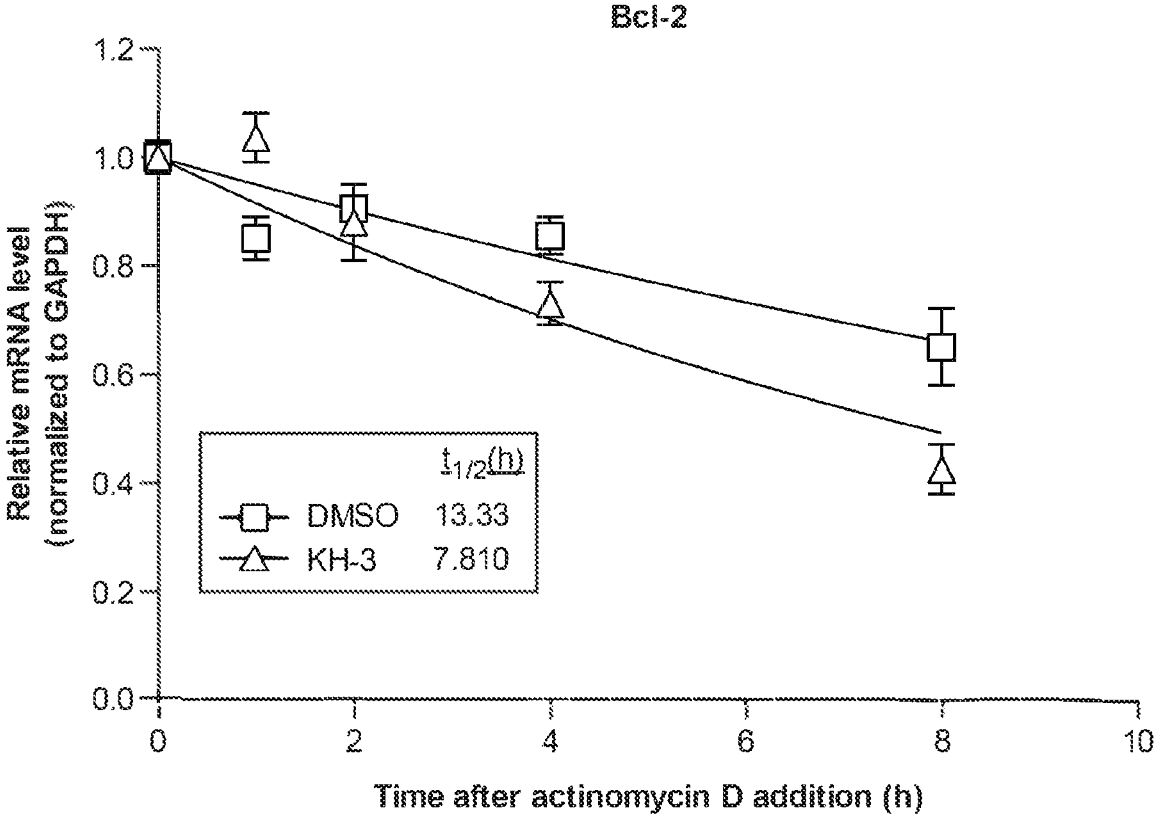
FIGS. 7A-7D illustrate that a compound of the present technology, KH-3, decreases the stability of HuR target mRNAs, namely Bcl-2 (FIG. 7A), XIAP (FIG. 7B), Msi1 (FIG. 7C), and HuR mRNA (FIG. 7D) where HCT-116 β/w cells were co-treated with 10 mM KH-3 or DMSO and 5 mg/ml Actinomycin D at the indicated time points, according to the working examples. HuR target mRNA levels were measured by qRT-PCR.
Figure 7B:
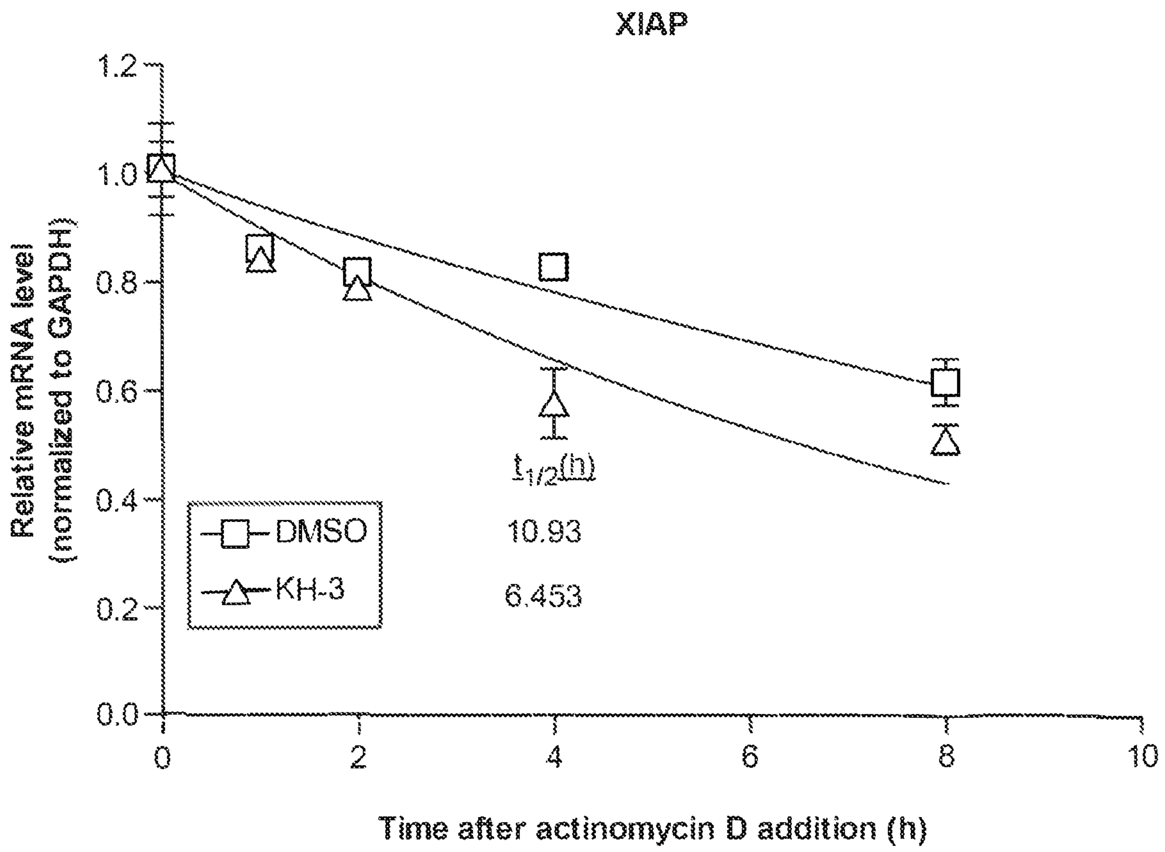
Figure 7C:
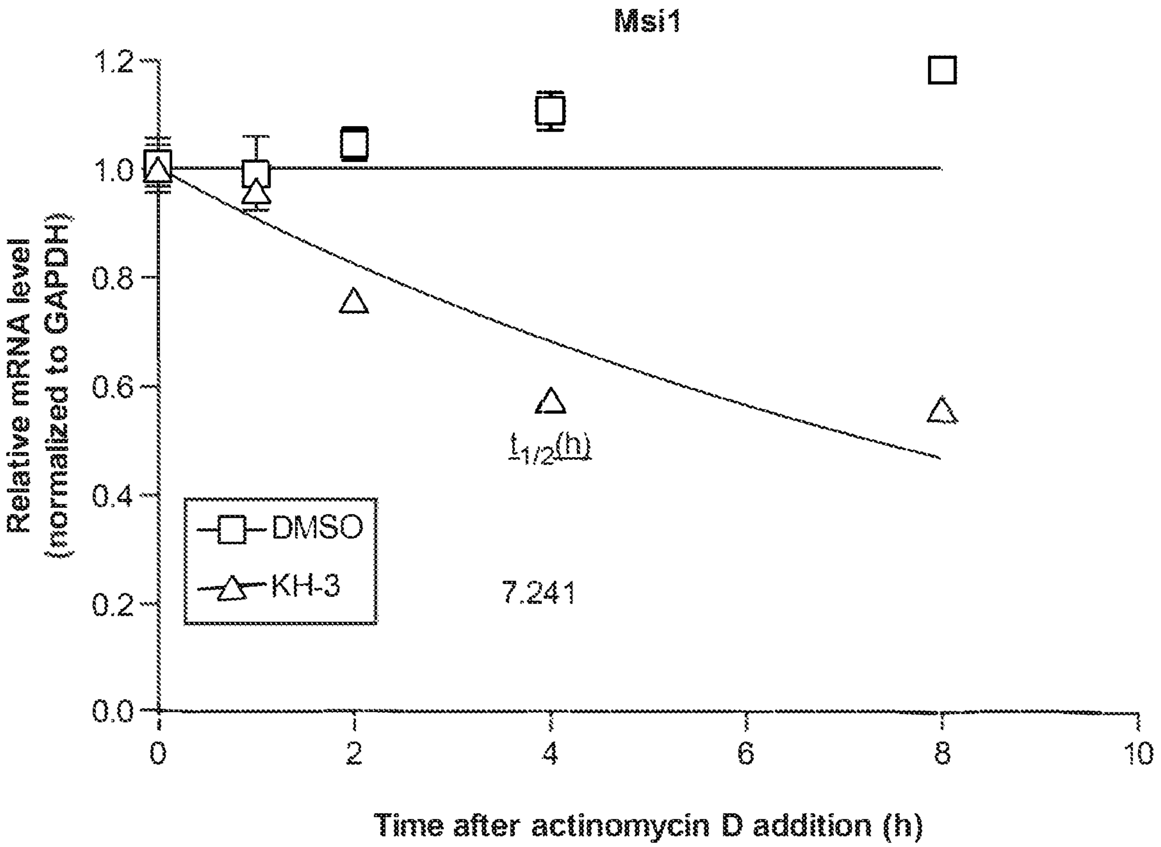
Figure 7D:
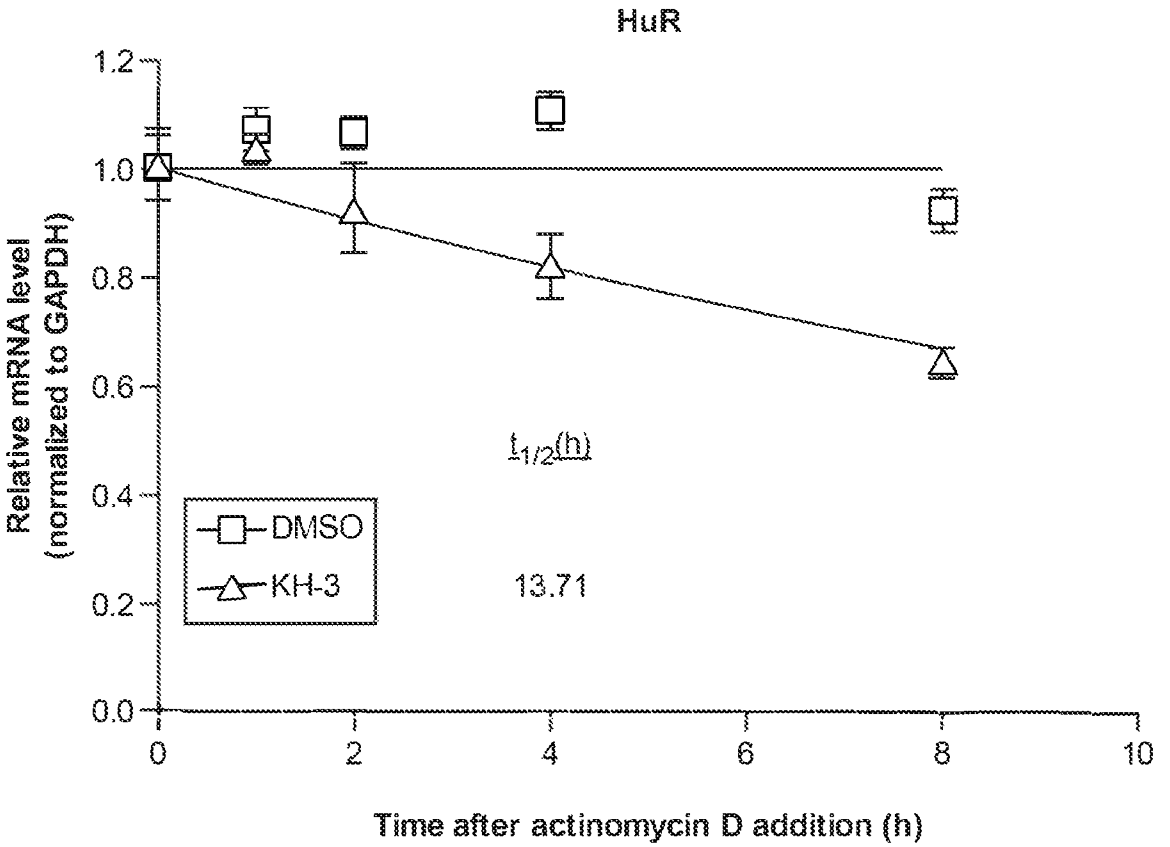
Figure 8A:
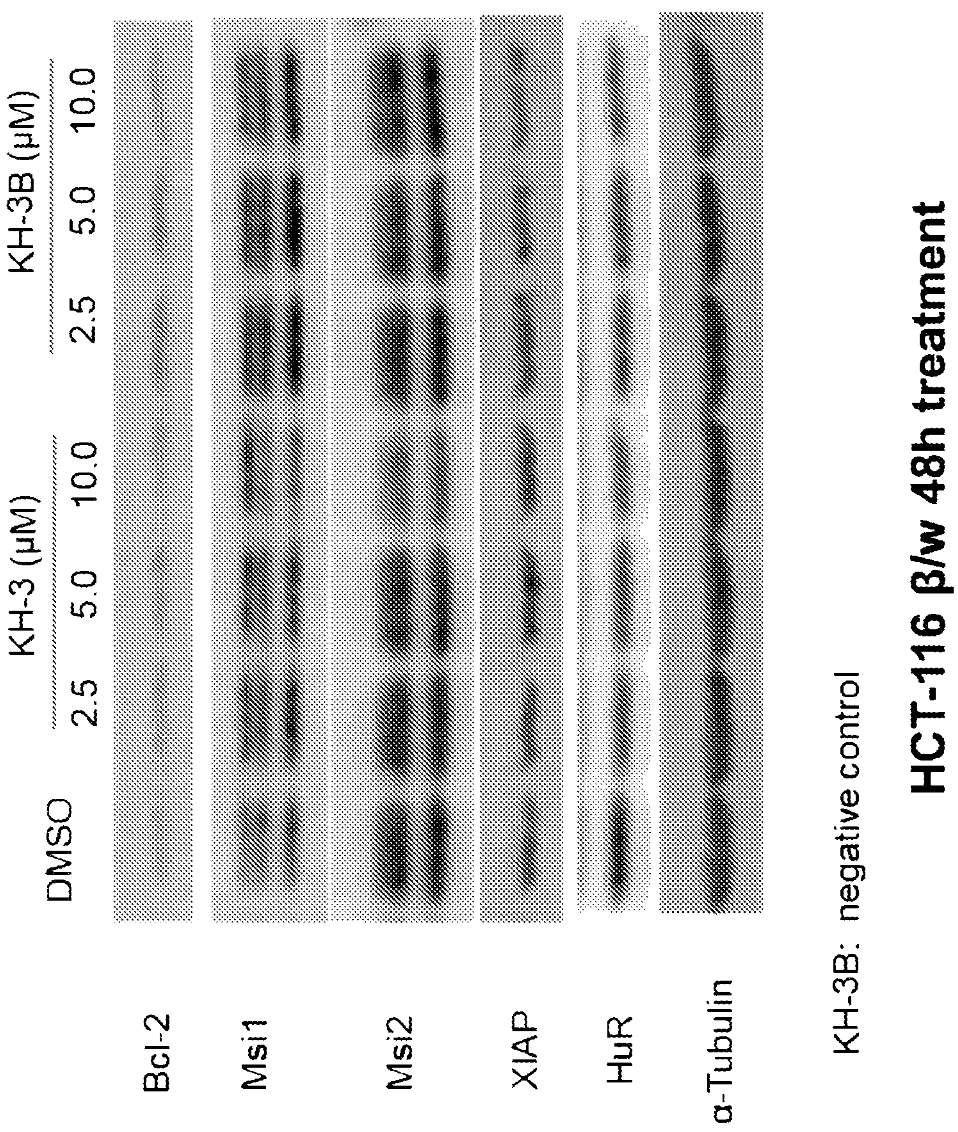
FIGS. 8A-8C provide the results of Western blot analysis illustrating that KH-3 decreases the protein levels of HuR targets in HCT-116 β/w cells (FIG. 8A) and MDA-MB-231 cells (FIG. 8B) and is involved in cell death mechanisms by inducing PARP cleavage, LC3 conversion, and RIP3 activation (FIG. 8C), according to the working examples.
Figure 8B:
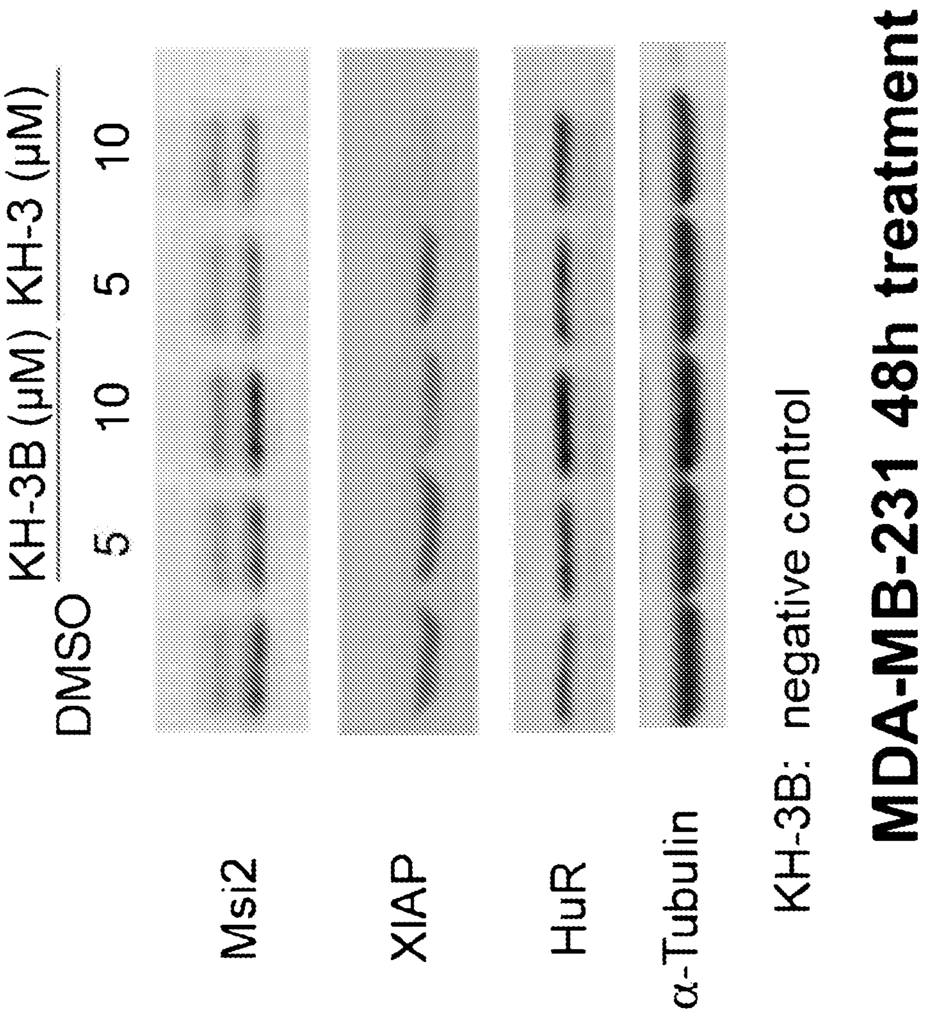
Figure 8C:
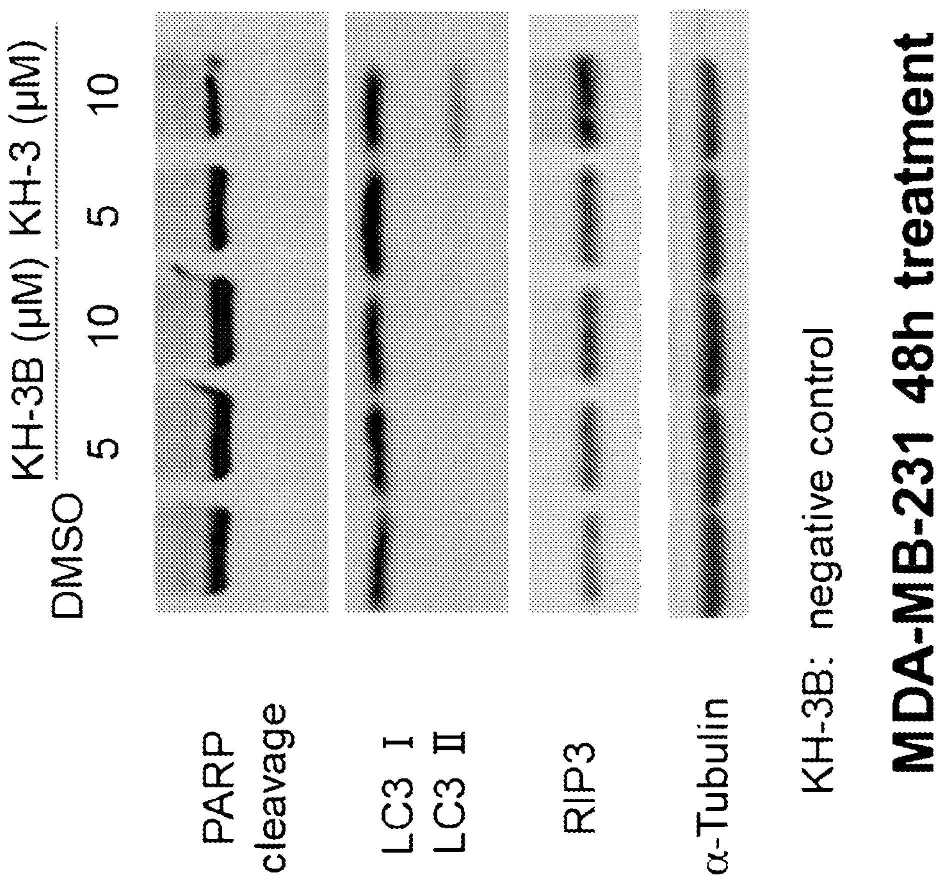

As HuR promotes stability of its target mRNAs, it is expected that HuR-inhibitors will block HuR function and shorten the half-life ($t_{1/2}$) of target mRNAs. mRNA stability was determined via quantitative real-time PCR (qRT-PCR) after co-treatment of compounds of the present technology and Actinomycin D (a transcription inhibitor). FIGS. 6A-6D shows that KH-3 decreases the stability of HuR targets Bcl-2 mRNA (FIG. 7A), XIAP mRNA (FIG. 7B), and Msi1 mRNA (FIG. 7C) and HuR mRNA (FIG. 7D). Because HuR also increases the translation of target mRNAs, the effect of compounds of the present technology was tested on protein levels of HuR targets by Western blot analysis. FIGS. 8A-8C show that KH-3 decreased the protein levels of HuR targets in HCT-116 β/w cells (FIG. 8A) and MDA-MB-231 cells (FIG. 8B) and also induced cell death through apoptosis, autophagy and necroptosis by inducing PARP cleavage, LC3 conversion, and RIP3 activation, respectively (FIG. 8C). Notably, these properties were not exhibited by negative control KH-3B.

Inhibition of Cancer Cell Metastasis

Figure 9:
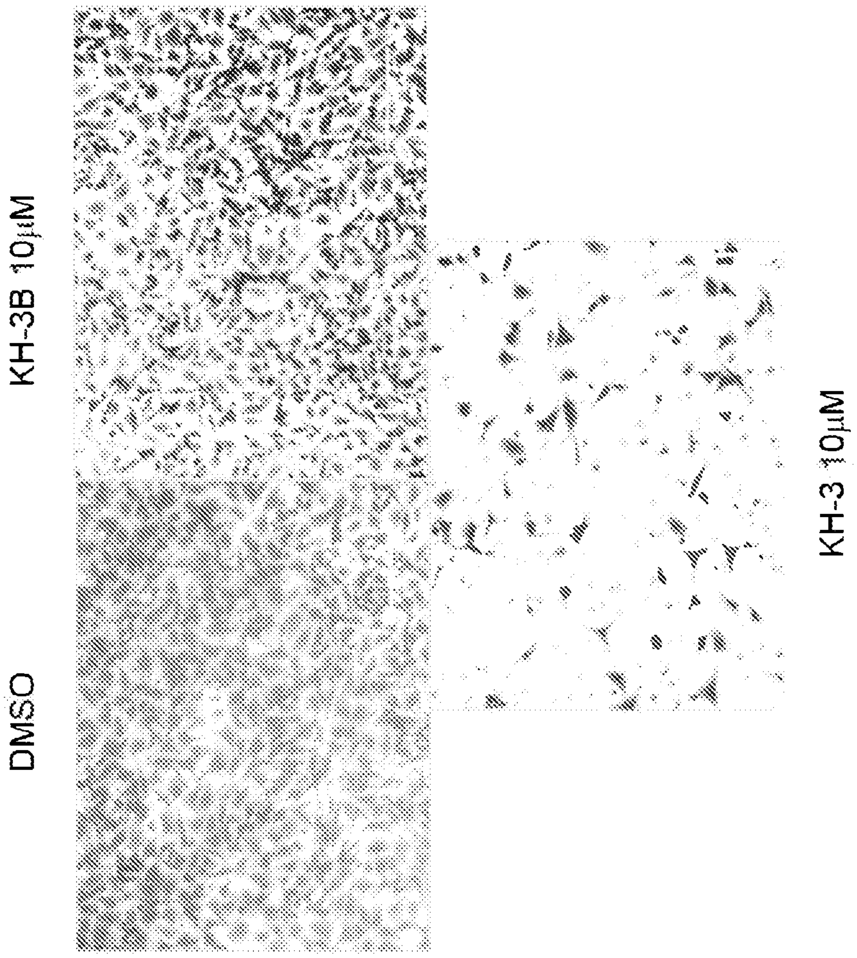
FIG. 9 provide the results of anti-metastatic experiments on MDA-MB-231 cells with a compound of the present technology (KH-3) versus DMSO as well as negative control compound KH-3B, according to the working examples.

To examine the anti-metastatic effect of compounds of the present technology, an invasion assay using Matrigel Invasion Chambers coated with Matrigel Matrix was performed. To perform the assays, MDA-MB-231 cells (a triple negative breast cancer cell line) pretreated with compounds for 24 hours are added to the chambers and then incubated for 20 hours. Cells that remained on the upper surface of the chamber are completely removed with a cotton swab. Cells that emigrated or invaded through the membrane/Matrigel to the bottom of the chamber were fixed and stained with 0.2% crystal violet and photographed. FIG. 9 illustrates the results of these experiments with KH-3, illustrating that KH-3 inhibited MDA-MB-231 cell invasion while negative control KH-3B did not.

Overcoming Chemo-Resistance

Figure 10A:
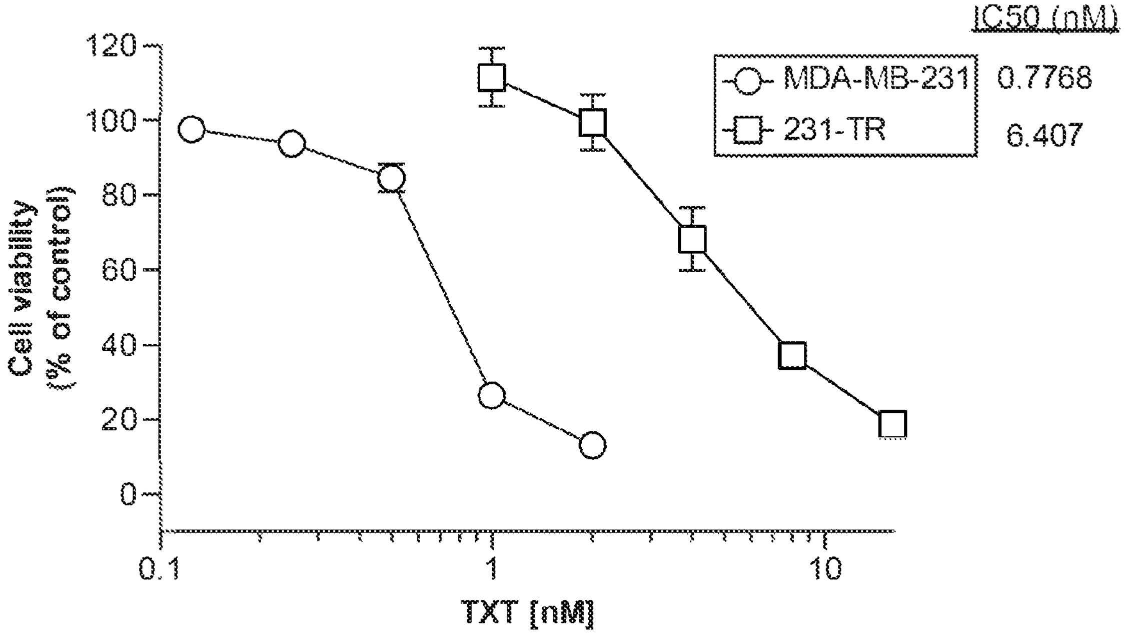
FIGS. 10A-10E illustrate use of compounds of the present technology to overcome acquired docetaxel and doxorubicin resistance in MDA-MB-231 cells, according to the working examples.
Figure 10B:
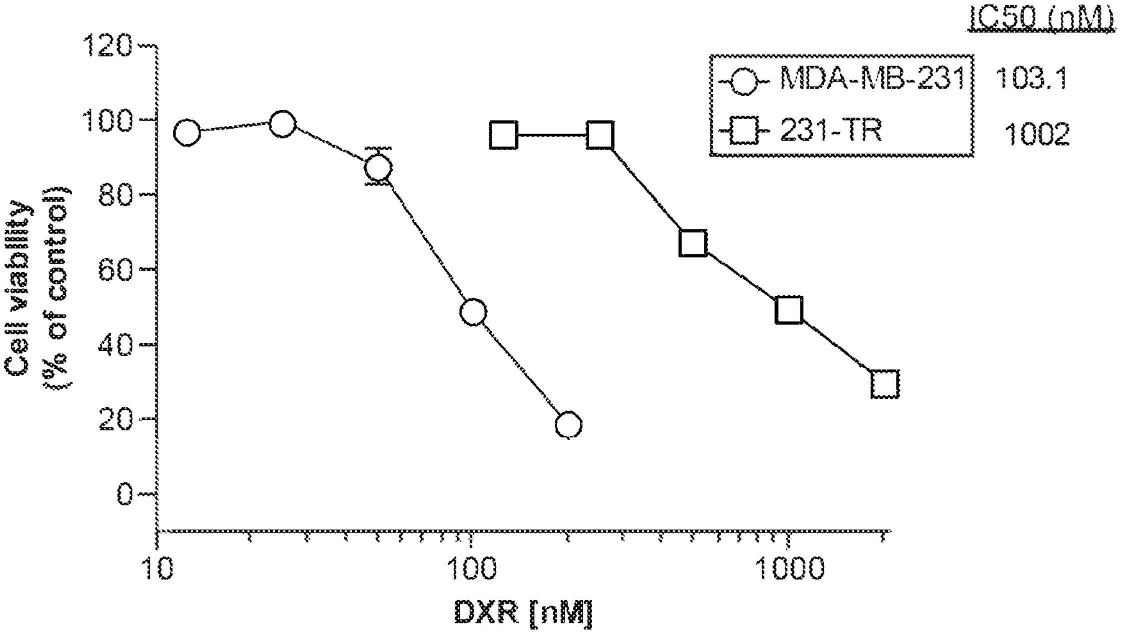
Figure 10C:
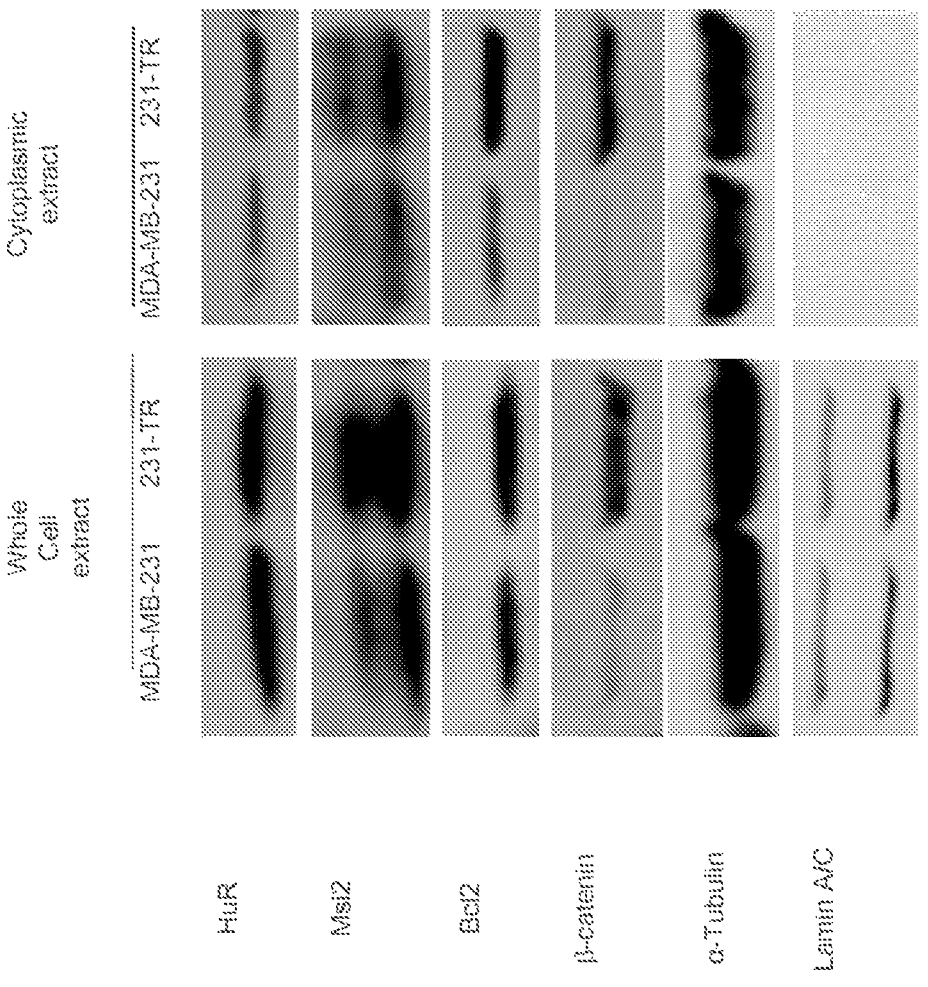
Figure 10D:
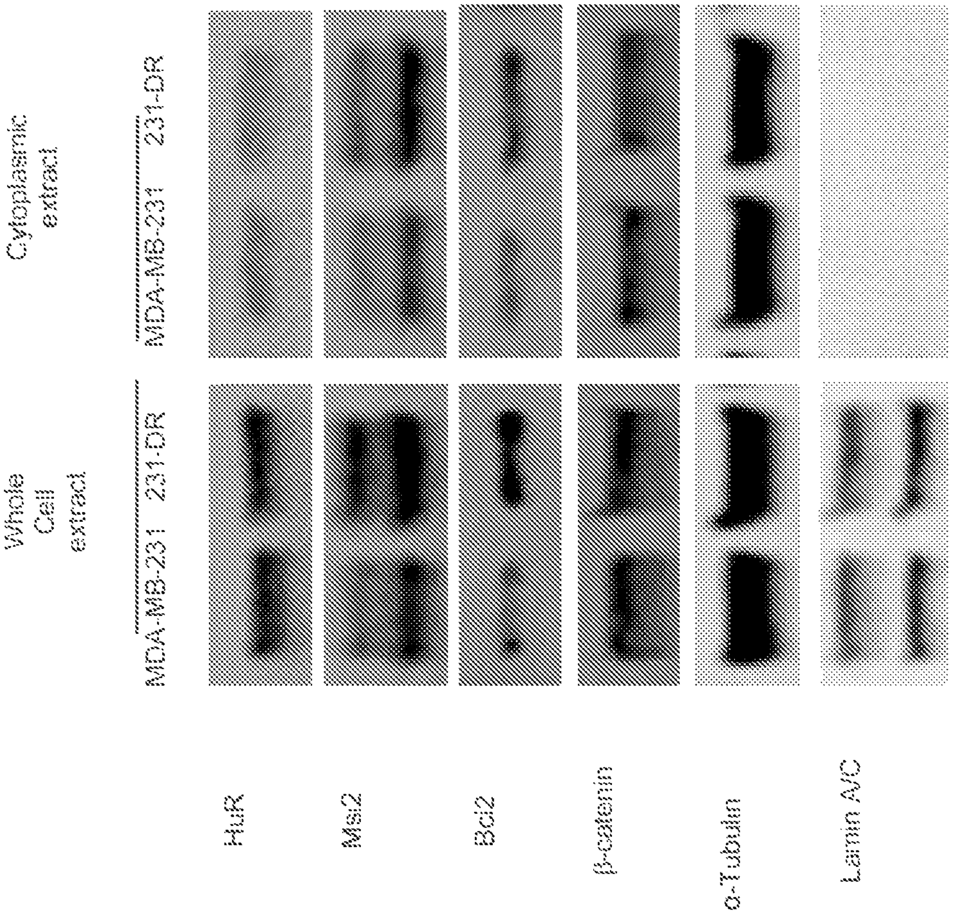
Figure 10E:
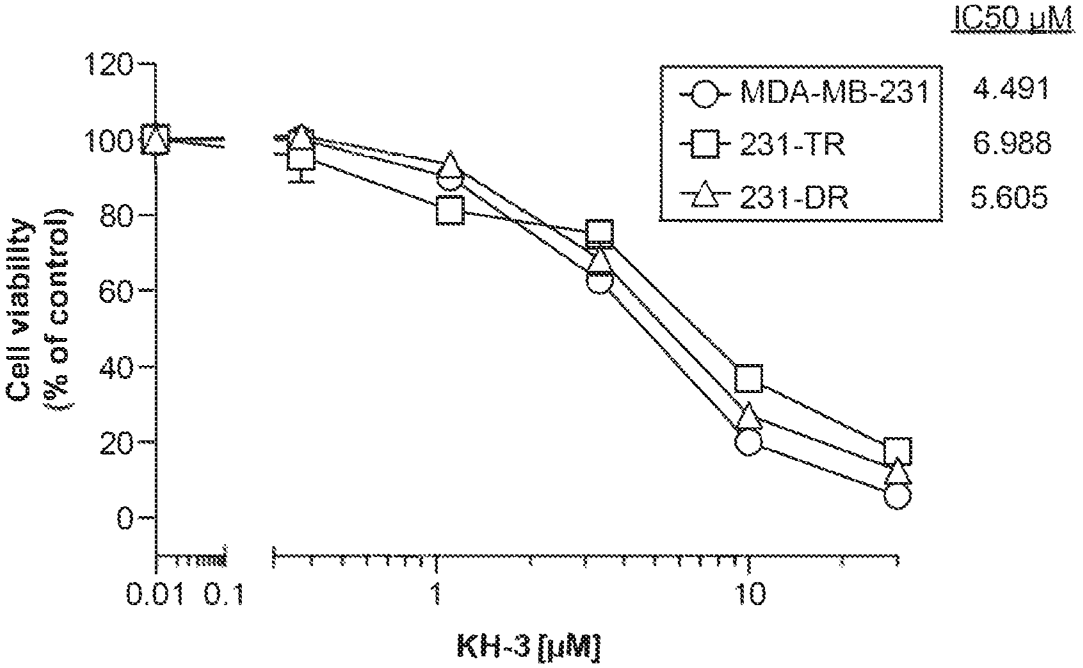

To further mimic clinical conditions and assess overcoming acquired chemo-resistance via compounds of the present technology, docetaxel-resistant and doxorubicin-resistant MDA-MB-231 cells were generated by continuous exposure of cells to increasing concentrations of docetaxel (TXT) or doxorubicin (DXR). Cytotoxicity assays were then performed to assess the chemo-resistance of the produced cell lines as well as assess the sensitivity of such chemo-resistant cell lines to compounds of the present technology. The results of such assays are provided in FIGS. 10A-10B and 10E. The docetaxel-resistant cell line (231-TR) that was produced exhibited more than 8-fold higher $IC_{50}$ against docetaxel compared to parental cell line (FIG. 10A). The doxorubicin-resistant cell line (231-DR) that was produced exhibited about 10-fold higher $IC_{50}$ against doxorubicin compared to parental cell line (FIG. 10B). Western blot analysis of these resistant cell lines (FIGS. 10C-10D) illustrate both resistant cell lines have increased cytoplasmic HuR as well as HuR target encoding proteins compared to the respective parental cell line, thus indicating that HuR is involved in the resistance. Significantly, both resistant cell lines display similar sensitivity to KH-3 compared to the parental cell line (FIG. 10E), which demonstrates that HuR inhibition according to the present technology overcomes acquired docetaxel and doxorubicin resistance.

Figure 11A:
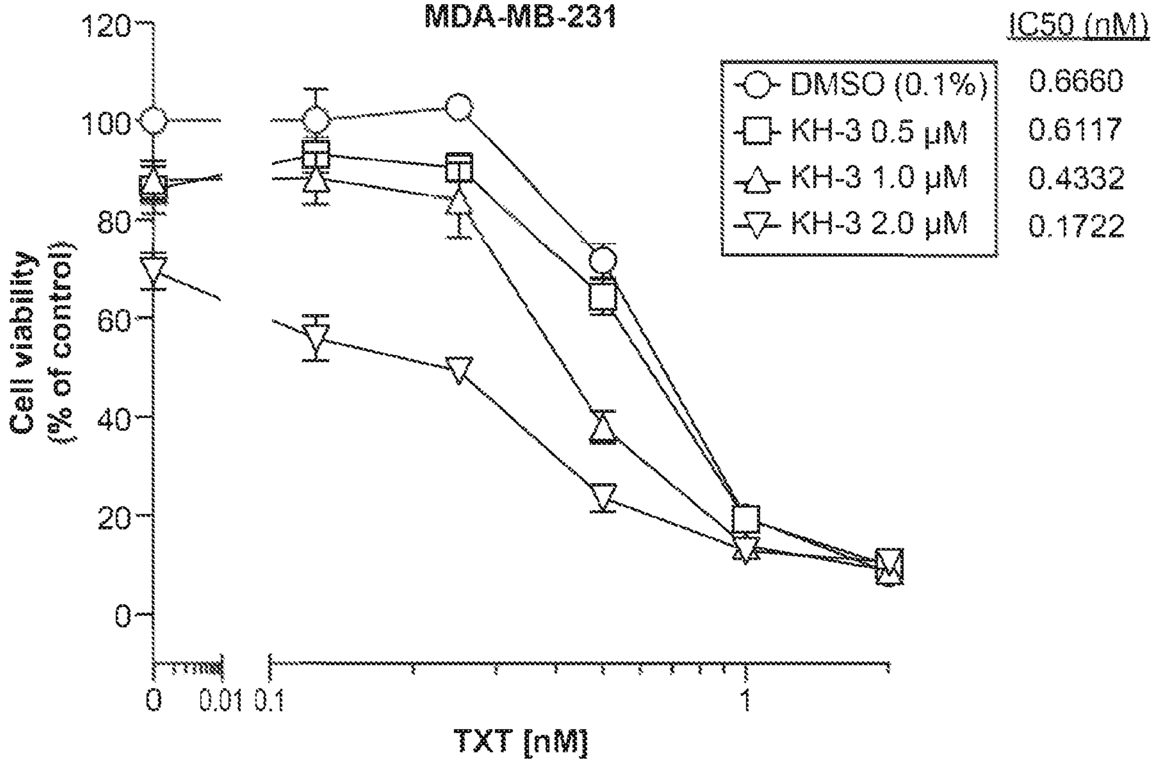
FIGS. 11A-11D provides the results of cytotoxicity assays performed utilizing concentrations of KH-3 that were below the lethal threshold for KH-3 (a "sub-lethal concentration") in combination with docetaxel against MDA-MB-231 cells (FIG. 11A) and against 231-TR cells (FIG. 11B) or (ii) in combination with doxorubicin against MDA-MB-231 cells (FIG. 11C) and against 231-DR cells (FIG. 11D), according to the working examples.
Figure 11B:
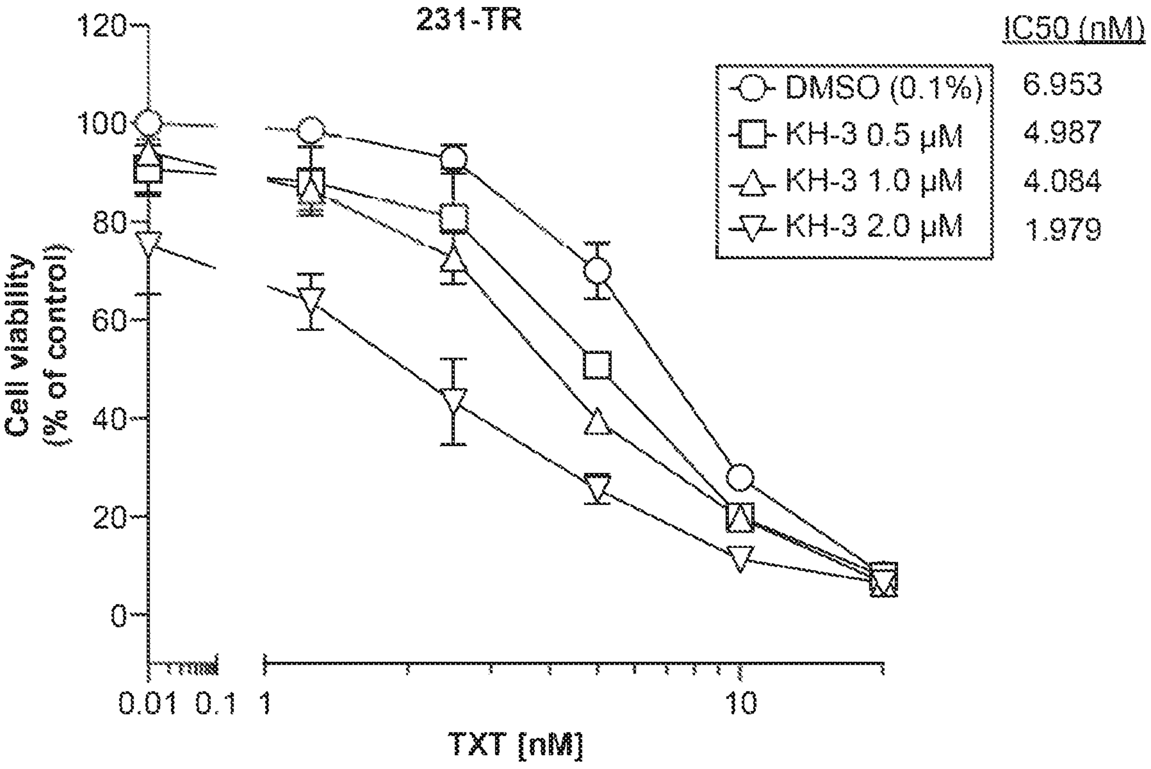
Figure 11C:
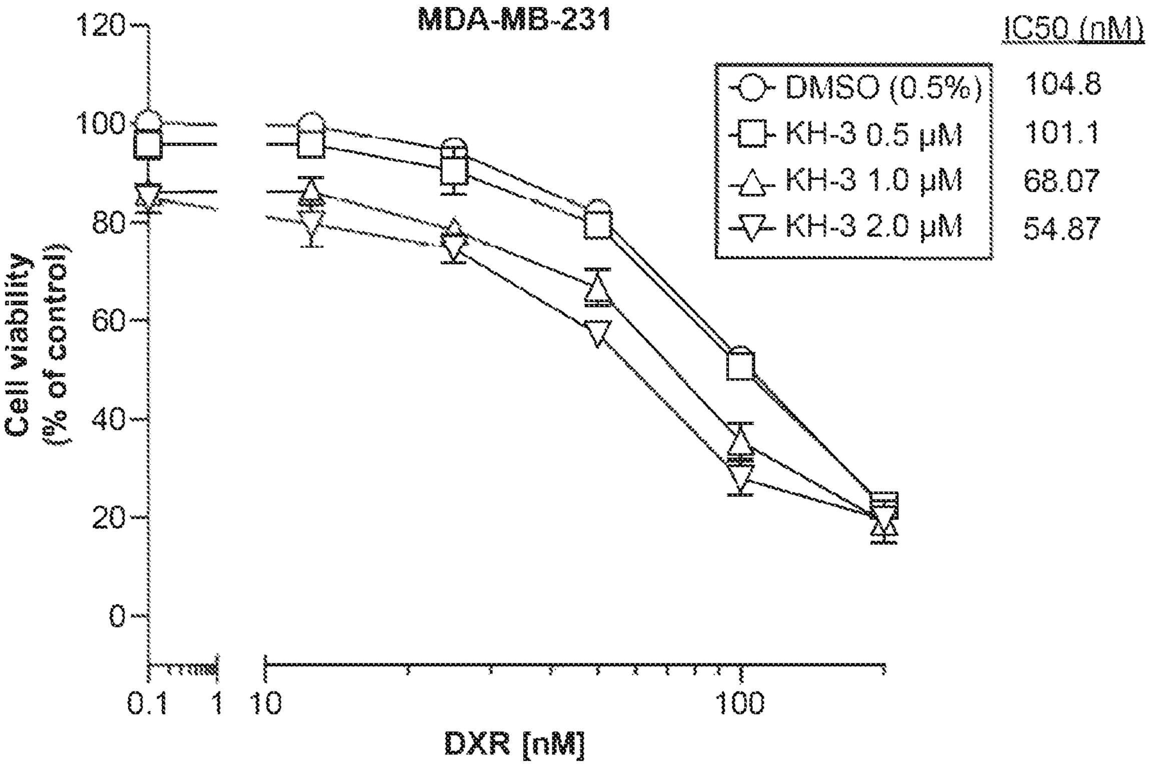
Figure 11D:
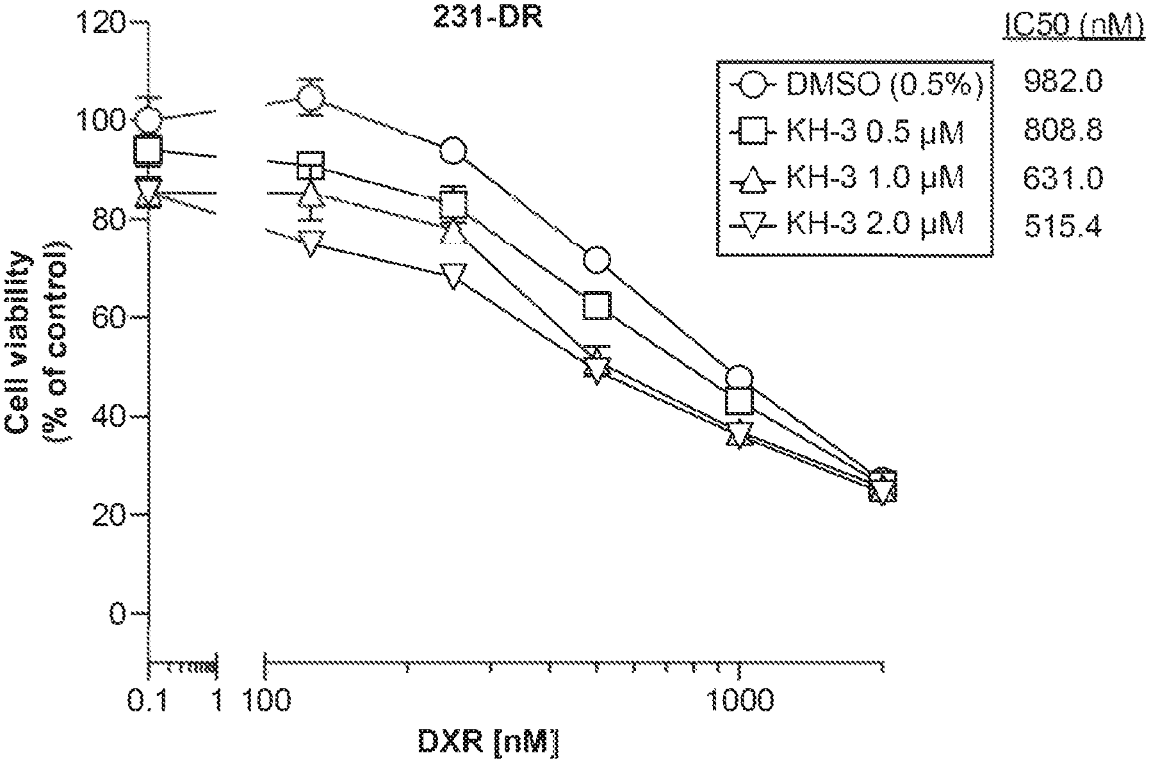

Cytotoxicity assays were then performed utilizing concentrations of KH-3 that were below the lethal threshold for the compound (a "sub-lethal concentration") in combination with docetaxel or doxorubicin to determine whether compounds of the present technology may sensitize cancer cell lines (including chemo-resistance cancer cell lines) to chemotherapy. FIGS. 11A-11B illustrate that sub-lethal concentrations of KH-3 sensitizes both MDA-MB-231 cells and docetaxel-resistant 231-TR cells to docetaxel treatment (FIGS. 11A-11B), and FIGS. 11C-D illustrate that sub-lethal concentrations of KH-3 sensitizes both MDA-MB-231 cells and doxorubicin-resistant 231-DR cells to doxorubicin treatment (FIGS. 11C-11D).

In Vivo Antitumor Activity

Initially, the maximum tolerated dose (MTD) was determined. MTD studies were conducted as a series of doses and schedule on groups of 3 mice per dose per schedule. Single-dose MTD was determined first, followed by multi-dose MTD using a schedule that would be used for efficacy studies. Gross necropsies were performed on all animals as well as selective pathology assessment, including those euthanized, moribund, found dead, or at termination. Liver, heart, kidneys, and other organs were examined histologically for abnormalities resulting from drug toxicity.

Xenograft and orthotopic models of cancer cell lines with HuR overexpression were used to test the in vivo therapeutic potential of compounds of the present technology. A person of ordinary skill in the art is well apprised of cancer cell lines with HuR overexpression, as exemplified by references 2-12 cited herein in the "References" section. Tumor models were established as described in Xu, L., et al., *(−)-Gossypol enhances response to radiation therapy and results in tumor regression of human prostate cancer*. Mol Cancer Ther, 2005. 4(2): p. 197-205.[35] Briefly, in 4-6 week old athymic NCr-nu/nu mice were used.

For efficacy studies, $0.5\times10^6$ MDA-MB-231 cells in 0.2 mL DMEM were inoculated to #2 mammary fat pad of mice and tumors were allowed to grow to approximately about 50 $mm^3$. Each group contained at least 5 animals with at least 10 tumors across the five animals. Animals were given compounds or vehicle via intraperitoneal injection three times per week for three weeks, such as described in Xu, L., et al., *Systemic p*53 *gene therapy of cancer with immunolipoplexes targeted by anti-transferrin receptor scFv*. Mol Med, 2001. 7(10): p. 723-34 and Xu, L., et al., *Self-assembly of a virus-mimicking nanostructure system for efficient tumor-targeted gene delivery*. Hum Gene Ther, 2002. 13(3): p. 469-81.[36,37] Compound doses were less than their predetermined MTD. The tumor sizes and animal body weights were measured twice a week. The end points for assessing antitumor activity were according to NCI standard procedures[35].

For the experimental metastasis model, Dr. Marc Lippman kindly gifted a 2LMP subclone that was generated from MDA-MB-231 and that formed lung metastasis in mice. $0.5\times10^6$ 2LMP cells stably expressing luciferase in 0.3 mL DMEM were intravenously injected into tail veins of mice. Immediately following injection, mice were imaged by bioluminescence to assure wide distribution and quality of the initial injection. The mice were then randomized into two groups and treated with 50 mg/kg KH-3 or vehicle control via intraperitoneal injection five times per week for five weeks. Bioluminescence imaging was taken weekly to monitor the metastasis burden at lung. When the imaging showed luminescent signaling at lung with automatic setting, the mouse was considered with tumor initiation. Imaging was then taken twice a week after first detectable signaling at lung. All animal experiments were carried out according to the protocol approved by the Institutional Animal Use and Care Committee at the University of Kansas.

Figure 12:
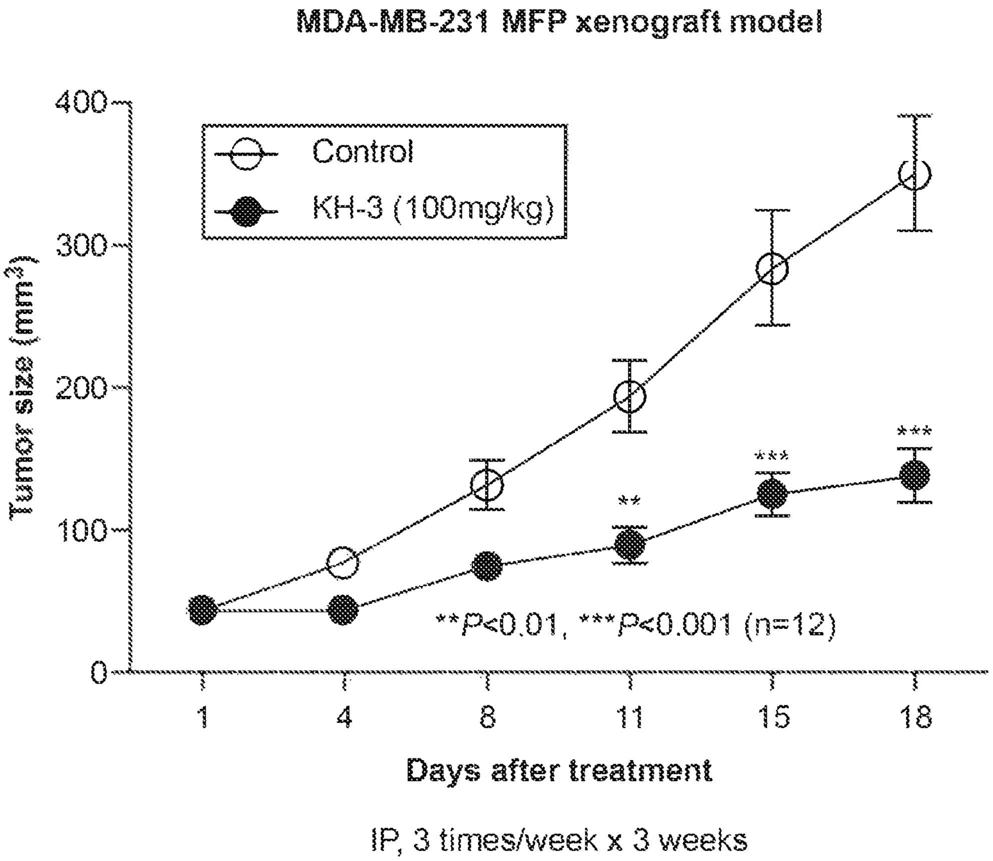
FIG. 12 illustrates the in vivo antitumor activity of KH-3 in a mouse MDA-MB-231 xenograft model, according to the working examples.

Illustrative of the present technology, FIG. 12 shows that compound KH-3 significantly decreased tumor growth as compared to the vehicle control in the MDA-MB-231 xenograft model (P<0.001, n=12). This data further evidences that the Ki indicated in the FP assay correlates with in vivo antitumor activity, especially in triple negative breast cancer.

Figure 13:
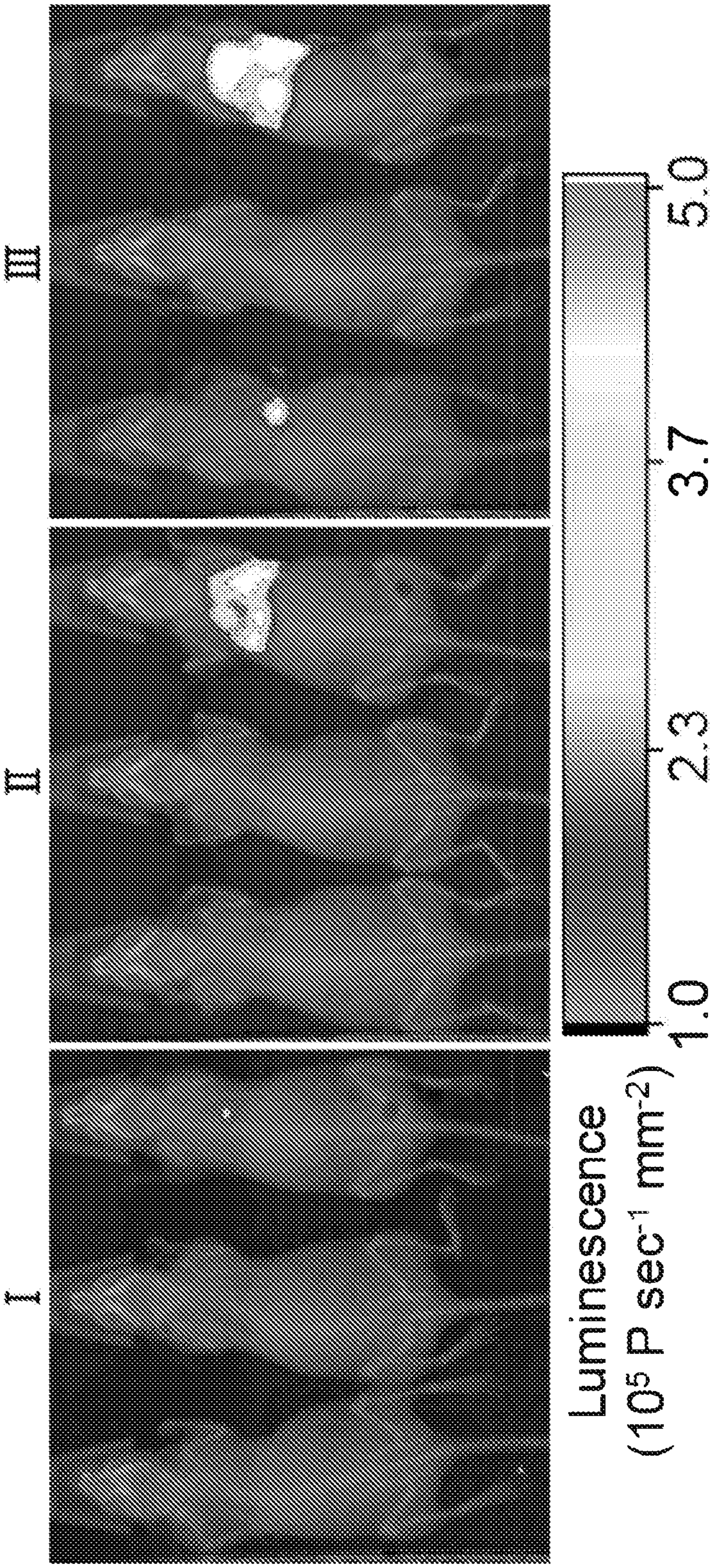
FIG. 13 presents representative images for mice at three stages of metastasis in a experimental metastasis model, according to the working examples. Image (I) shows mouse 3 ($3^{rd}$ from the left) with initial detection of early metastasis; image (II) shows mouse 1 ($1^{st}$ from the left) with initial detection of early metastasis and mouse 3 with lung metastasis progression; and image (III) shows mouse 1 with lung metastasis progression and mouse 3 close to moribund with extensive lung metastases.
Figure 14:
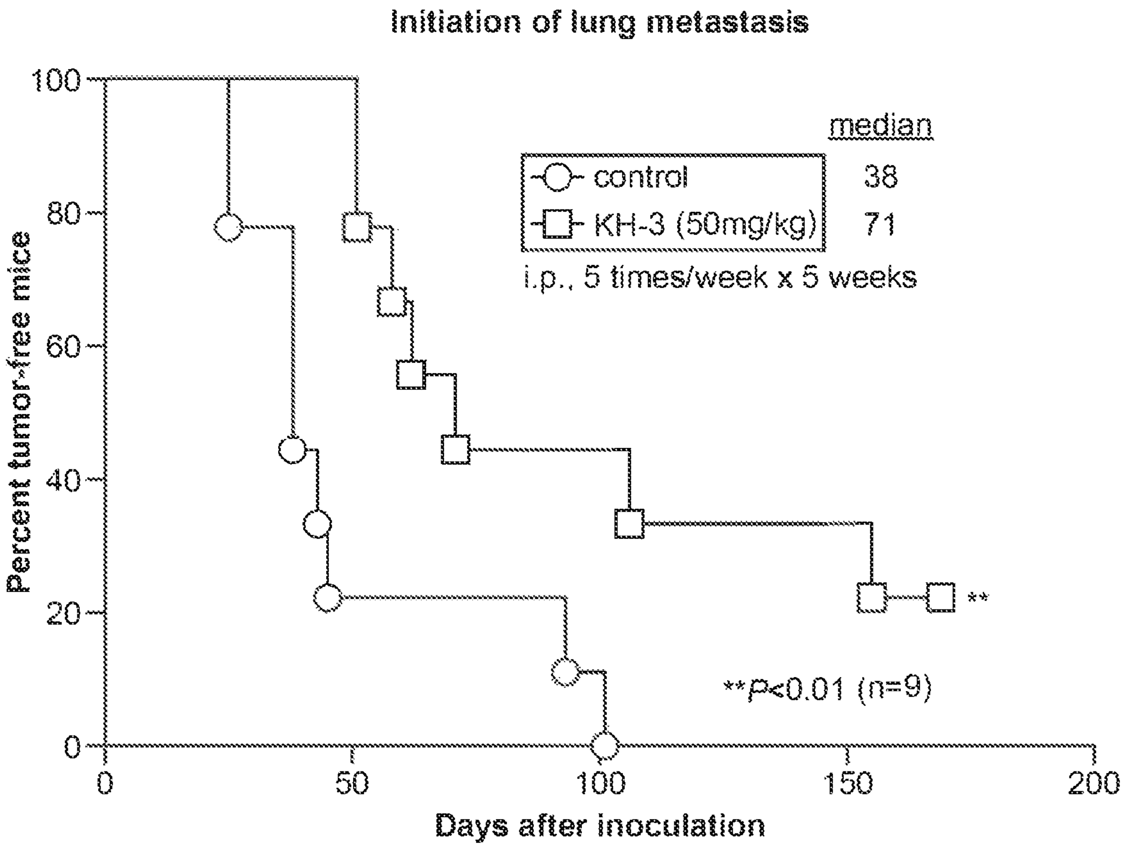
FIG. 14 illustrates the significantly delayed the initiation of pulmonary metastases by treatment with KH-3 (n=9, *P<0.05, P<0.01, log-rank test), according to the working examples FIG. 15** charts the overall survival rate of mice in the experimental metathesis model for a control group of mice versus mice treated with KH-3 (n=9, *P<0.05, **P<0.01, log-rank test), according to the working examples.
Figure 15:
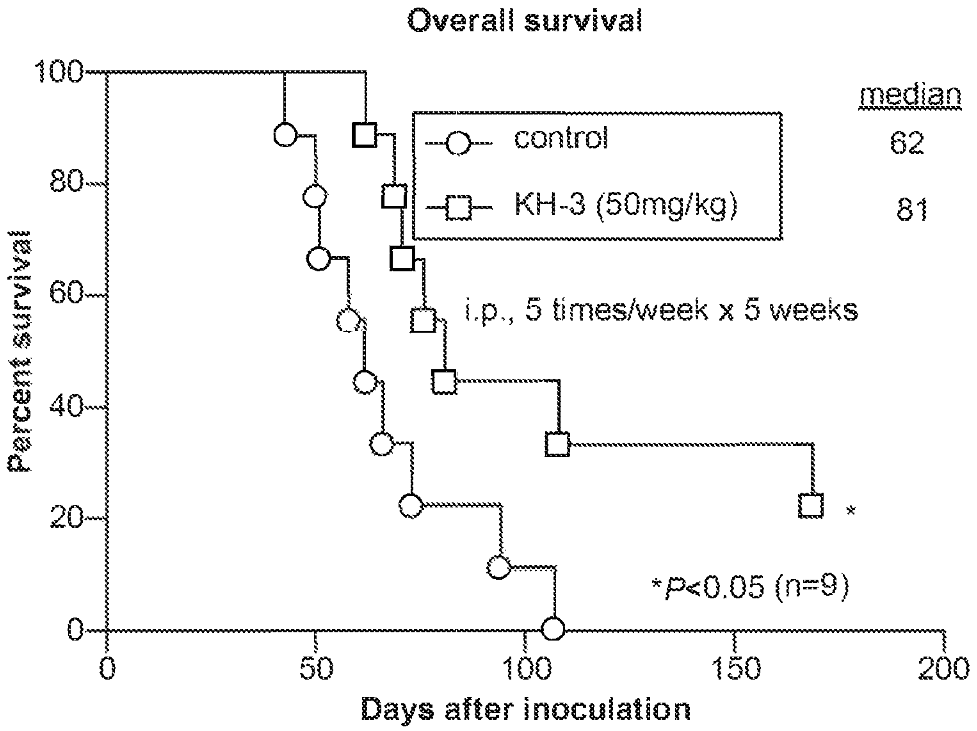
Figure 16:
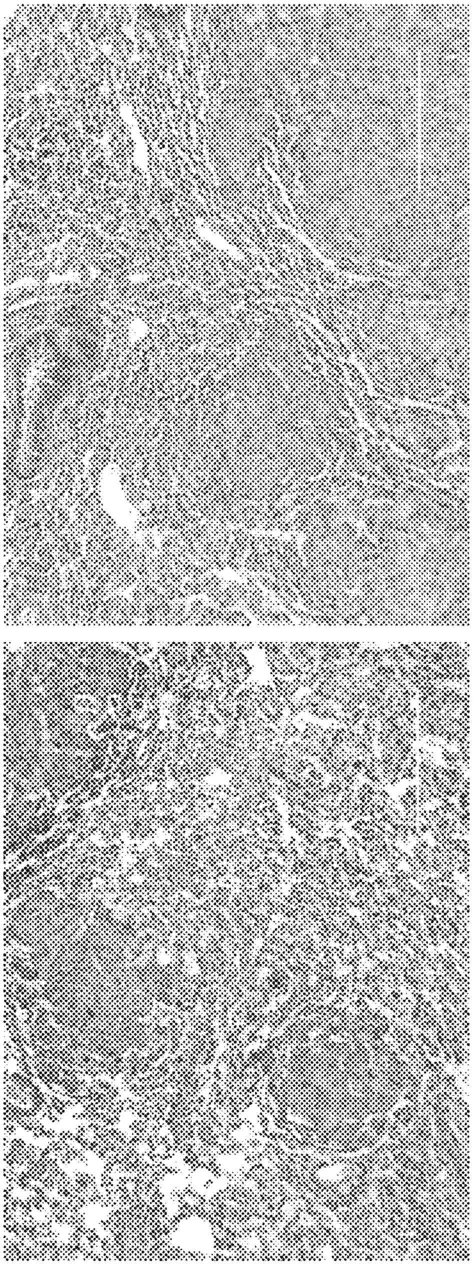
FIG. 16 presents representative H&E staining images of lungs which displayed tumor cells surrounding by lung cells, according to the working examples.
Figure 17:
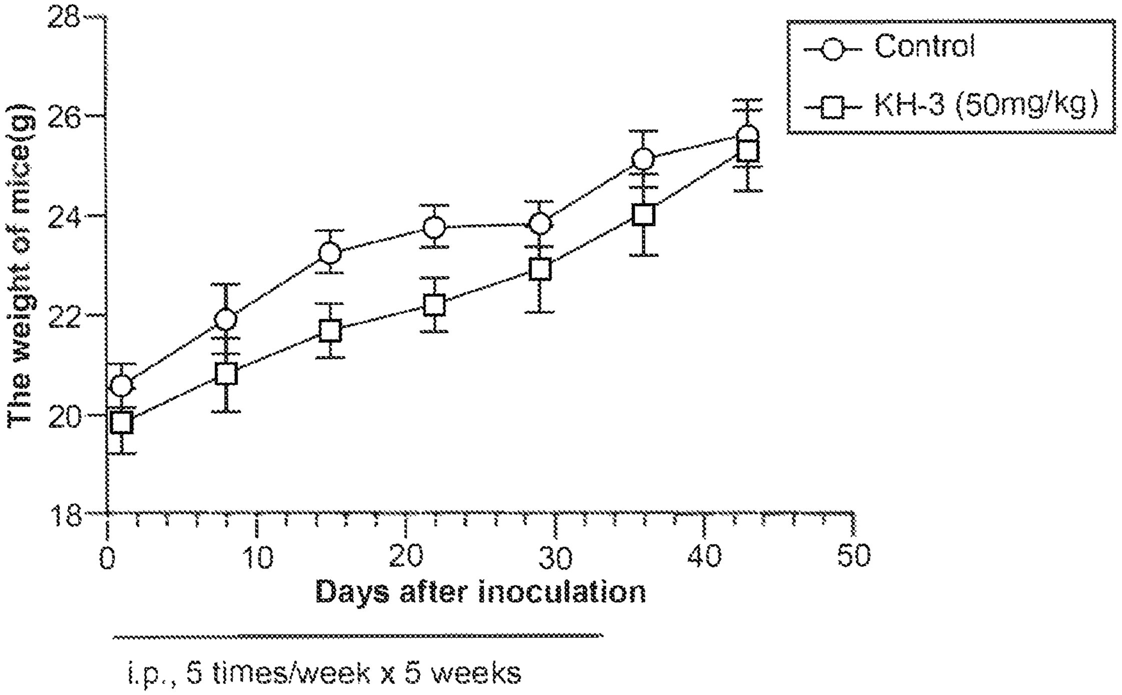
FIG. 17 provides the weight gain mice during the first 43 days in the experimental metathesis model for a control group of mice versus mice treated with KH-3, according to the working examples.

FIG. 13 presents representative images for mice at three stages of metastasis in the experimental metastasis model: image (I) shows mouse 3 with initial detection of early metastasis; image (II) shows mouse 1 with initial detection of early metastasis and mouse 3 with lung metastasis progression; and image (III) shows mouse 1 with lung metastasis progression and mouse 3 close to moribund with extensive lung metastases. As shown in FIG. 14, KH-3 treatment significantly delayed the initiation of pulmonary metastases. The median time for two groups is 38 and 71 days, respectively. KH-3 also decreased the metastasis rate. All mice (9/9) in control group had pulmonary metastases while 77.7% (7/9) mice in KH-3 group had pulmonary metastases at the end of experiment. KH-3 treatment significantly improved the survival time of mice as well. The median survival time in control group is 62 days while 81 days in KH-3 group (see FIG. 15). At the end of the experiment, all lung tissues were collected and performed immunohistochemistry staining. FIG. 16 presents representative H&E staining images of lungs, which displayed tumor cells surrounding by lung cells. Besides the primary outcome, the mice were monitored for potential side effects of KH-3. KH-3 treatment caused minor diarrhea in some mice. Some mice had swollen abdomens starting the fourth week of treatment, which may be induced peritonitis due to repeated intraperitoneal injection. No other side effects were noticed. The mice in KH-3 group gained weight similar to those in control group during the first 43 days of the experiment (see FIG. 17); after that, the mice in control group started to die so a weight curve after 43 days could not be plotted. These data evidence that KH-3 is a potent and safe agent to inhibit breast cancer metastasis in vivo.

Figure 18:
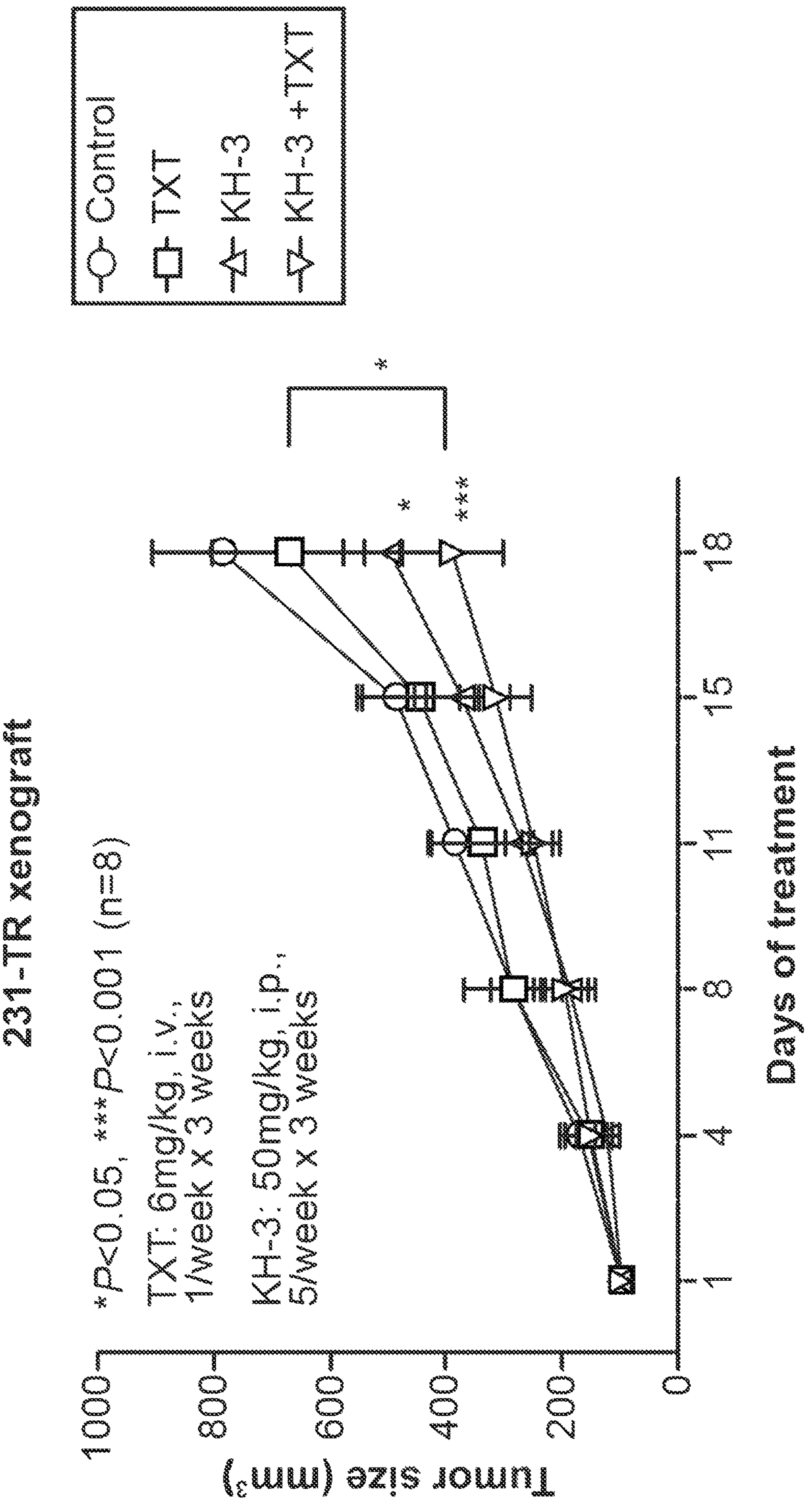
FIG. 18 graphically summarizes the in vivo antitumor activity of KH-3 in a mouse 231-TR xenograft model, illustrating that KH-3 significantly inhibits 231-TR tumor growth and sensitizes docetaxel-resistant tumors to docetaxel treatment, according to the working examples.

The in vivo antitumor efficacy of KH-3 was also examined in a 231-TR xenograft model. $1\times10^6$ 231-TR cells in 0.2 mL DMEM were inoculated to #2 mammary fat pad of mice and tumors were allowed to grow to approximately about 100 $mm^3$. The mice were then randomized into four groups and (i) treated with 50 mg/kg KH-3, (ii) treated with 6 mg/kg docetaxel, (iii) treated with 50 mg/kg KH-3 and 6 mg/kg docetaxel, or (iv) untreated. KH-3 was administrated via intraperitoneal injection five times per week for three weeks and docetaxel was administrated via tail vein injection one per week for three weeks. The results are summarized in FIG. 18 and illustrate that KH-3 significantly inhibits 231-TR tumor growth and sensitizes docetaxel-resistant tumors to docetaxel treatment.

Figure 19:
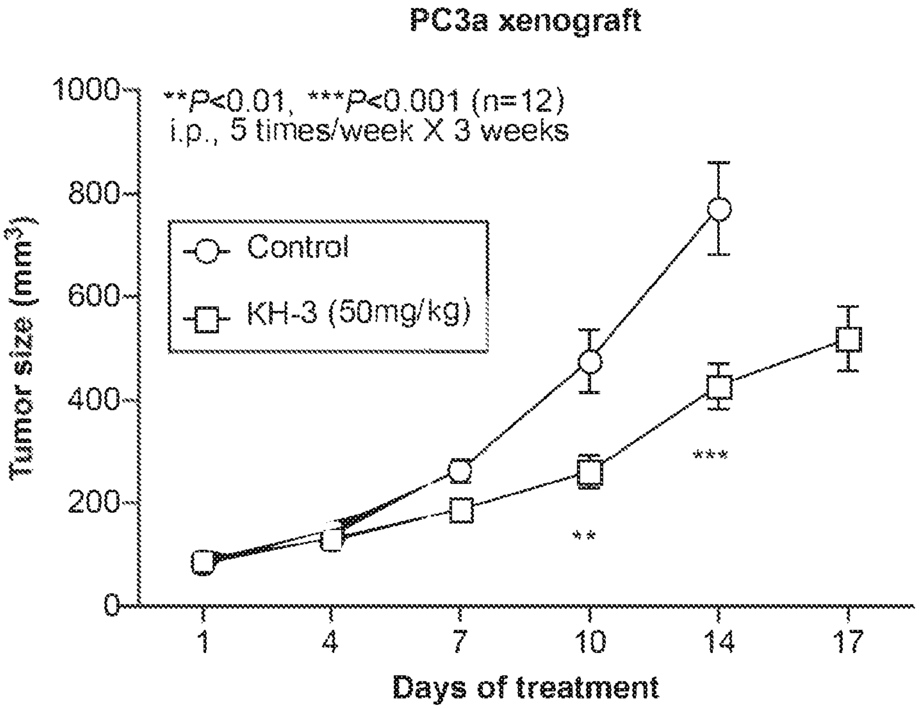
FIG. 19 graphically summarizes the in vivo antitumor activity of KH-3 in a mouse xenograft model using a more aggressive subline of PC-3 ("PC-3a"), illustrating that KH-3 treatment significantly inhibited PC-3a tumor growth compared to that of vehicle control group (P<0.001, n=12), according to the working examples.

The in vivo antitumor efficacy of KH-3 was further examined using a PC-3-derived subline PC-3a xenograft model in athymic nude mice. PC-3a was generated from a PC-3 formed subcutaneous tumor through multiple rounds of in vivo selection in mice, where PC-3a is more aggressive than PC-3. PC-3a cells were injected subcutaneously into both flanks of male athymic nude mice and tumors allowed to grow. When the xenografts reached ~100 $mm^3$, the mice were randomized into two groups and treated with KH-3, 50 mg/kg, i.p., 5 times/week×3 weeks or vehicle control. The results are summarized in FIG. 19 and illustrate that KH-3 treatment significantly inhibited PC-3a tumor growth compared to that of vehicle control group (P<0.001, n=12).

Figure 20:
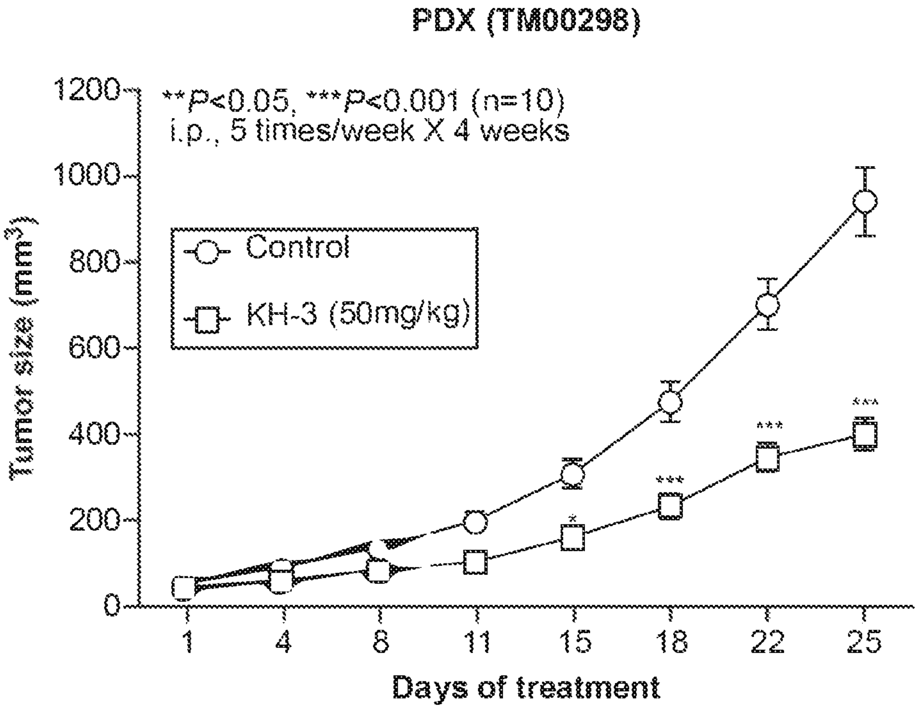
FIG. 20 graphically summarizes the in vivo antitumor activity of KH-3 in a mouse xenograft model using a patent-derived castration resistant prostate cancer, illustrating that KH-3 treatment significantly inhibited tumor growth compared to that of the vehicle control group (P<0.001, n=10), according to the working examples.

A castration resistant prostate cancer patient-derived xenograft (PDX) model was also used to assess the in vivo antitumor efficacy of KH-3. TM00298 (purchased from the Jackson Laboratory) was derived from a 71 year-old man with prostate cancer that had been treated with radiation therapy to the prostate, androgen deprivation therapy (ADT), and docetaxel chemotherapy. First, high expression of HuR protein in TM00298 was verified by immunohistochemistry and Western blot (data not shown), where TM00298 has high cytoplasmic HuR expression as well as total HuR expression. TM00298 grafts from donor NOD scid gamma (NSG) mice were implanted subcutaneously into the left flank of recipient NSG mice. When tumors reached ~500 $mm^3$, they were passaged again to the left flank of more NSG mice subcutaneously. When the xenografts reached ~50 $mm^3$, the mice were randomized into two groups and treated by intraperitoneal injection five times per week for four weeks with either 50 mg/kg KH-3 or vehicle control. FIG. 20 summarizes the results graphically and shows that KH-3 treatment significantly inhibited tumor growth compared to that of vehicle control group in this PDX model (P<0.001, n=10).

Activity of Compounds of the Present Technology Against Pancreatic Cancer

Materials and Methods

Cell Culture, Detection of Cell Viability, Migration/Invasion, and Tumor Spheres Formation Pancreatic cancer cell lines were obtained from the American Type Culture Collection (Manassas, VA). hTERT-HPNE cells (immortalized human pancreatic ductal epithelial cells) were donated by Dr. Anant at the University of Kansas Medical Center. MTT assay was used for cell viability detection, with starting cell number in 96-well plate of 3000/well (for 72 h treatment) or 5000/well (for 48 h treatment).

Wound healing assay was performed by scratching confluent monolayer with a 100 μL pipette tip. Wound recovery was calculated by 100%−(Remaining Area÷Original Area)×100% at each time point.

Matrigel invasion assay was performed using Boyden chambers (BD Biosciences, San Jose, CA) either pre-coated or uncoated with 0.1 mg/ml Matrigel, with 0.5% FBS inside and 10% FBS outside. Starting cell density was $1\times10^4$/well.

For tumor spheres formation, single cell suspension was plated into 96-well ultra-low attachment plates (Corning Inc., Corning, NY) at 100 cells/well in stem cell media, supplemented with B27 Supplement, 20 ng/ml human basic fibroblast growth factor, 20 ng/ml epidermal growth factor, 100 units/ml penicillin/streptomycin (Invitrogen, Grand Island, NY), and 4 μg/ml heparin calcium salt (Fisher Scientific, Pittsburgh, PA). Tumor spheres were counted after 14 days, and size was measured using Image J software.

RNA Isolation, cDNA Synthesis, and Real-Time PCR

Total RNA was extracted using TRIZOL reagent (Invitrogen, Grand Island, NY). cDNA synthesis was performed with 1 μg RNA using Omniscript RT kit (Qiagen, Valencia, CA), and diluted 1:5 for further use. Real-time PCR was performed using Bio-Rad iQ iCycler detection system with iQ SYBR green supermix (Bio-Rad Laboratories Ltd, Hercules, CA). Data was normalized to 18S rRNA.

To detect the decay of mRNAs, cells were treated with 5 μg/mL actinomycin D to block transcription (at −0.5 h). Total RNA was extracted at 0, 0.5, 1, 2, and 3 h. KH-3 (2 μM) was added 30 minutes after actinomycin D (at 0 h).

HuR Knockdown/Overexpression

Recombinant pcDNA3.1 HuR-flag Plasmid (pHuR) was provided by Dr. Dixon at the University of Kansas Cancer Center. The vector pcDNA3.1+(pVec) was purchased from Addgene (Cambridge, MA), and HuR siRNA from Qiagen (Valencia, CA). Plasmids were transfected by LIPOFECTAMINE 3000 reagent for 48 h, and siRNA by LIPOFECTAMINE RNAiMAX reagent for 24 h (Invitrogen, Grand Island, NY). HuR levels were verified by western blot.

CRISPR/Cas9 deletion of HuR gene was performed using the lentiCRISPRV2 vector (AddGene). The control single guide RNAs (sgRNAs) and HuR sgRNAs were cloned into the vector following procedures reported in Sanjana N E, Shalem O, Zhang F. *Improved vectors andgenome-wide libraries for CRISPR screening*. Nat Methods 2014; 11:783-784. The HuR lentiviral sgRNA or control sgRNA were co-transfected into HEK293FT cells with the packaging plasmids pMD2.G and psPAX2 (AddGene). MIA PaCa-2 cells were infected with virus-containing medium and then selected with 1.0 μg/mL puromycin. Single clones were generated by limited dilution.

RNP-IP Assay

Total cell lysate was used for immunoprecipitation with anti-HuR or normal rabbit IgG (Cell Signaling Technology, Beverly, MA), using the Immunoprecipitation Kit (Protein G) (Roche, Basel, Switzerland), supplemented with RNaseOUT™ Recombinant Ribonuclease Inhibitor (Invitrogen, Grand Island, NY) in all steps (100 U/mL). In the KH-3 treatment groups, KH-3 (2 μM) was supplemented in all steps. Total RNA was then extracted from the immunoprecipitation products by TRIZOL reagent and subjected to qRT-PCR analysis.

Dual-Glo Luciferase Reporter Assay

The full-length Snail mRNA 3'-UTR was synthesized by Genewiz (South Plainfield, NJ). The two truncated Snail mRNA 3'-UTRs (ΔAREs, and AREs) were cloned from total RNA of MIA PaCa-2 cells and amplified by PCR, and then constructed into the pmirGLO dual luciferase reporter plasmid. MIA PaCA-2 HuR KO cells were co-transfected with pmirGLO dual luciferase reporter with or without the constructions (full length, ΔAREs, AREs, or empty reporter) (Promega, Madison, WI) and pCDNA-3.1+-HuR (or empty vector) using LIPOFECTAMINE 3000 reagent (Invitrogen, Grand Island, NY). KH-3 was added at 24 h, and the dual-glo luciferase reporter assay was performed at 48 h using DUAL-GLO® Luciferase Assay System (Promega, Madison, WI).

Western Blot, Immunofluorescence and Immunohistochemistry

Cells were lysed with RIPA buffer (Sigma Al), and total protein was subjected to western blotting. BCA method was used for protein quantification (Pierce BCA protein assay kit, Waltham, MA). Blots were established using either Pierce ECL substrate or Pierce ELC+ substrate (Thermo Scientific, Rockford, IL).

Immunofluorescence detection of protein expression was performed with cells grown on 6-well chamber slides as routine. Blocking was performed using 5% Goat serum+0.3% Triton X-100. Nucleus were stained with ProLong® Gold Antifade Reagent containing DAPI (Cell Signaling Technology, Beverly, MA).

Immunohistochemistry was performed with paraffin-embedded tissue sections (5 μM thick), as routine. DAB were used to develop the sections (HRP/DAB (ABC) detection IHC kit, Abcam, Cambridge, UK). All the sections were then counterstained with hematoxylin.

Mouse Tumor Models and KH-3 Treatment

All animal procedures were approved by the Institutional Animal Care and Use Committee at the University of Kansas Medical Center under the protocol #2015-2247. Dose of KH-3 was pre-determined by a pilot experiment to be 100 mg/kg body weight, intraperitoneal injection (IP), three times weekly. All treatment in this pancreatic cancer section of the present disclosure concerning KH-3 used this dose regimen.

A subcutaneous tumor model was used to determine tumor formation rate. MIA PaCa-2 HuR WT cells or MIA-PaCa-2 HuR KO cells were inoculated into the flank of female Ncr nu/nu mice at the number of $2\times10^6$ cell in PBS. Tumor formation was monitored daily and tumor size was measured 3 times/week by using a digital caliper.

An orthotopic pancreatic tumor model was used to determine treatment effects of KH-3. Luciferase-expressing PANC-1 cells (PANC-1-Luc, multi-clones) were established by the Preclinical Proof of Concept Core Laboratory (University of Kansas Medical Center, Kansas City, KS). A small subcostal laparotomy was performed in female Ncr nu/nu mice to expose the pancreas, and $2\times10^5$ PANC-1-Luc cells in 50 μL PBS were injected into the tail of pancreas. After 11 days, the localized tumors inside the pancreas of these donor mice were removed and minced into small pieces of 1 $mm^3$ cube. One tumor cube was implanted into the pancreas of one recipient nude mouse by laparotomy. After 11 days, the recipient mice were scanned for xenograft formation using an IVIS imaging system (Waltham, MA) upon IP injection of 150 mg/kg D-luciferin. Mice were grouped based on tumor burden and treatment commenced as described, with weekly follow-up imaging. Treatment lasted for 5 weeks, and gross necropsy was performed at the end of treatment.

Data Analysis

Statistical analysis was performed using SPSS software for student's T-test, Log Rank test, one-way Anova with Turkey's Method, or Mann-Whitney's U test as each condition applies. A difference was considered significant at the $p<0.05$ level. Correlation was analyzed by Pearson Test.

Results

HuR Enhances Pancreatic Cancer Cell EMT, Migration, and CSCs

Figure 21:
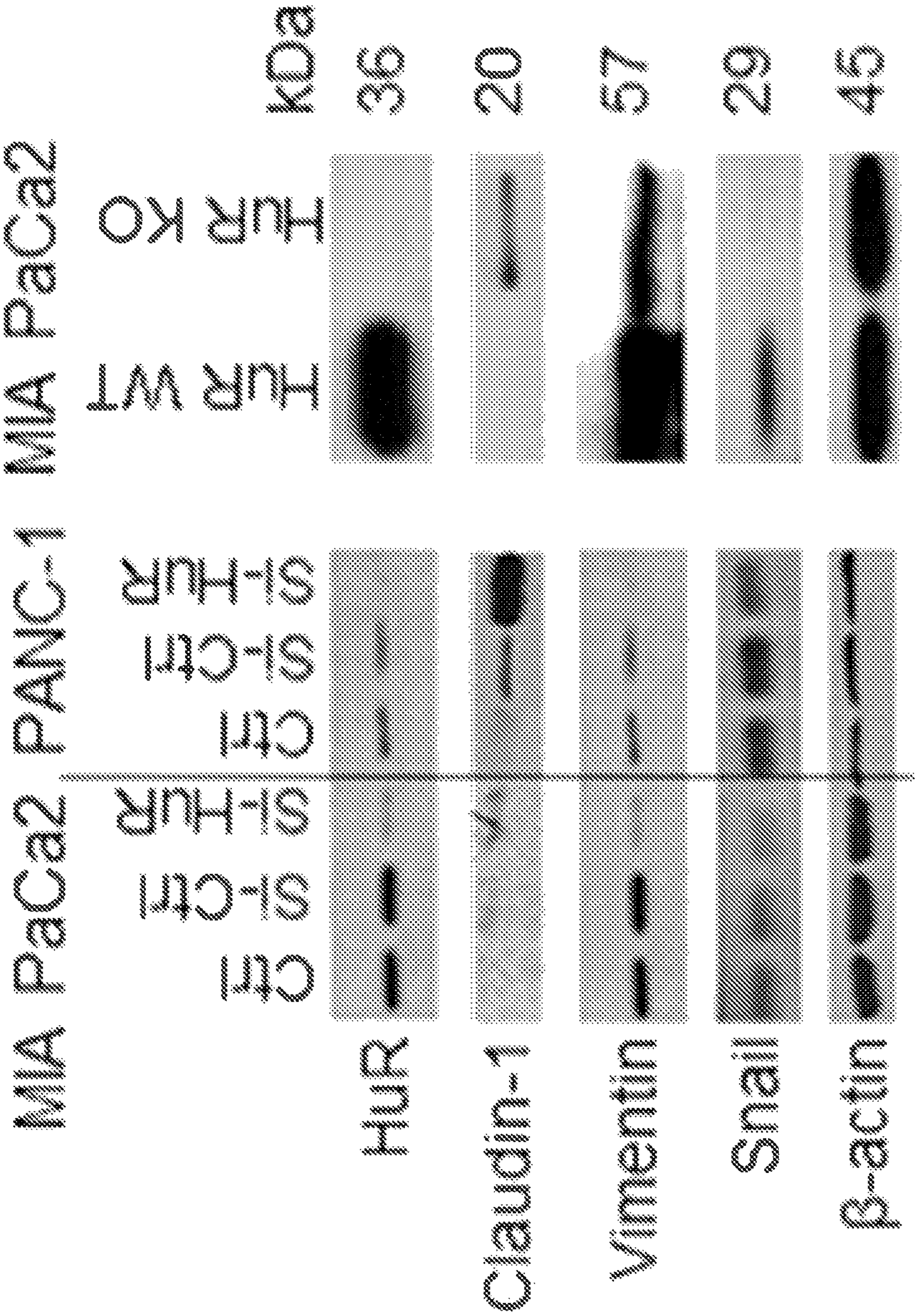
FIG. 21 provides a Western blot analysis of MIA PaCa-2 and PANC-1 cells showing expression of HuR and markers of EMT, according to the working examples. β-actin was a loading control. Left: Cells were transfected with Si-Ctrl or Si-HuR for 24 h, or un-transfected (Ctrl). Right: HuR KO were cells knockout of HuR gene by CRISPR/Cas9 procedure. HuR WT were cells transfected with control sgRNA.

To study the role of HuR in pancreatic cancer cell EMT, HuR expression was first silenced by transfecting siRNAs targeting HuR mRNA (siHuR), and down-regulation of HuR protein was validated by western blots. In two human pancreatic cancer cell lines PANC-1 and MIA PaCa-2 transfected with siHuR, the cellular morphology changed to a more epithelium-like state compared to each of their parent cells, characterized by less spindle-like cells, shortened cell length and/or enlarged cell diameter. Consistent with this phenotypical change, the expressions of signature EMT genes in both cells were altered (FIG. 21): the epithelial marker Claudin1 was significantly upregulated, the mesenchymal marker Vimentin was downregulated, and the EMT enhancing transcription factor Snail was significantly decreased. We then performed permanent deletion of HuR gene in MIA Paca-2 cells by a CRISPR/Cas-9 method. As expected, the deletion caused a depletion in HuR protein in the cells (FIG. 21). The morphology of HuR-deleted cells (HuR KO) showed a more epithelium-like state compared to the control cells, again with increase in Claudin1, decrease in Vimentin and Snail, consistent with the results in siHuR transfection (FIG. 21). Claudin1 expression was further confirmed by immunofluorescence staining in the siHuR transfected MIA PaCa2 cells, where the results clearly showed increase of Claudin1 expression.

Figure 22:
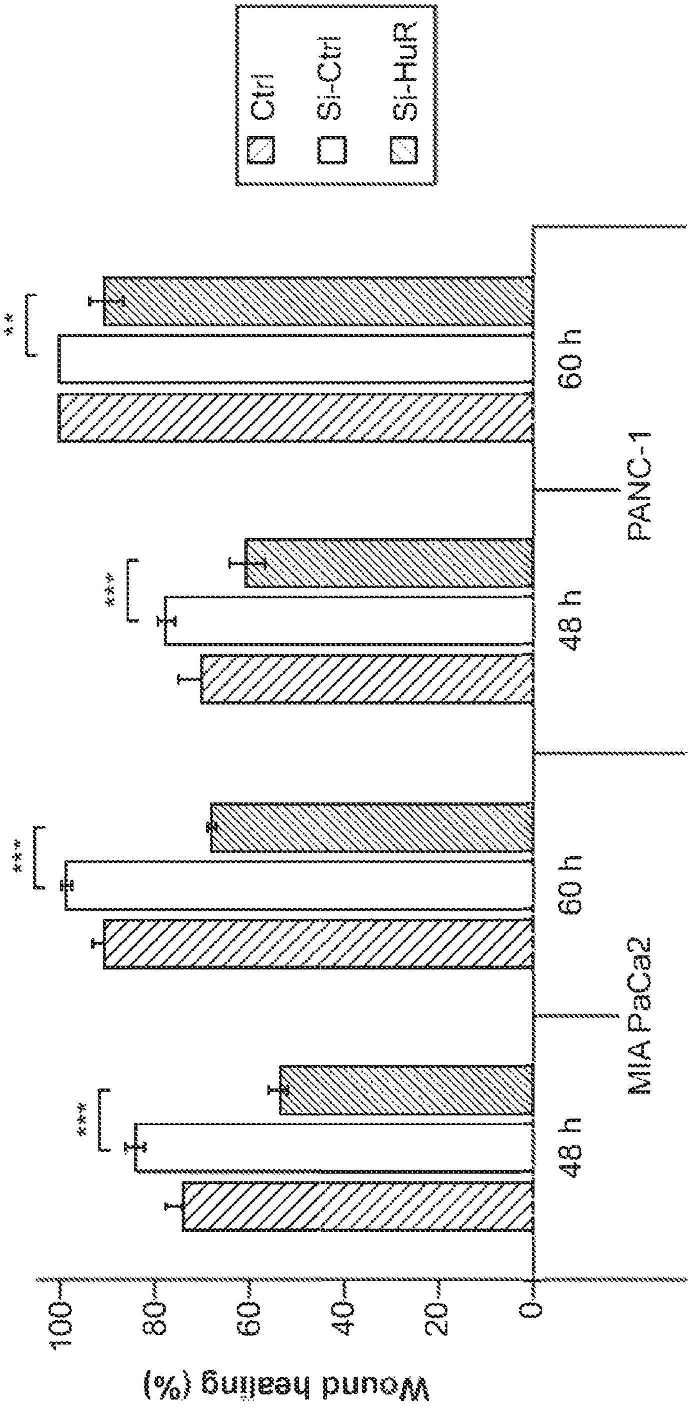
FIG. 22 provides the results of wound healing assays with MIA PaCa2 and PANC-1 cells, according to the working examples, where the bar graphs represent Mean±SEM of ≥3 repeats. *, p<0.05; , p<0.01; *, p<0.001 with one-way ANOVA-Tukey's test.
Figure 23:
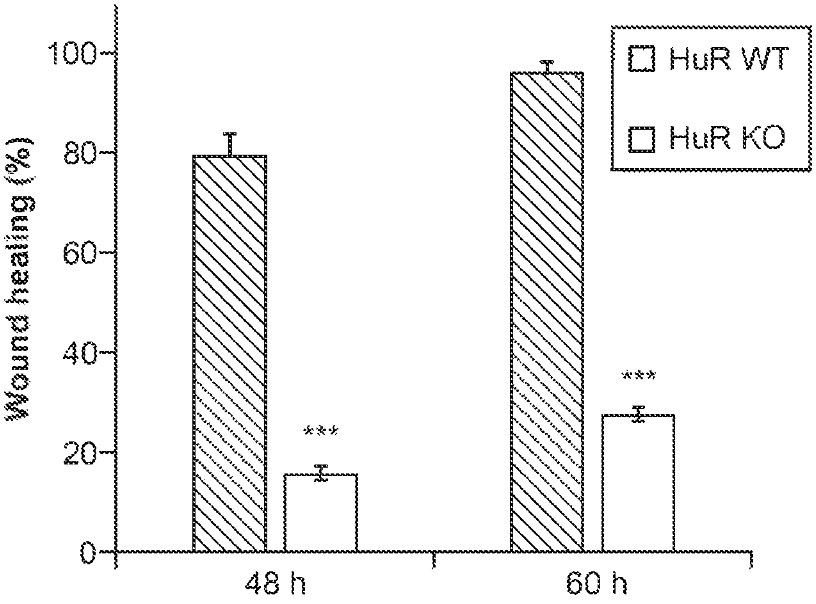
FIG. 23 provides the results of wound healing assays with MIA PaCa2 cells ("HuR WT") versus MIA PaCa2 cells with HuR gene deletion ("HuR KO"), according to the working examples, where the bar graphs represent Mean±SEM of ≥3 repeats. *, p<0.05; , p<0.01; *, p<0.001 with one-way ANOVA-Tukey's test.

As EMT promotes cancer cells migration and invasion, we expected HuR downregulation would inhibit pancreatic cancer cell migration and invasion, and HuR overexpression would enhance them. Indeed, siHuR significantly decreased the migration of PANC-1 and MIA PaCa-2 cells in a wound healing assay (FIG. 22). Consistently, and as illustrated in FIG. 23, HuR KO MIA PaCa-2 cells also had decreased ability to migrate versus MIA PaCa-2 cells (where MIA PaCa-2 cells are referenced as "HuR WT" in FIG. 23 and HuR KO MIA PaCa-2 cells referenced as "HuR KO" in FIG. 23). Migration/invasion were further assessed using matrigel uncoated and coated Boyden chambers. siHuR inhibited migration and/or invasion in both MIA PaCa2 cells and PANC-1 cells, and HuR gene deletion in MIA PaCa2 cells greatly impaired cell migration and invasion.

Figure 24A:
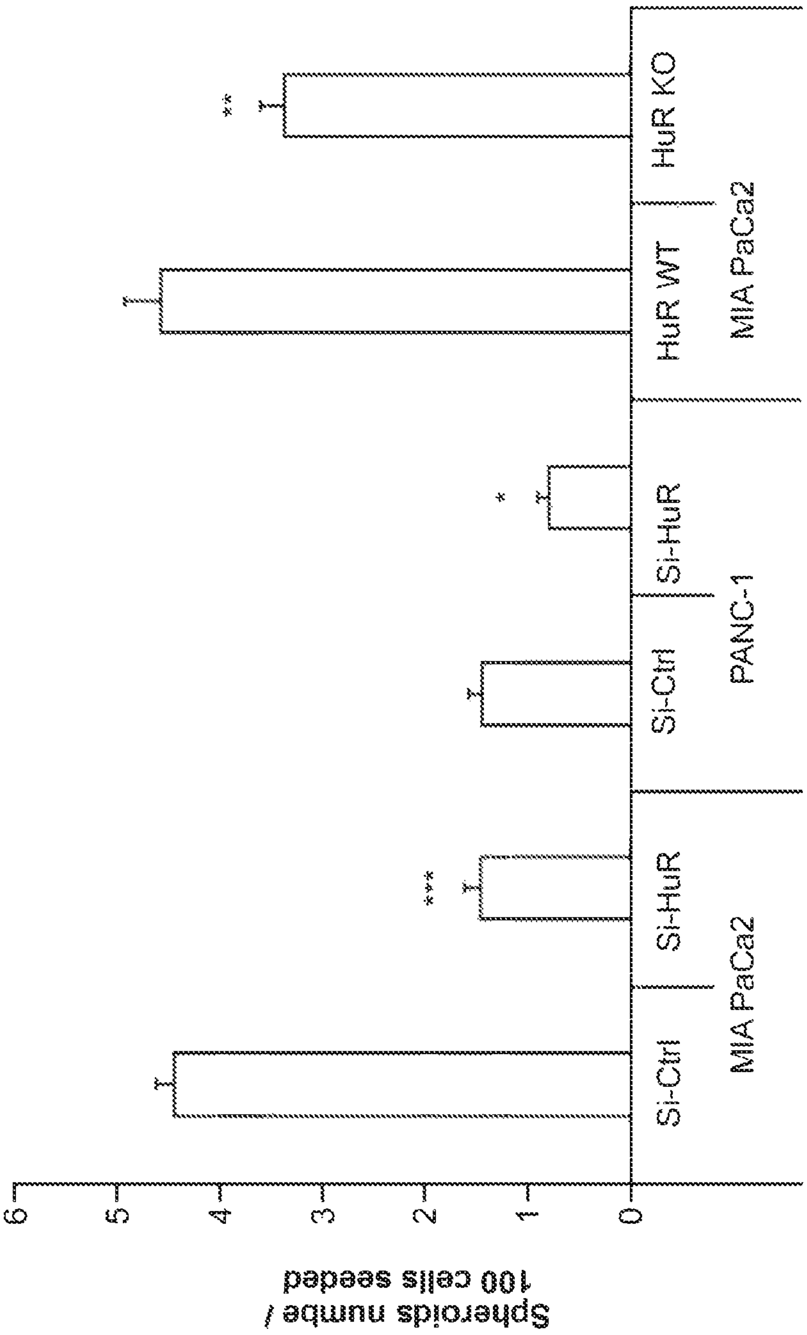
FIGS. 24A-24B provide the results of tumor spheroid formation assays described in the working examples illustrating the number (FIG. 24A) and size (FIG. 24B) of tumor spheres of PANC-1 and MIA PaCa2 cells without and with siHuR transfection as well as wild-type MIA PaCa2 cells ("HuR WT") compared to MIA PaCa2 cells with HuR gene deletion ("HuR KO"). *, p<0.05; , p<0.01; *, p<0.001 with one-way ANOVA-Tukey's test.
Figure 24B:
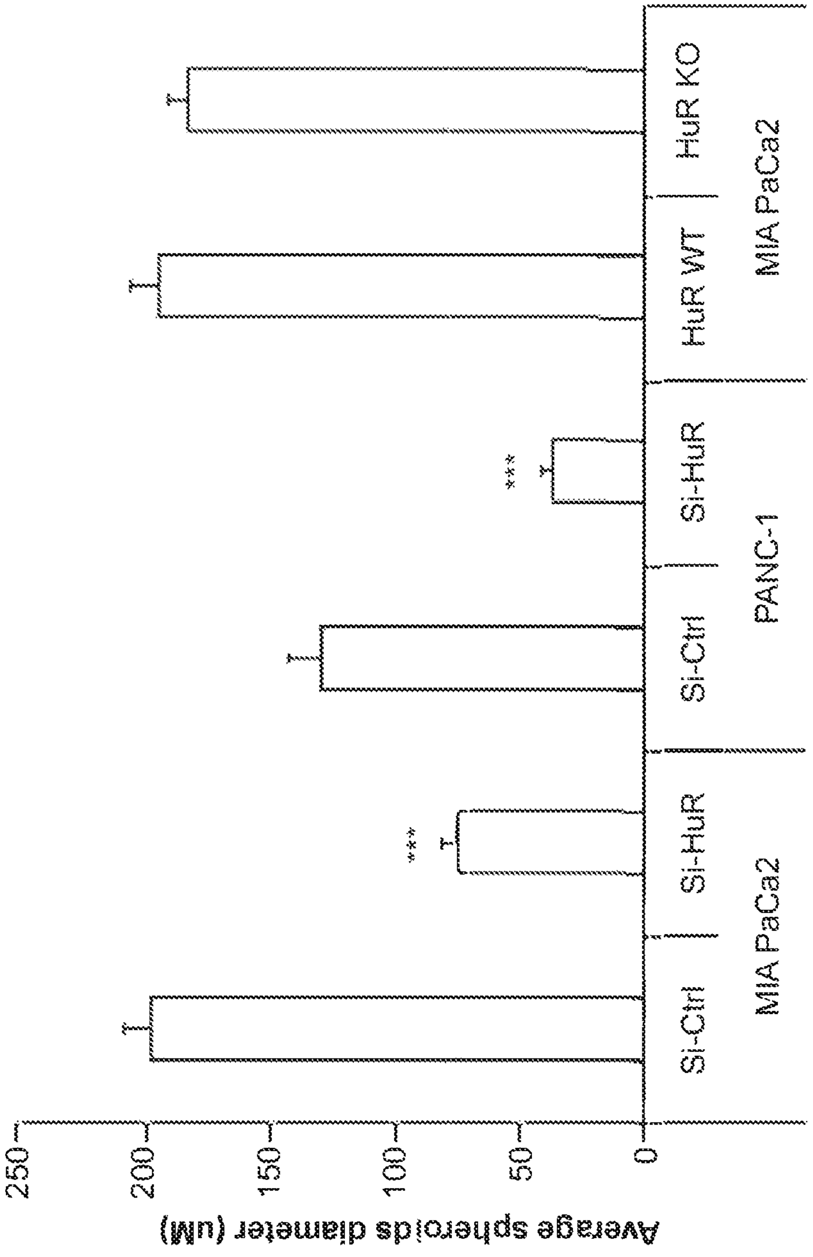

Cancer stem-like cell population (CSCs) were also examined using tumor spheroid formation assay. Data showed that the number (FIG. 24A) and size (FIG. 24B) of tumor spheres were both significantly reduced in PANC-1 and MIA PaCa2 cells with siHuR transfection, indicating inhibition in CSCs. The HuR gene deletion in MIA PaCa2 cells (referenced as "HuR KO" in FIGS. 24A-24B) also decreased the number of spheres, but did not influence the sizes of the spheres formed. HuR was then re-expressed in the HuR KO MIA PaCa2 cells and the EMT markers, migration, and CSCs examined, where HuR re-expression decreased the epithelial markers Claudin1 and ZO-1, and increased the mesenchymal marker Vimentin, and Snail. The restoration of HuR expression in the HuR KO MIA PaCa2 cells also enhanced migration and increased number of tumor spheres compared to the HuR KO MIA PaCa2 cells while the size of the formed spheres slightly decreased.

Figure 25:
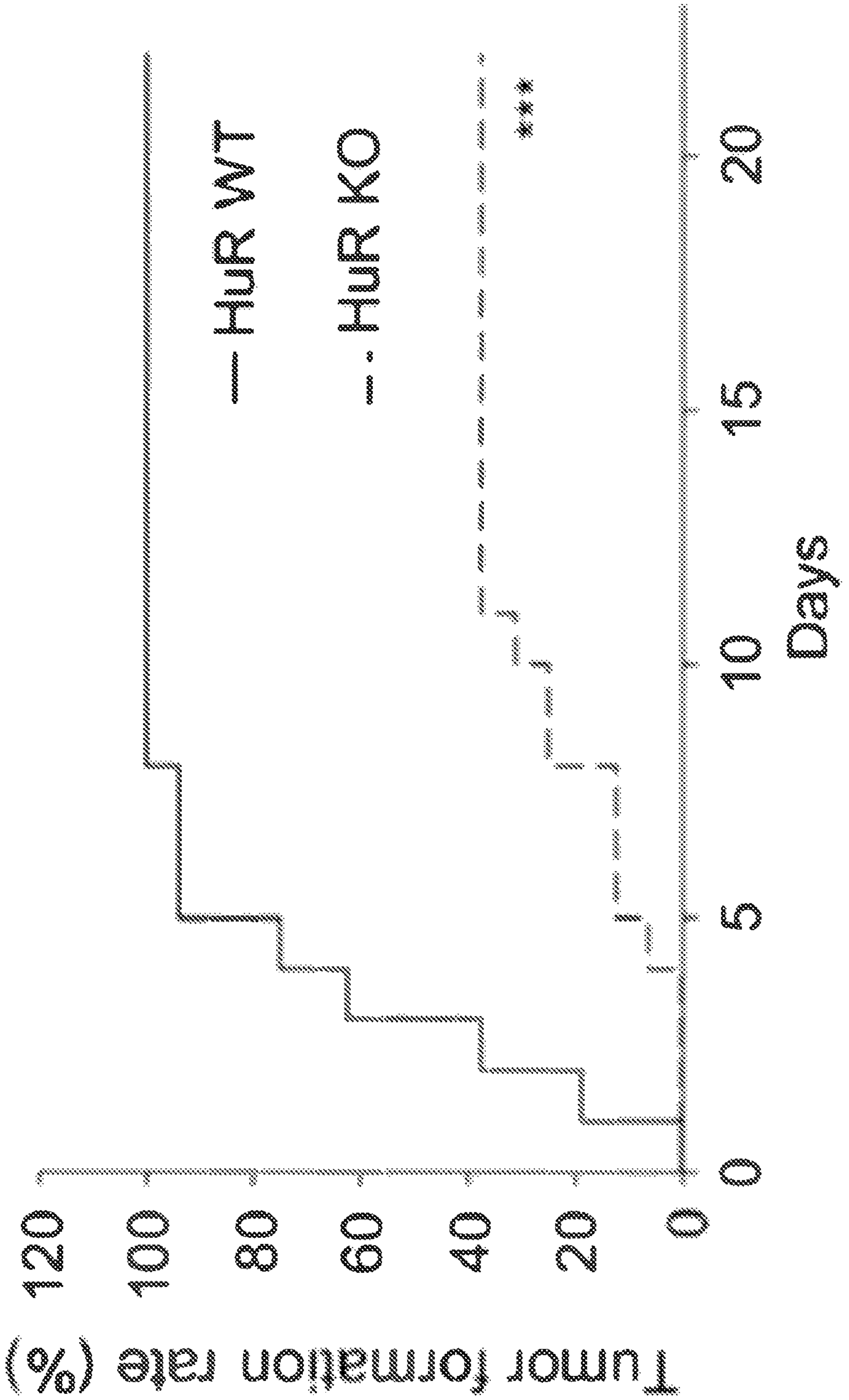
FIG. 25 provides the in vivo tumor formation rate of wild-type MIA PaCa2 cells ("HuR WT") versus MIA PaCa2 cells with HuR gene deletion ("HuR KO") in nude mice (n=16 per group), according to the working examples. ***, p<0.001 with Log-rank test.
Figure 26:
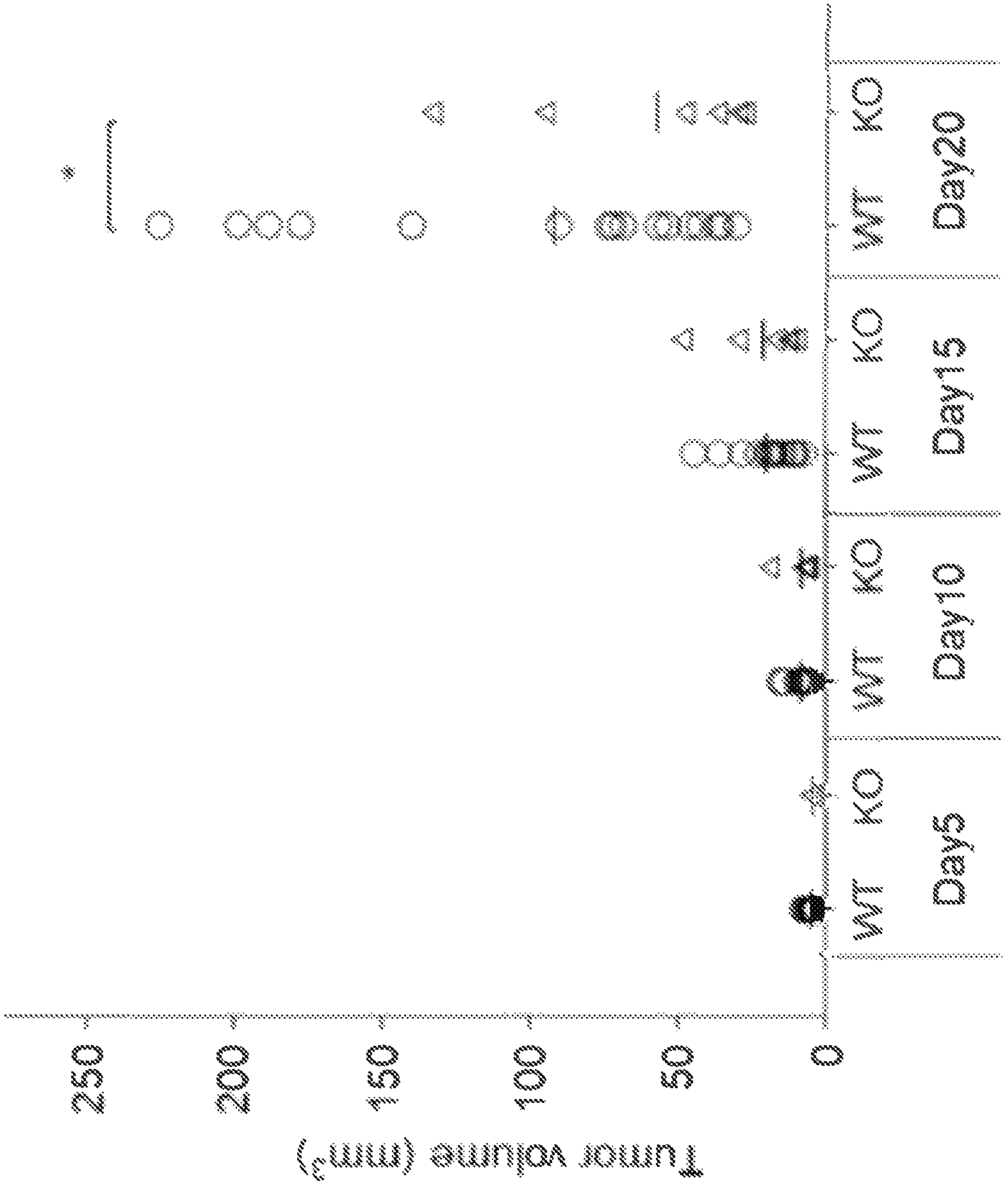
FIG. 26 provides the volume of the tumors illustrated in FIG. 25, according to the working examples. Each circle or triangle represents a tumor. The short bars show the mean tumor volume of each group. *, p<0.05 with Mann-Whitney U test.

As the number of CSCs is responsible for tumorigenicity in vivo, we compared the tumor formation rate of MIA PaCa2 HuR KO cells to that of the CRSPR/Cas9-control cells (HuR WT cells) in nude mice. At the inoculation number of $2\times10^6$ cells subcutaneously, the HuR WT cells yield 100% (16/16) tumor formation in 8 days after injection (day 8). The HuR KO cells had a tumor formation rate of 25% (4/16) at day 8, and only reached a final tumor formation rate of 37.5% (6/16) at day 21 (FIG. 25). The HuR KO tumors also grew slower than the HuR WT tumors, as illustrated in FIG. 26.

HuR Regulates the Expression of Snail

Figure 27:
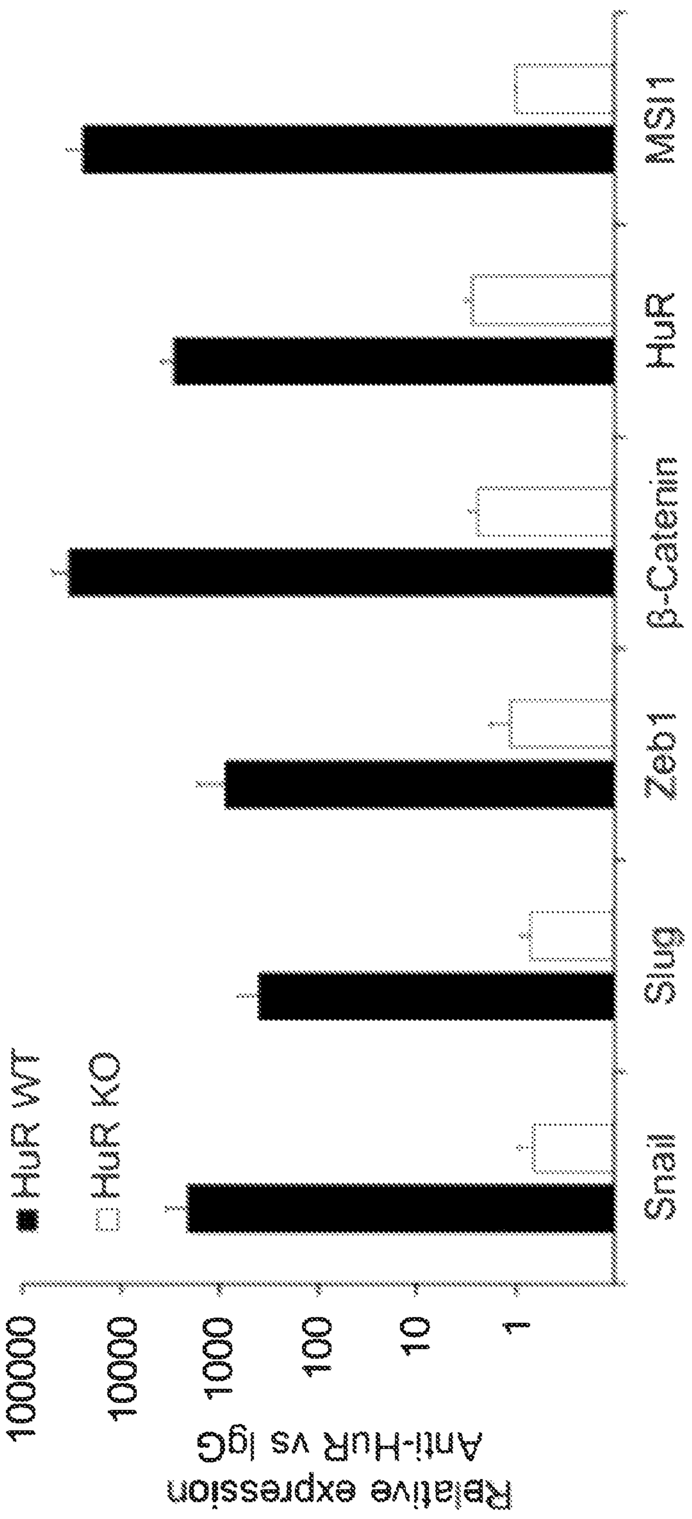
FIG. 27 provides the results of RNP-IP detection of HuR binding RNAs of EMT related genes, according to the working examples. Data for each individual mRNA was normalized to the IgG pull-down product of that mRNA. Bar graphs show Mean±SEM of 9 repeats. *, p<0.05; **, p<0.01 with one-way ANOVA-Tukey's test or Student's t-test.

HuR typically stabilizes its targeting mRNAs and promotes translation by binding to adenine- and uridine-rich elements (AREs) located in the 3'untranslated region (UTR) of the target mRNA. Whether HuR binds to the mRNAs of important regulators of EMT and CSC was examined using a ribonucleoprotein immunoprecipitation (RNP-IP) assay as described in Hassan M Q, Gordon J A, Lian J B, et al. *Ribonucleoprotein immunoprecipitation* (*RNP-IP*): *a direct in vivo analysis of microRNA-targets*. J Cell Biochem 2010; 110.817-22. Pull-down products from MIA PaCa2 total cell lysate using anti-HuR antibody were quantified for RNA components by qRT-PCR. As illustrated in FIG. 27, mRNAs of a panel of EMT/CSC regulators (Snail, Slug, Zeb1, and β-catenin) showed strong association with HuR protein as well as the mRNAs of the known HuR targets Msi1 and HuR itself, in contrast, in HuR KO cells this panel of mRNAs were not pulled down.

HuR WT and HuR KO MIA PaCa2 cells were treated with actinomycin D to block transcription, and then the stability of these mRNAs was detected over time. Data showed significantly enhanced degradation of Snail mRNA, but the decay of the mRNAs of Slug, Zeb1 and β-catenin did not change by the knockdown of HuR despite binding of their mRNAs to HuR. Consistent with these results, the protein expression of Snail was decreased with HuR knockdown (FIG. 21), whereas the protein levels of Slug, Zeb1 and β-catenin were minimally influenced.

Figure 28:
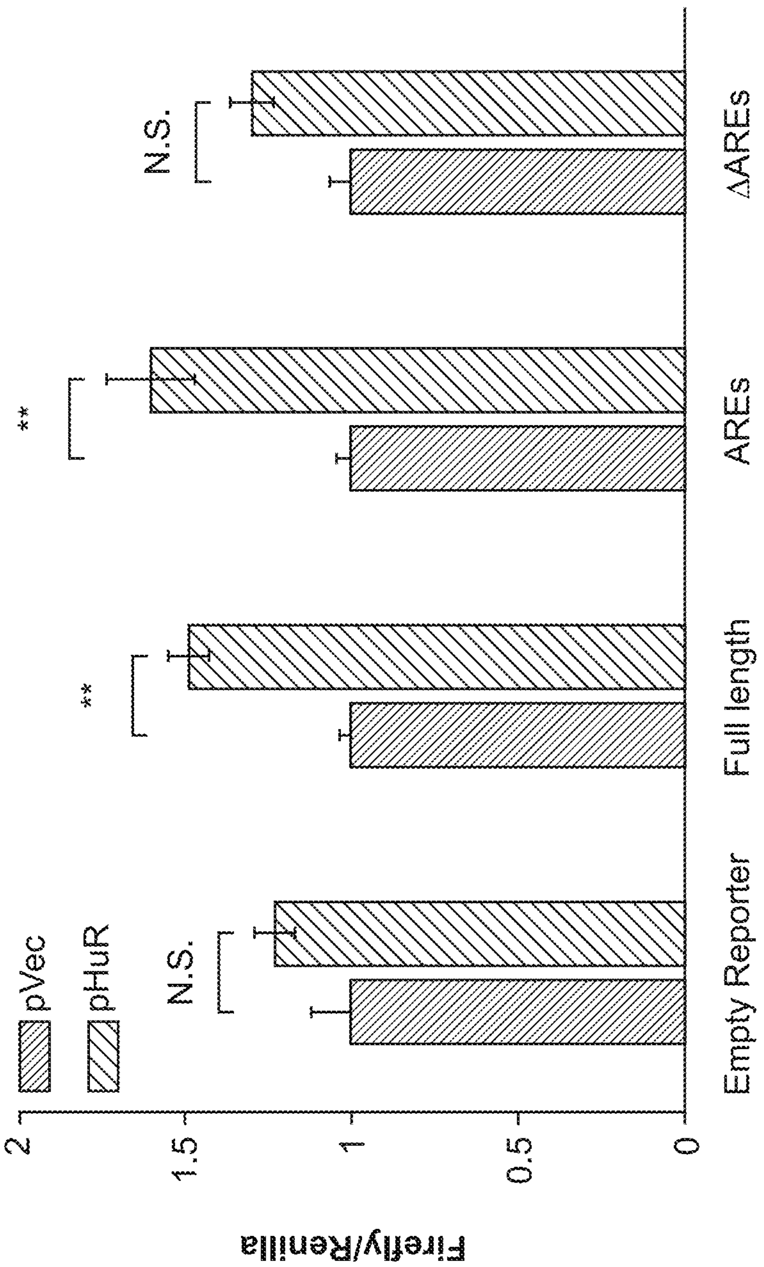
FIG. 28 provides the results of a luciferase reporter assay, according to the working examples, where MIA PaCa2 HuR KO cells were co-transfected with HuR (or vector) and the dual-luciferase reporter with Snail 3'-UTR constructions (either the Full length, AREs or ΔAREs, or empty reporter). *, p<0.05; **, p<0.01 with one-way ANOVA-Tukey's test or Student's t-test.

The direct interaction of HuR with Snail mRNA 3'-UTR was examined with a luciferase reporter assay. The full length 3'-UTR, and two truncated Snail mRNA 3'-UTRs (ΔAREs, and AREs) were each constructed into the pmirGLO vector, which contains a firefly luciferase gene under the PGK promoter. The sequence of ΔAREs did not contain the AU-rich HuR binding elements, and the sequence of AREs contained the major part of the AU-rich elements in the 3'-UTR. MIA PaCa2 HuR KO cells were then co-transfected with HuR and the pmirGLO plasmid containing each of the constructed Snail UTRs. Data clearly showed that only with the full length 3'-UTR and the AREs, HuR transfection could enhance luminescence signal, and when there lacked the HuR binding elements (ΔAREs), the luminescence signal did not change with HuR transfection (FIG. 28).

Figure 29:
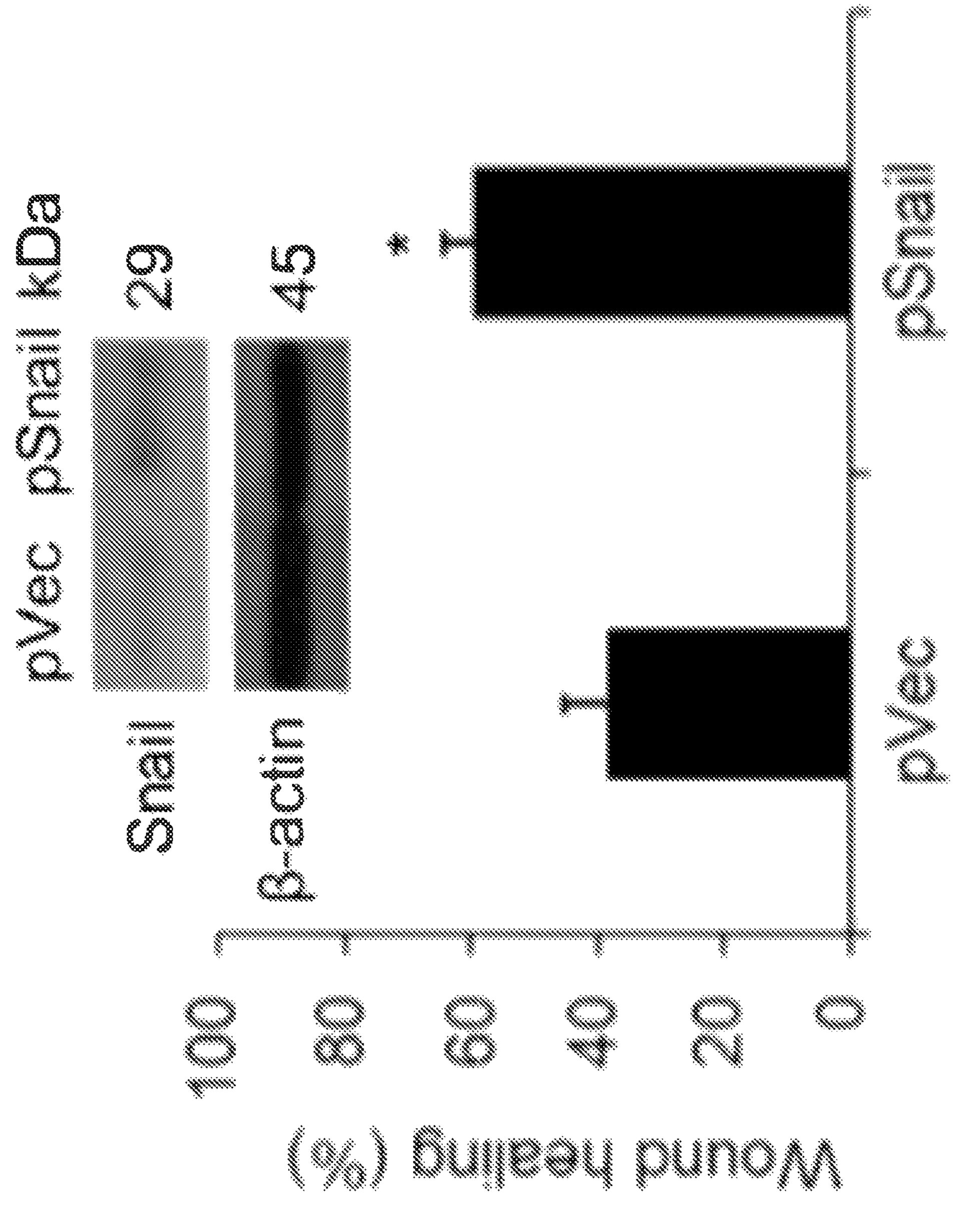
FIG. 29 provides the results of a wound healing assay with MIA PaCa2 HuR KO cells with Snail overexpression, according to the working examples. Cells were transfected with empty vector (pVec) or Snail gene (pSnail) or 48 h before seeded at $3\times10^5$ cell/ml in 24 well plate to form monolayer. *, p<0.05; **, p<0.01 with one-way ANOVA-Tukey's test or Student's t-test.

To further ascertain the functional importance of Snail in the HuR regulated EMT and migration, Snail was re-expressed in HuR KO MIA PaCa2 cells and the migration ability of such cells detected. As illustrated in FIG. 29, the restoration of Snail significantly increased migration of the HuR KO cells.

Figure 30:
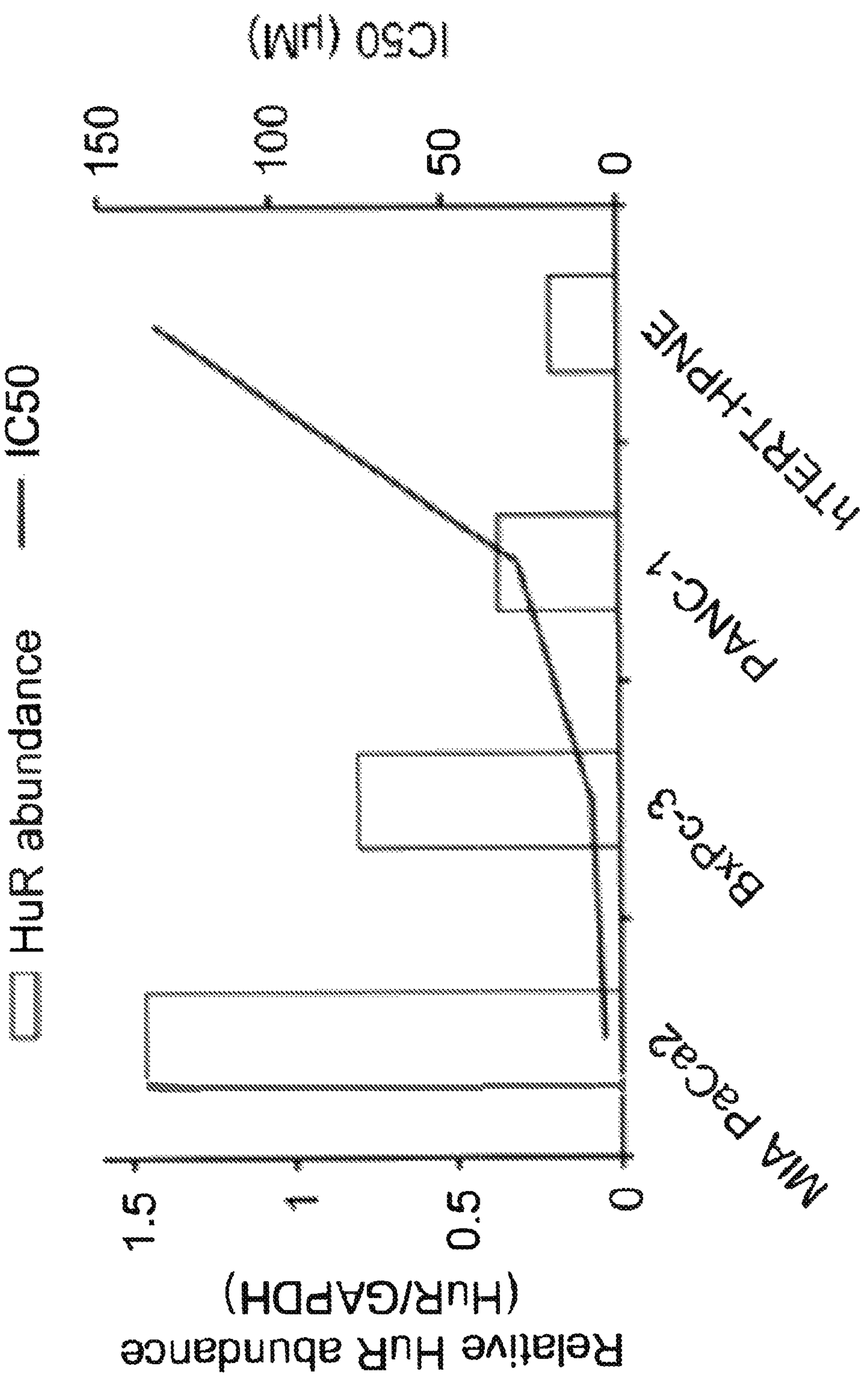
FIG. 30 provides a correlation between HuR levels of tested cell lines and the sensitivity of such cells to KH-3 treatment, according to the working examples. Bars show relative band density of HuR normalized to GAPDH, and the line shows $IC_{50}$ values of KH-3.

KH-3 Disrupts HuR-mRNA Interaction and Inhibits Pancreatic Cancer Cell Viability Depending on Endogenous HuR Levels Pancreatic cancer cell lines with different endogenous HuR expression levels were treated with serial concentrations of KH-3 for 48 hours. KH-3 induced cytotoxicity in pancreatic cancer cells, with the sensitivity correlated to endogenous HuR protein levels (FIG. 30). MIA PaCa2 cells have the highest HuR protein abundance among the tested cell lines and were the most sensitive to HuR treatment ($IC_{50}$=5 μM). PANC-1 cells have the lowest HuR expression level and were the most resistant among the tested cancer cells ($IC_{50}$=25 μM). BxPC-3 cells, another human pancreatic cancer cell line, have HuR expression level in the middle, and the $IC_{50}$ of KH-3 was in the middle (10 μM). A non-cancerous human pancreatic ductal epithelial cell line (hTERT-HPNE) was tested under the same conditions. hTERT-HPEN cells have the lowest abundance of HuR protein compared to the cancer cells, and the cytotoxicity of KH-3 to these cells were minimal ($IC_{50}$>>40 μM). There is an inverse correlation in the tested cell lines between the HuR expression levels and the sensitivity to KH-3 treatment (FIG. 30) (R=−0.71 by Pearson Tests).

Figure 31:
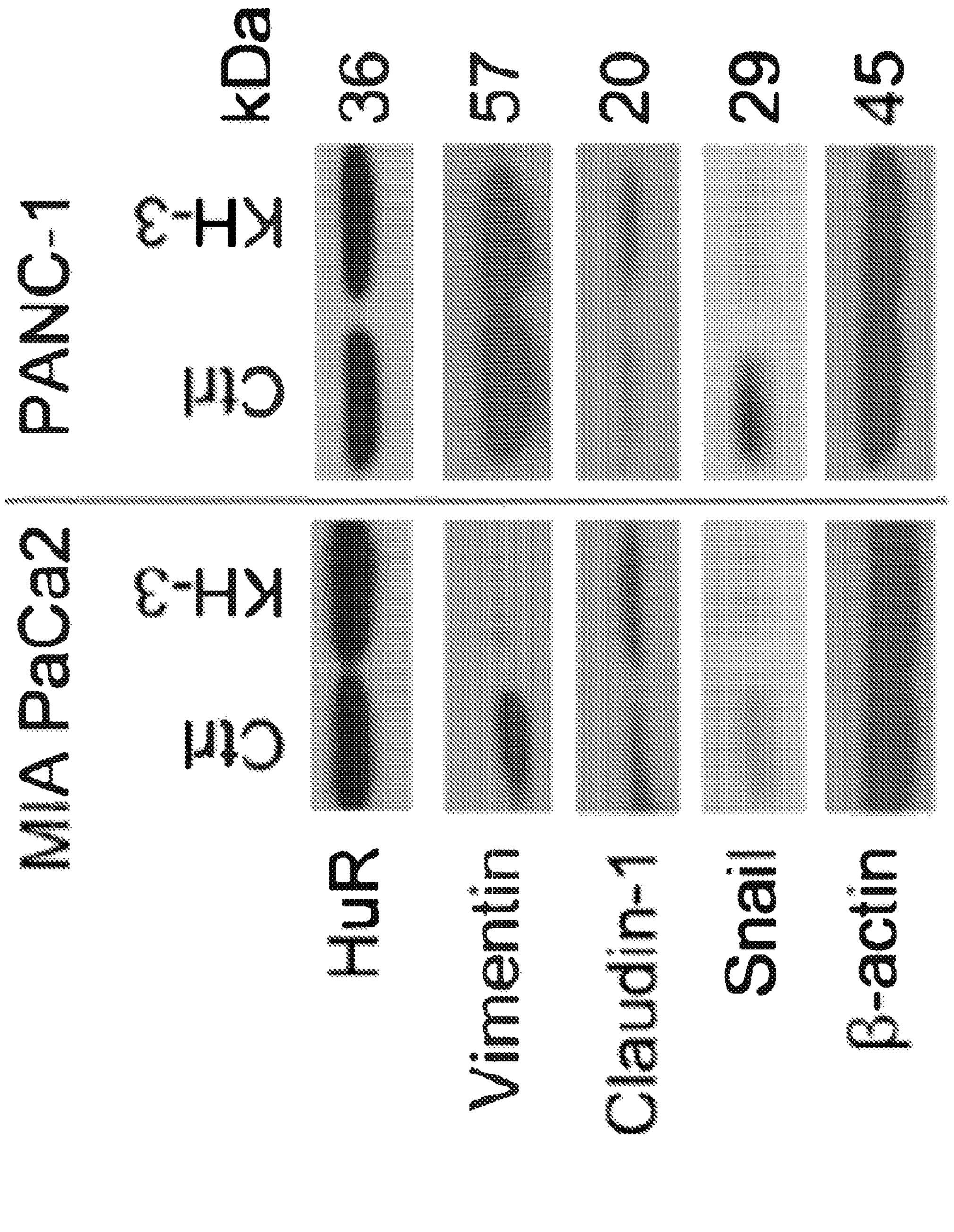
FIG. 31 provides a Western blot analysis of epithelial to mesenchymal transition (EMT) markers in MIA PaCa2 cells and PANC-1 cells, each with and without KH-3 treatment, according to the working examples.

KH-3 Inhibits Pancreatic Cancer EMT, Invasion, and CSCs by Inhibiting HuR Functions EMT signature gene expression was altered by KH-3 treatment in both MIA PaCa2 and PANC-1 cells showing Vimentin and Snail decreases, and Claudin1 increase (FIG. 31), mimicking the consequences of HuR knockdown shown above (FIG. 21). The alternation indicated EMT inhibition. HuR expression was not changed (FIG. 31), confirming that KH-3 works through interrupting HuR-mRNA binding but does not alter HuR expression.

Figure 32:
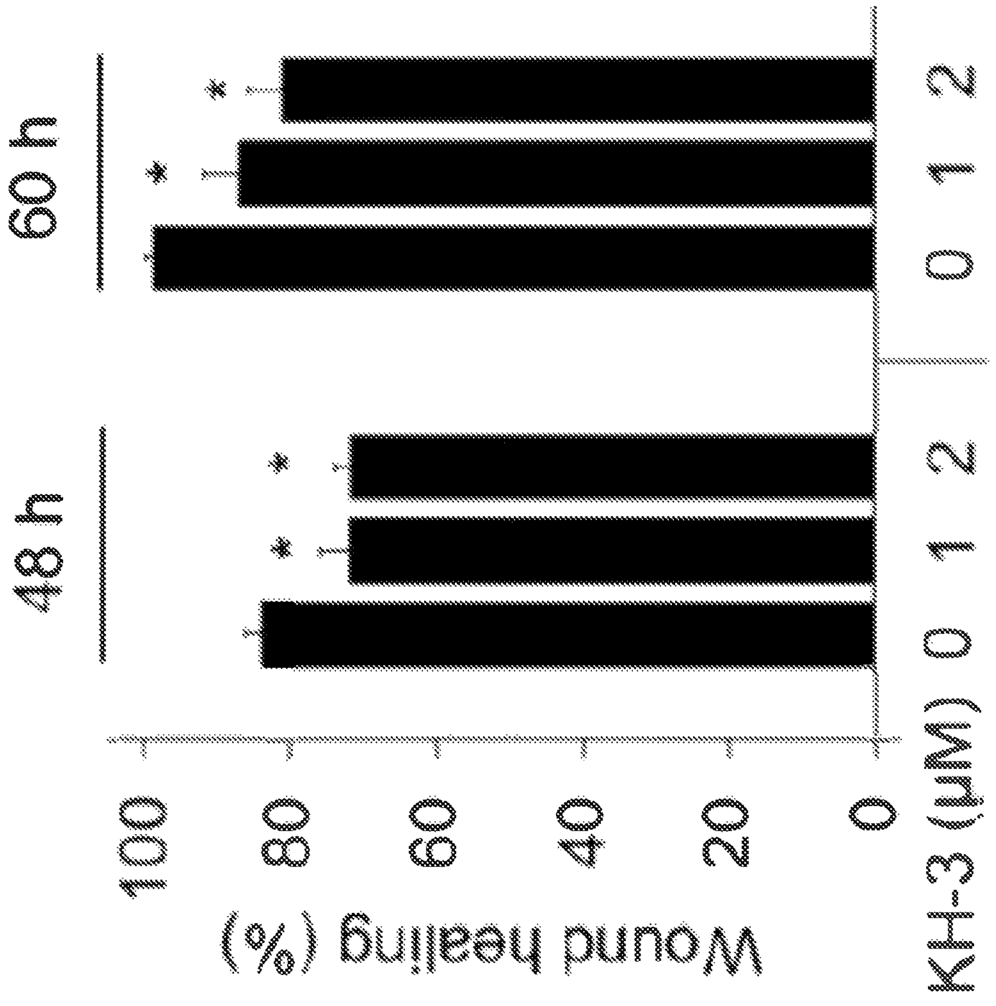
FIG. 32 provides the results of a wound healing assay in MIA PaCa-2 cells with KH-3 treatment, according to the working examples. Bar graphs show Mean±SEM of 3 repeats. *, $p<0.05$; **, $p<0.01$ with one-way ANOVA-Tukey's test.
Figure 33:
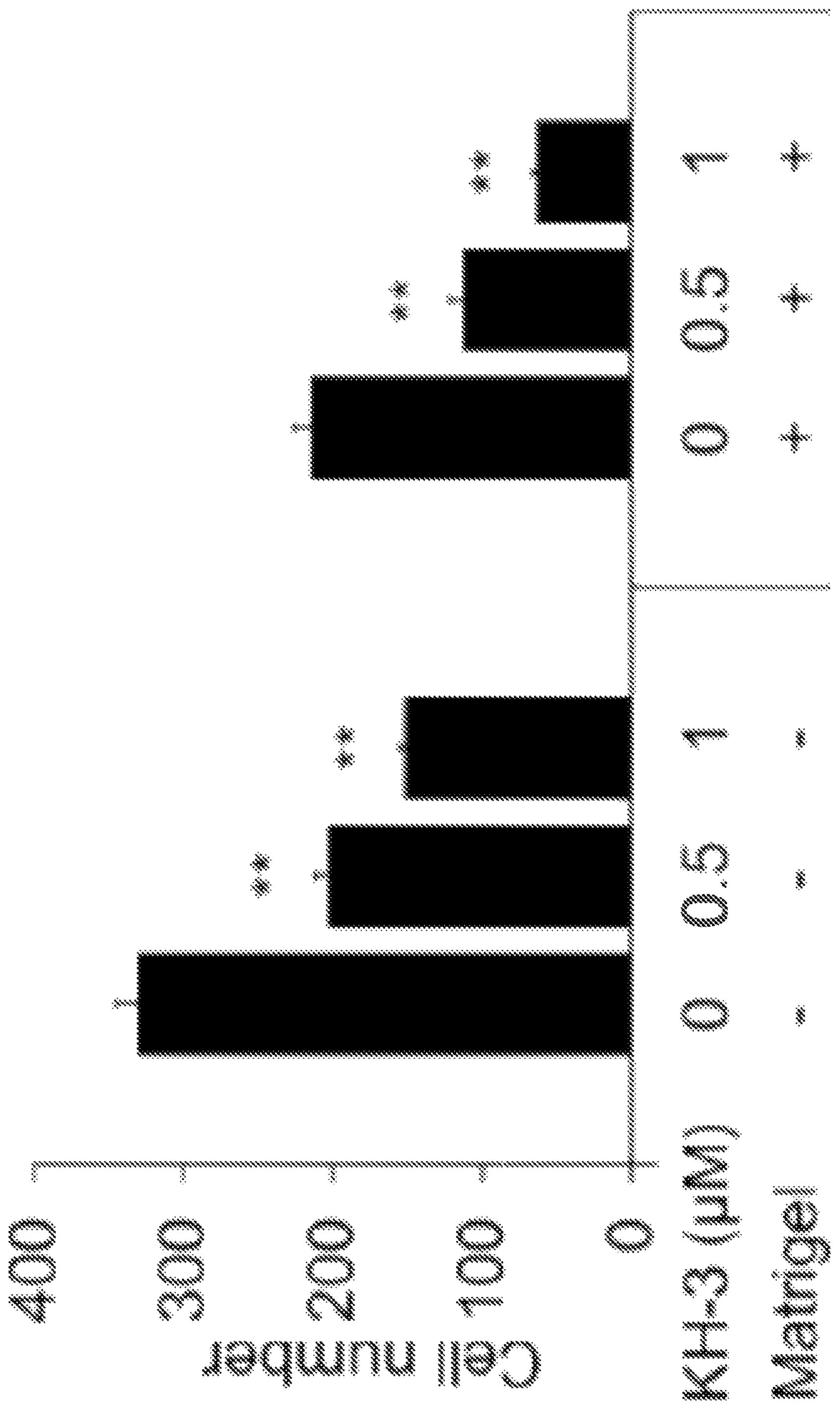
FIG. 33 provides the results of cell migration (Matrigel-) and invasion (Matrigel+) in MIA PaCa-2 cells 48 h post treatment at the indicated concentrations of KH-3, according to the working examples. Bar graphs show the Mean±SEM of migrated/invaded cells per field of at least 3 fields per experiment for 3 repeated experiments. *, $p<0.05$; **, $p<0.01$ with one-way ANOVA-Tukey's test.

KH-3 inhibited MIA PaCa2 and PANC-1 cells migration and invasion in the wound healing assay as well as in the Boyden chamber trans-well assay (Matrigel assay) (FIG. 32 illustrates wound healing assay data for KH-3 inhibition of MIA PaCa2 cells; FIG. 33 illustrates Matrigel assay data for KH-3 inhibition of MIA PaCa2 cells). To examine the target specificity of KH-3, HuR knockdown cells were used. In both the siHuR cells (MIA PaCa2 and PANC-1) and the CRISPER/Cas9 HuR KO cells (MIA PaCa2), the knockdown of HuR itself resulted in dampened migration compared to the wild type cells, as expected. Importantly, in the HuR knocked down cells, KH-3 lost its target and did not show additional effects to the effect of the knockdown. Re-expression of HuR in the HuR KO cells was accomplished by transfecting the cells with an HuR-expressing plasmid, whereupon restoration of HuR expression KH-3 showed inhibitory effect again to the migration of the cells.

Figure 34:
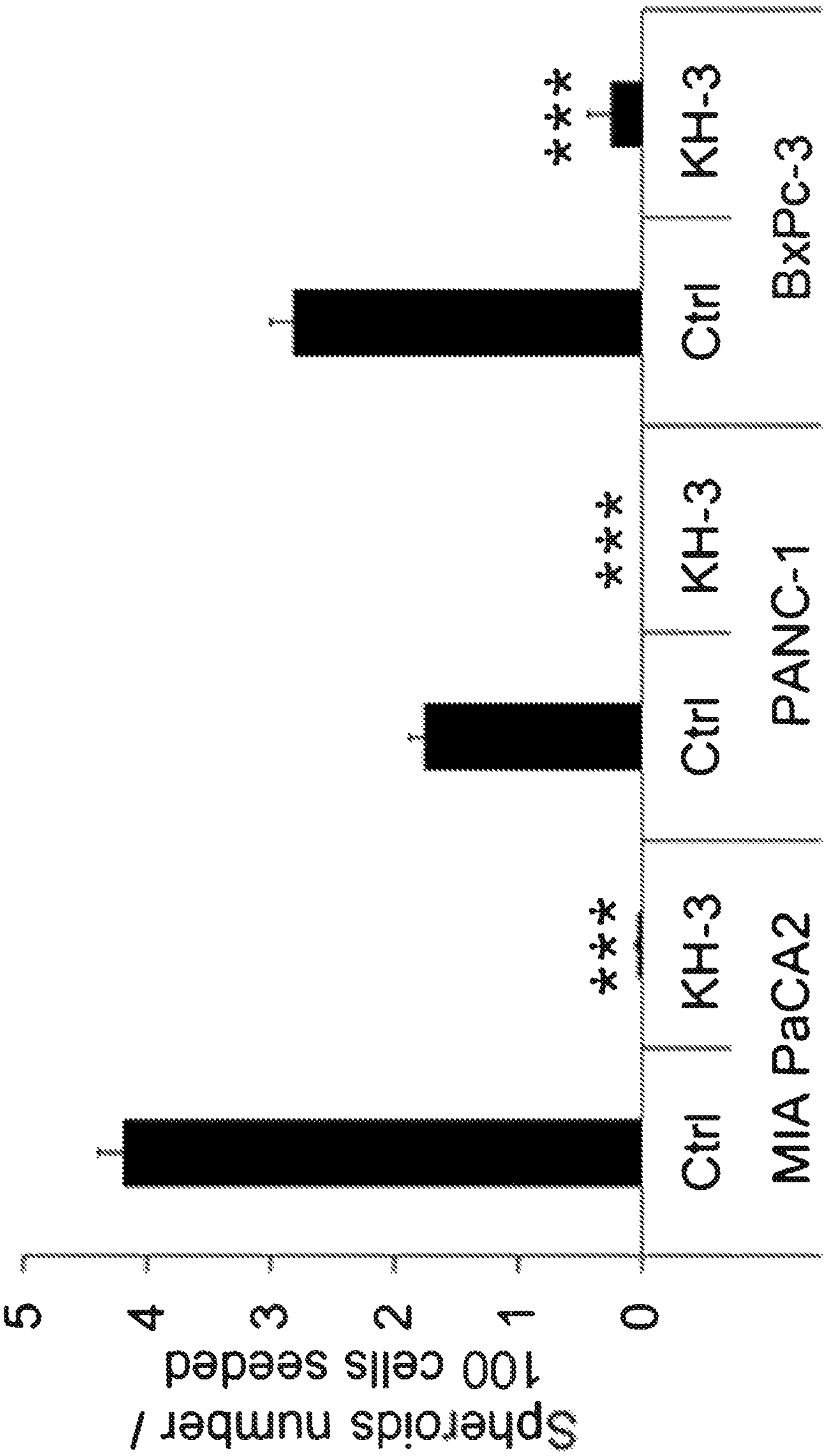
FIG. 34 provides the results of tumor spheroid formation assays described in the working examples illustrating the number of tumor spheres of MIA PaCa2, PANC-1, and BxPc-3 cells where. MIA PaCa-2 cells were treated with 4 μM of KH-3, PANC-1 cells with 10 μM, and BxPC-3 cells 8 μM, and each compared with respective controls. Spheres were imaged and counted 14 days post seeding. Bar graphs show Mean±SEM of 36 repeats. *, $p<0.05$; **, $p<0.01$ with one-way ANOVA-Tukey's test.

Tumor spheres formation was inhibited by KH-3 treatment. In PANC-1 cells, 10 μM of KH-3 eliminated tumor spheres formation, while in MIA PaCa2 cells 4 μM of KH-3 had the similar effects, and in BxPC-3 cells 8 μM of KH-3 significantly inhibited both the number and the size of tumor spheres (FIG. 34; size data not shown).

KH-3 Decreases Snail mRNA Stability and Protein Expression

Figure 35:
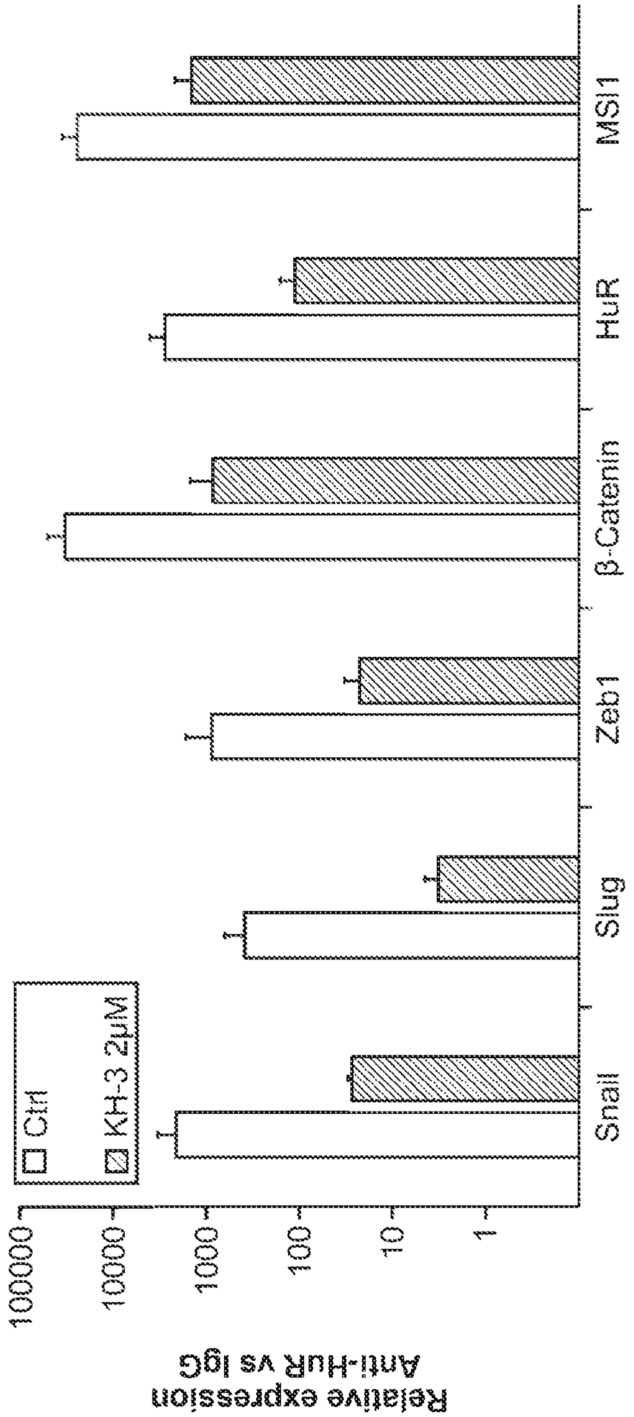
FIG. 35 provides the results of RNP-IP detection of HuR binding RNAs of EMT related genes in MIA PaCA-2 cells were treated with 2 μM of KH-3 for 24 h as compared to appropriate controls, according to the working examples. Pull-down products of whole cell lysate were subjected qRT-PCR detection. Data for each individual mRNA was normalized to the IgG pull-down product of that mRNA. Bar graphs show Mean±SEM of 9 repeats.

RNP-IP assay was performed to examine the interruption of binding between HuR and its target mRNAs with KH-3 treatment. Based on the above-results of this disclosure, it was expected the HuR downstream EMT-related mRNAs were less likely to be co-precipitated with HuR protein upon KH-3 treatment. Indeed, KH-3 treatment at 2 μM for 24 hours significantly decreased the pull-down amounts of mRNAs of Snail, Slug, Zeb1, β-catenin, HuR and Msi1 in MIA PaCa2 cells (FIG. 35), consistent with the HuR KO discussed above (see also FIG. 27). Parallel with HuR KO discussed above, the KH-3 treatment (2 μM) enhanced Snail mRNA decay and decreased the protein level of Snail.

Figure 36:
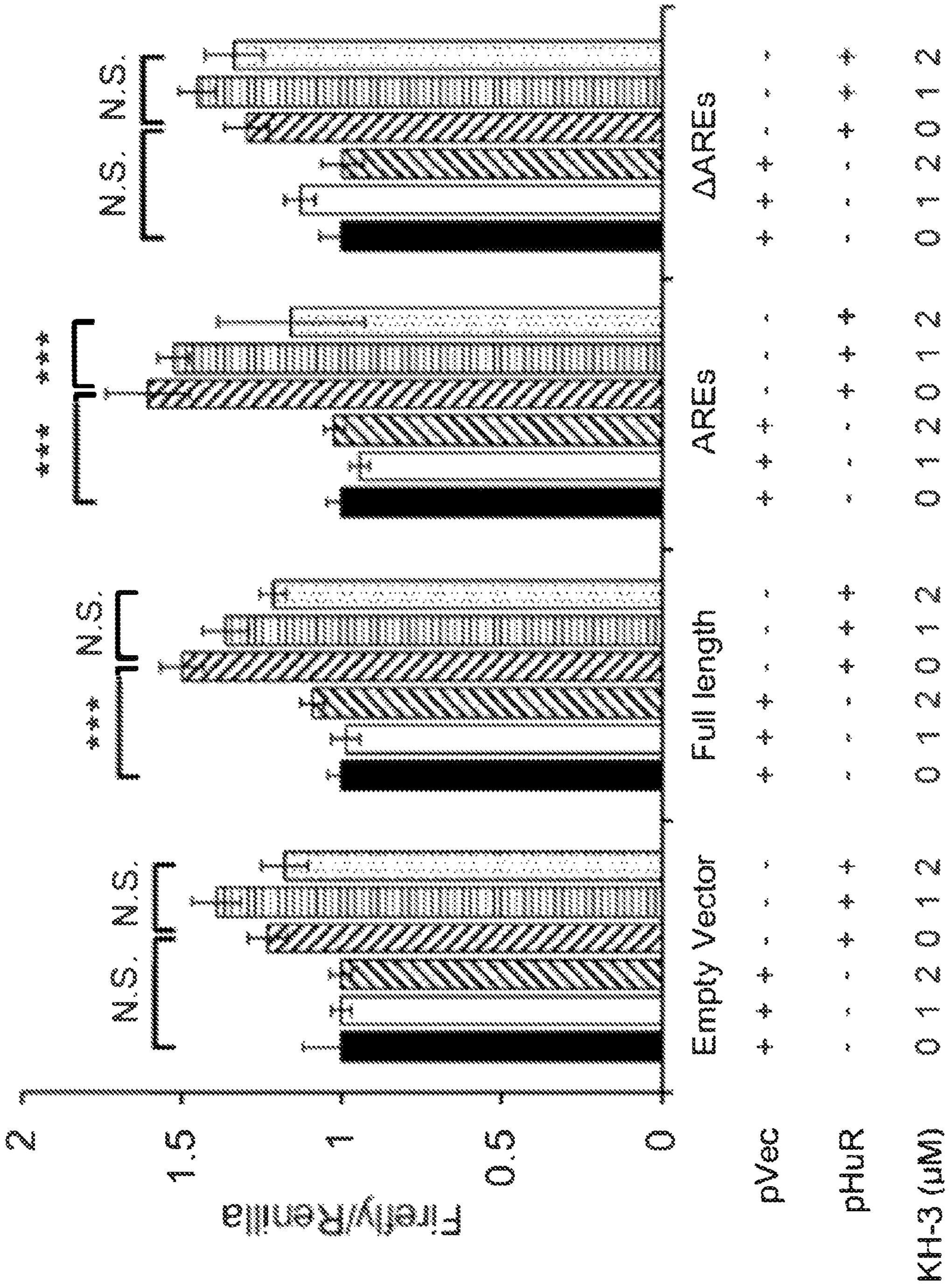
FIG. 36 provides the results of a luciferase reporter assay where MIA PaCa2 HuR KO cells were co-transfected with HuR (or vector) and the dual-luciferase reporter with Snail 3'-UTR constructions (either the Full length, AREs or ΔAREs, or empty reporter), according to the working examples. At 24 h of the co-transfection, cells were treated with KH-3 at indicated concentrations for an additional 24 h. *, $p<0.05$; ***, $p<0.001$ with one-way ANOVA-Tukey's test or Student T-test.

Interruption of KH-3 to the binding of HuR with Snail 3'-UTR was further examined in the luciferase reporter assay. With co-transfection of HuR and full-length Snail 3'-UTR or AREs, KH-3 treatment inhibited the luminescence signal (FIG. 36), clearly demonstrating interruption of HuR interaction with the 3'-UTR. When there lacked HuR binding elements (with ΔAREs), KH-3 had no influence on the luminescence signal (FIG. 36).

KH-3 Inhibits a HuR Positive Pancreatic Cancer Progression and Metastasis In Vivo.

The in vivo tumor inhibitory effects of KH-3 were tested in a highly metastatic orthotopic model of pancreatic cancer. Briefly, with $2\times10^5$ PANC-1 cells implanted into the pancreatic parenchyma of nude mouse, it gave 90% tumor formation rate in the pancreas, with ~60% of these mice having metastases in the liver and peritoneal cavity in 5 weeks. For in vivo tumor imaging purpose, cells transfected with luciferase was established. Tumor progression is monitored by weekly imaging using an IVIS Spectrum imaging system (Caliper Life Sciences). To avoid peritoneal lesions resulted from leak of injection, 5 mice (donor mice) were injected with luciferase expressing PANC-1 cells (PANC-1-Luc) and tumors were allowed to form for 4 weeks. Then tumors in the pancreas of these donor mice were harvested and cut into ~1 $mm^3$ and implanted into the pancreatic parenchyma of recipient mice. After 2 weeks, tumor development in the pancreas of the recipient mice was detected by imaging. Mice were then grouped and treatment commenced (n=9 for control group, and n=10 for KH-3 treated group). The dose regimen of KH-3 was determined by a pilot dose-finding experiment to be 100 mg/kg, intraperitoneal injection (IP), three times (3×) weekly, which was the highest dose without showing toxicity. The treatment continued for 5 weeks, and mice were euthanized and gross necropsy was performed.

Figure 37:
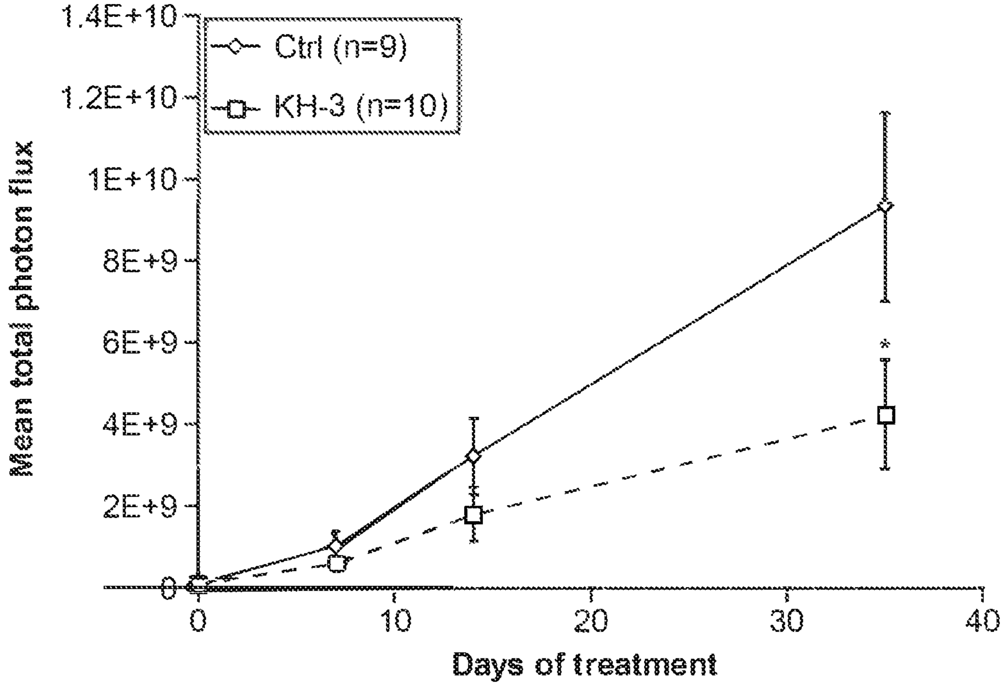
FIG. 37 provides average tumor burden by IVIS imaging, quantified as photons/sec/$cm^2$ (Mean±SEM), of mice bearing PANC-1-Luc orthotopic pancreatic xenografts treated with KH-3 (100 mg/kg, 3× weekly, n=10), or vehicle (Ctrl, n=9), according to the working examples. *, $p<0.05$ with Student's t-test.
Figure 38:
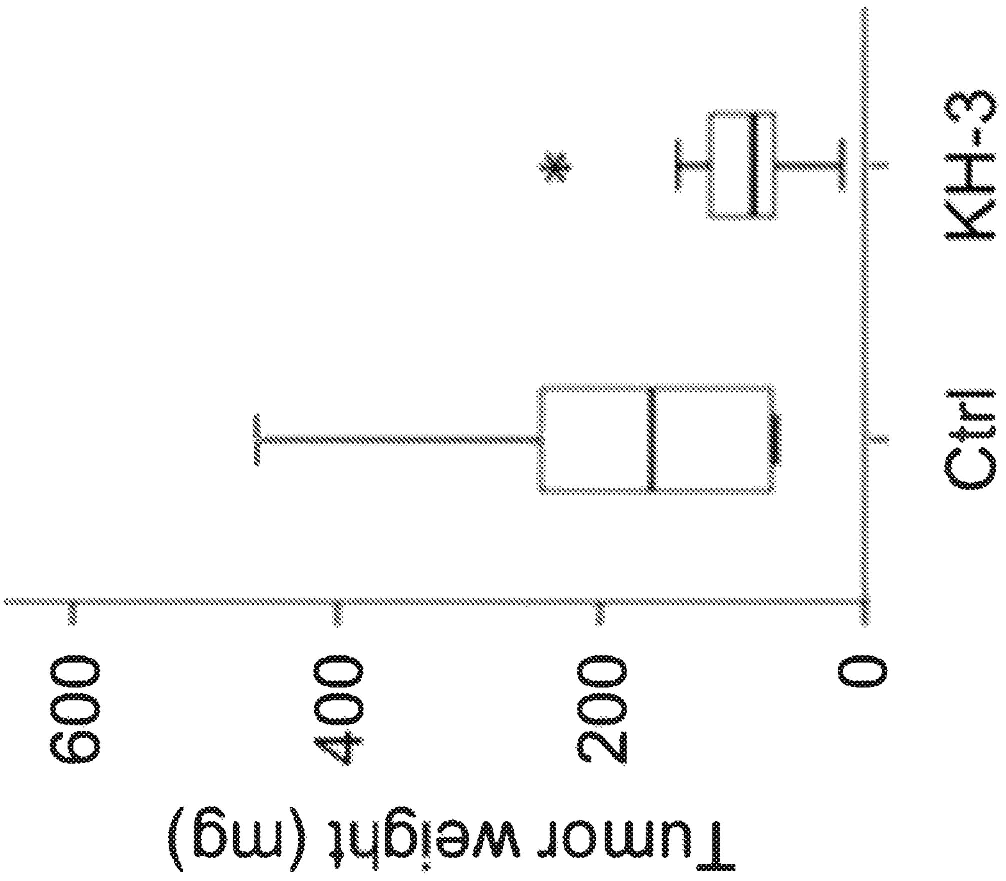
FIG. 38 provides average tumor weight at the end of the treatment of mice bearing PANC-1-Luc orthotopic pancreatic xenografts treated with KH-3 (100 mg/kg, 3× weekly, n=10), or vehicle (Ctrl, n=9), according to the working examples. *, $p<0.05$ with Student's t-test.
Figure 39:
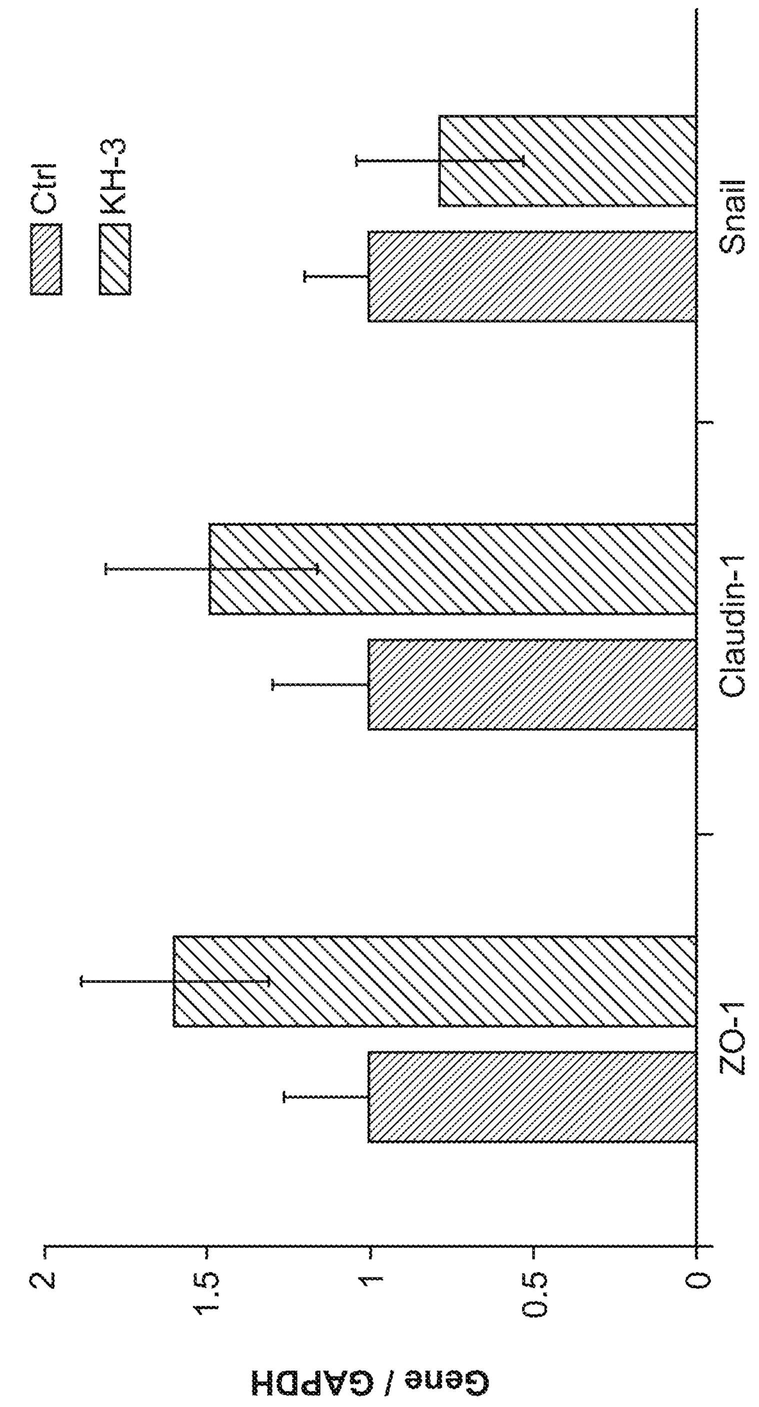
FIG. 39 provides a bar graph illustrating the results of Western blot analysis of EMT markers in mice tumor tissues at the end of the treatment of mice bearing PANC-1-Luc orthotopic pancreatic xenografts treated with KH-3 (100 mg/kg, 3× weekly, n=10), or vehicle (Ctrl, n=9), according to the working examples. Bar graphs show average band intensity of each gene relative to GAPDH.

The data showed that KH-3 treatment significantly inhibited longitudinal tumor growth and reduced tumor burden compared to the vehicle treated group (Control) (FIG. 37). The final tumor weight was significantly reduced (FIG. 38). In the control group, 5/9 mice developed uncountable lesions of metastasis in the liver (56%), whereas in the KH-3 treated group, only 1/10 mouse developed metastasis (10%). At the end of the study, tumor tissues were examined for EMT alternations by Western Blots. Consistent with the expected EMT inhibition, the epithelial markers Claudin1 and ZO1 were upregulated in the KH-3 treated mice, and Snail was downregulated by the KH-3 treatment (FIG. 39). Immunohistochemistry confirmed the high expression level of HuR in the tumor tissues compared to the adjacent normal pancreatic tissues. KH-3 treatment did not change the expression level of HuR in the tumor tissues.

Further, an in vivo treatment was performed using MIA PaCa2 HuR KO tumors, to examine whether the inhibitory effects of KH-3 were dependent on HuR. Because the HuR KO cells did not form tumors orthotopically, cells were subcutaneously inoculated, and tumor formation and growth were monitored with caliper measurement. The KH-3 treatment started on the same day the cells were inoculated. KH-3 (100 mg/kg, IP, 3× weekly) did not influence either tumor formation or tumor growth of the HuR KO tumors. This data, together with the data with the orthotopic tumor model, strongly evidence that the KH-3 effects are dependent on HuR.

REFERENCES

1. Brennan, C. M. and J. A. Steitz, *HuR and mRNA stability*. Cell Mol Life Sci, 2001. 58(2): p. 266-77.
2. Lopez de Silanes, I., et al., *Role of the RNA-binding protein HuR in colon carcinogenesis*. Oncogene, 2003. 22(46): p. 7146-54.
3. Nabors, L. B., et al., *HuR, a RNA stability factor, is expressed in malignant brain tumors and binds to adenine-and uridine-rich elements within the 3' untrans-*

*lated regions of cytokine and angiogenicfactor mRNAs*. Cancer Res, 2001. 61(5): p. 2154-61.
4. Dixon, D. A., et al., *Altered expression of the mRNA stability factor HuR promotes cyclooxygenase-2 expression in colon cancer cells*. J Clin Invest, 2001. 108(11): p. 1657-65.
5. Young, L. E., et al., *The mRNA binding proteins HuR and tristetraprolin regulate cyclooxygenase 2 expression during colon carcinogenesis*. Gastroenterology, 2009. 136 (5): p. 1669-79.
6. Yoo, P. S., et al., *Tissue microarray analysis of 560 patients with colorectal adenocarcinoma: high expression of HuR predicts poor survival*. Ann Surg Oncol, 2009. 16(1): p. 200-7.
7. Niesporek, S., et al., *Expression of the ELAV-like protein HuR in human prostate carcinoma is an indicator of disease relapse and linked to COX-2 expression*. Int J Oncol, 2008. 32(2): p. 341-7.
8. Barbisan, F., et al., *Overexpression of ELAV-like protein HuR is associated with increased COX-2 expression in atrophy, high-grade prostatic intraepithelial neoplasia, and incidental prostate cancer in cystoprostatectomies*. Eur Urol, 2009. 56(1): p. 105-12.
9. Heinonen, M., et al., *Prognostic role of HuR in hereditary breast cancer*. Clin Cancer Res, 2007. 13(23): p. 6959-63.
10. Denkert, C., et al., *Overexpression of the embryonic-lethal abnormal vision-like protein HuR in ovarian carcinoma is a prognostic factor and is associated with increased cyclooxygenase 2 expression*. Cancer Res, 2004. 64(1): p. 189-95.
11. Costantino, C. L., et al., *The role of HuR in gemcitabine efficacy in pancreatic cancer: HuR Up-regulates the expression of the gemcitabine metabolizing enzyme deoxycytidine kinase*. Cancer Res, 2009. 69(11): p. 4567-72.
12. Wang, J., et al., *The expression of RNA-binding protein HuR in non-small cell lung cancer correlates with vascular endothelial growth factor-C expression and lymph node metastasis*. Oncology, 2009. 76(6): p. 420-9.
13. Abdelmohsen, K. and M. Gorospe, *Posttranscriptional regulation of cancer traits by HuR*. Wiley Interdiscip Rev RNA, 2010. 1(2): p. 214-29.
14. Srikantan, S. and M. Gorospe, *HuR function in disease*. Front Biosci, 2012. 17: p. 189-205.
15. Wang, J., et al., *Multiple Functions of the RNA-Binding Protein HuR in Cancer Progression, Treatment Responses and Prognosis*. Int J Mol Sci, 2013. 14(5): p. 10015-41.
16. Abdelmohsen, K., et al., *miR-519 suppresses tumor growth by reducing HuR levels*. Cell Cycle, 2010. 9(7): p. 1354-9.
17. Fialcowitz-White, E. J., et al., *Specific protein domains mediate cooperative assembly of HuR oligomers on AU-rich mRNA-destabilizing sequences*. J Biol Chem, 2007. 282(29): p. 20948-59.
18. Wang, H., et al., *The structure of the ARE-binding domains of Hu antigen R (HuR) undergoes conformational changes during RNA binding*. Acta Crystallogr D Biol Crystallogr, 2013. 69(Pt 3): p. 373-80.
19. Doller, A., J. Pfeilschifter, and W. Eberhardt, *Signalling pathways regulating nucleo-cytoplasmic shuttling of the mRNA-binding protein HuR*. Cell Signal, 2008. 20(12): p. 2165-73.
20. Zhu, Z., et al., *Cytoplasmic HuR expression correlates with P-gp, HER-2 positivity, andpoor outcome in breast cancer*. Tumour Biol, 2013.
21. Barker, A., et al., *Sequence requirements for RNA binding by HuR and AUF1*. J Biochem, 2012. 151(4): p. 423-37.
22. Filippova, N., et al., *The RNA-binding protein HuR promotes glioma growth and treatment resistance*. Mol Cancer Res, 2011. 9(5): p. 648-59.
23. Durie, D., et al., *RNA-binding protein HuR mediates cytoprotection through stimulation of XIAP translation*. Oncogene, 2011. 30(12): p. 1460-9.
24. Vo, D. T., et al., *The oncogenic RNA-binding protein Musashi1 is regulated by HuR via mRNA translation and stability in glioblastoma cells*. Mol Cancer Res, 2012. 10(1): p. 143-55.
25. Lebedeva, S., et al., *Transcriptome-wide analysis of regulatory interactions of the RNA-binding protein HuR*. Mol Cell, 2011. 43(3): p. 340-52.
26. Choudhury, N. R., et al., *Tissue-specific control of brain-enriched miR-7 biogenesis*. Genes Dev, 2013. 27(1): p. 24-38.
27. Wang, L., et al., *ATDC TRIM29 Phosphorylation by ATM/MAPKAP Kinase 2 Mediates Radioresistance in Pancreatic Cancer Cells*. Cancer Research, 2014. 74(6): p. 1778-1788.
28. Deng, L., et al., *microRNA100 inhibits self-renewal of breast cancer stem-like cells and breast tumor development*. Cancer Research, 2014.
29. Ginestier, C., et al., *ALDH1 Is a Marker of Normal and Malignant Human Mammary Stem Cells and a Predictor of Poor Clinical Outcome*. Cell Stem Cell, 2007. 1(5): p. 555-567.
30. Al-Hajj, M., et al., *Prospective identification of tumorigenic breast cancer cells*. Proc Natl Acad Sci USA, 2003. 100(7): p. 3983-8.
31. Ishimaru, D., et al., *Regulation of Bcl-2 expression by HuR in HL60 leukemia cells and A431 carcinoma cells*. Mol Cancer Res, 2009. 7(8): p. 1354-66.
32. Ratti, A., et al., *A role for the ELAV RNA-binding proteins in neural stem cells: stabilization of Msi1 mRNA*. J Cell Sci, 2006. 119(Pt 7): p. 1442-52.
33. Wu, X., et al., *Identification and Validation of Novel Small Molecule Disruptors of HuR-mRNA Interaction*. ACS Chem Biol, 2015.
34. Mills, N. L., A. A. Shelat, and R. K. Guy, *Assay Optimization and Screening of RNA-Protein Interactions by AlphaScreen*. J Biomol Screen, 2007. 12(7): p. 946-55.
35. Xu, L., et al., (−)-*Gossypol enhances response to radiation therapy and results in tumor regression of human prostate cancer*. Mol Cancer Ther, 2005. 4(2): p. 197-205.
36. Xu, L., et al., *Systemic p53 gene therapy of cancer with immunolipoplexes targeted by anti-transferrin receptor scFv*. Mol Med, 2001. 7(10): p. 723-34.
37. Xu, L., et al., *Self-assembly of a virus-mimicking nanostructure system for efficient tumor-targeted gene delivery*. Hum Gene Ther, 2002. 13(3): p. 469-81.
38. Corbett, T. H., *Transplantable syngeneic rodent tumors*. Tumor Models in Cancer Research, ed. B. A. Teicher. 2002, Totowa: Humana Press. pp 41-71.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles, and textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A method comprising administering a compound of Formula I (I)

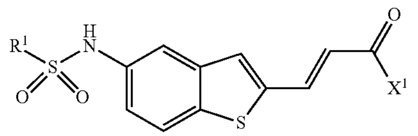

or a pharmaceutically acceptable salt thereof to a subject suffering from a hyperproliferative disease with HuR overexpression, wherein $R^1$ is

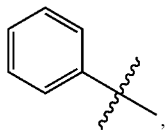,
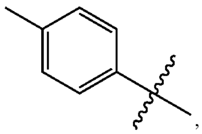,
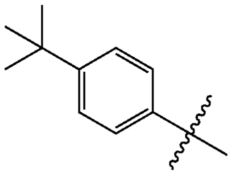, or
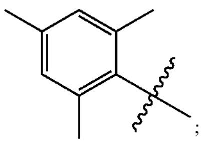;

and $X^1$ is OH, NH—OH, or O—($C_1$-$C_8$ unsubstituted alkyl).

B. The method of Paragraph A, wherein $R^1$ is

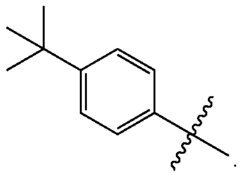 [SMILES: *c1ccc(C(C)(C)C)cc1].

C. The method of Paragraph A or Paragraph B, wherein $X^1$ is OH, NH—OH, or O—($C_1$-$C_6$ unsubstituted alkyl).

D. The method of any one of Paragraphs A-C, wherein $X^1$ is OH or NH—OH.

E. The method of any one of Paragraphs A-D, wherein $X^1$ is NH—OH.

F. The method of any one of Paragraphs A-E, wherein the method comprises administering an effective amount of the compound, wherein the effective amount is an amount effective to treat a hyperproliferative disease with HuR overexpression.

G. The method of any one of Paragraphs A-E, wherein the method comprises administering a first amount of the compound and administering a second amount of one or more therapeutic agents, wherein the first amount and second amount combined are effective to treat hyperproliferative disease with HuR overexpression.

H. The method of Paragraph G, wherein the therapeutic agent is a chemotherapeutic compound, radiation, or both.

I. The method of Paragraph G or Paragraph H, wherein the therapeutic agent comprises docetaxel, doxorubicin, or both.

J. The method of any one of Paragraphs A-I, wherein the hyperproliferative disease with HuR overexpression is a colon cancer, a prostate cancer, a breast cancer, a brain cancer, an ovarian cancer, a pancreatic cancer, or a lung cancer.

K. A pharmaceutical composition for use in treating a hyperproliferative disease with HuR overexpression, the composition comprising an effective amount of a compound of Formula I (I)

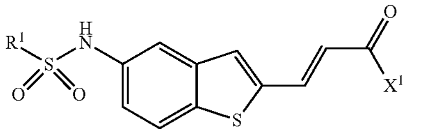

or a pharmaceutically acceptable salt thereof to a subject, wherein $R^1$ is

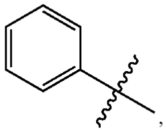,
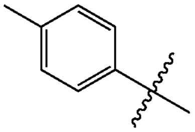,
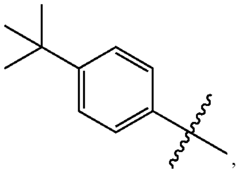, or
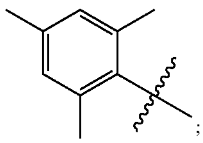;

and $X^1$ is OH, NH—OH, or O—($C_1$-$C_8$ unsubstituted alkyl).

L. The pharmaceutical composition of Paragraph K, wherein the hyperproliferative disease with HuR overexpression is a colon cancer, a prostate cancer, a breast cancer, a brain cancer, an ovarian cancer, a pancreatic cancer, or a lung cancer.

M. The pharmaceutical composition of Paragraph K or Paragraph L, wherein the pharmaceutical composition further comprises a pharmaceutically acceptable carrier.

N. The pharmaceutical composition of any one of Paragraphs K-M, wherein $R^1$ is

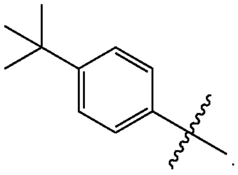 [SMILES: *c1ccc(C(C)(C)C)cc1].

O. The pharmaceutical composition of any one of Paragraphs K-N, wherein $X^1$ is OH, NH—OH, or O—($C_1$-$C_6$ unsubstituted alkyl).

P. The pharmaceutical composition of any one of Paragraphs K-O, wherein $X^1$ is OH or NH—OH.

Q. The pharmaceutical composition of any one of Paragraphs K-P, wherein $X^1$ is NH—OH.

Other embodiments are set forth in the following claims, along with the full scope of equivalents to which such claims are entitled.

The invention claimed is:

1. A method comprising administering an effective amount of a compound of Formula I (I)

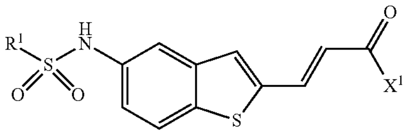

or a pharmaceutically acceptable salt thereof to a subject suffering from a hyperproliferative disease with HuR overexpression, wherein $R^1$ is

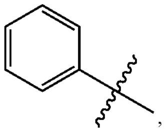,
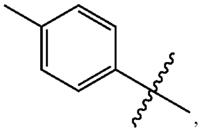,
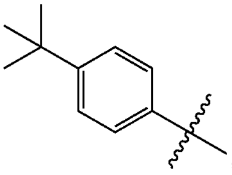, or
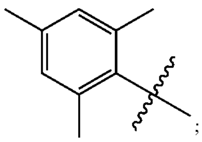;

and $X^1$ is OH, NH—OH, or O—($C_1$-$C_8$ unsubstituted alkyl), the hyperproliferative disease with HuR overexpression is a colon cancer, a prostate cancer, a breast cancer, a brain cancer, an ovarian cancer, or a pancreatic cancer; and the effective amount is an amount effective to treat the hyperproliferative disease with HuR overexpression.

2. The method of claim 1, wherein $R^1$ is

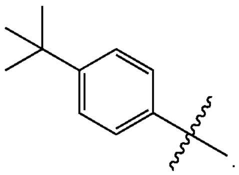 [SMILES: *c1ccc(C(C)(C)C)cc1]

3. The method of claim 1, wherein $X^1$ is OH, NH—OH, or O—($C_1$-$C_6$ unsubstituted alkyl).

4. The method of claim 1, wherein $X^1$ is OH or NH—OH.

5. The method of claim 1, wherein $X^1$ is NH—OH.

6. The method of claim 1, wherein the method comprises administering a first amount of the compound and administering a second amount of one or more therapeutic agents, wherein the first amount and second amount combined are effective to treat the hyperproliferative disease with HuR overexpression.

7. The method of claim 6, wherein the one or more therapeutic agents comprise a chemotherapeutic compound, radiation, or both.

8. The method of claim 6, wherein the one or more therapeutic agents comprise docetaxel, doxorubicin, or both.

9. A pharmaceutical composition, the pharmaceutical composition comprising an effective amount for treating a hyperproliferative disease with HuR overexpression of a compound of Formula I (I)

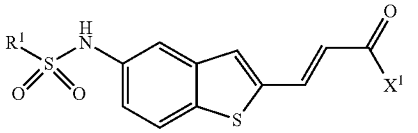

or a pharmaceutically acceptable salt thereof, wherein $R^1$ is

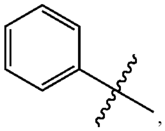,
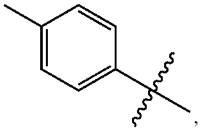,
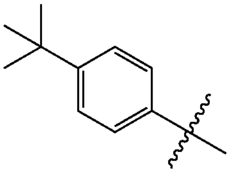, or
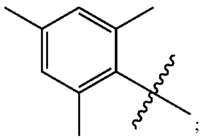;

and $X^1$ is OH, NH—OH, or O—($C_1$-$C_8$ unsubstituted alkyl), wherein the hyperproliferative disease with HuR overexpression is a colon cancer, a prostate cancer, a breast cancer, a brain cancer, an ovarian cancer, or a pancreatic cancer.

10. The pharmaceutical composition of claim 9, wherein the pharmaceutical composition further comprises a pharmaceutically acceptable carrier.

11. The pharmaceutical composition of claim 9, wherein $R^1$ is

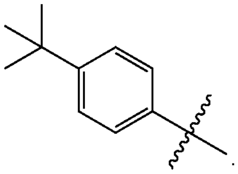 [SMILES: *c1ccc(C(C)(C)C)cc1]

12. The pharmaceutical composition of claim 9, wherein $X^1$ is OH, NH—OH, or O—($C_1$-$C_6$ unsubstituted alkyl).

13. The pharmaceutical composition of claim 9, wherein $X^1$ is OH or NH—OH.

14. The pharmaceutical composition of claim 9, wherein $X^1$ is NH—OH.

* * * * *